(12) United States Patent (10) Patent No.: US 8,740,837 B2
Childers et al. (45) Date of Patent: Jun. 3, 2014

(54) PUMPING SYSTEMS FOR CASSETTE-BASED DIALYSIS

(71) Applicants: Baxter International Inc., Deerfield, IL (US); Baxter Healthcare S.A., Glattpark (Opfikon) (CH)

(72) Inventors: Robert W. Childers, Trinity, FL (US); Brian Lauman, Clearwater, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 14/096,904

(22) Filed: Dec. 4, 2013

(65) Prior Publication Data

US 2014/0094739 A1 Apr. 3, 2014

Related U.S. Application Data

(60) Division of application No. 13/528,502, filed on Jun. 20, 2012, which is a continuation of application No. 11/773,148, filed on Jul. 3, 2007, now Pat. No. 8,206,338, which is a continuation of application No. 11/617,527, filed on Dec. 28, 2006, now Pat. No. 7,867,189, which is a continuation of application No. 10/335,646, filed on Dec. 31, 2002, now Pat. No. 7,238,164.

(60) Provisional application No. 60/397,045, filed on Jul. 19, 2002, provisional application No. 60/397,268, filed on Jul. 19, 2002.

(51) Int. Cl.
*A61M 1/00* (2006.01)
(52) U.S. Cl.
USPC ............................................ 604/29

(58) Field of Classification Search
USPC ............................................ 604/29
See application file for complete search history.

(56) References Cited

U.S. PATENT DOCUMENTS

| 2,286,613 | A | 6/1942 | Fuller |
| 3,327,115 | A | 6/1967 | Barlett |

(Continued)

FOREIGN PATENT DOCUMENTS

| DE | 1226740 | 10/1966 |
| DE | 19837667 | 3/2000 |

(Continued)

OTHER PUBLICATIONS

Bergstrom et al., An Automated Apparatus for Peritoneal Dialysis with Volumetric Fluid Balance Measurement, reprinted from Dialysis & Transplantation, Jun./Jul. 1976.

(Continued)

*Primary Examiner* — Jason Flick
(74) *Attorney, Agent, or Firm* — K&L Gates LLP

(57) ABSTRACT

A dialysis machine includes: a hardware unit including at least one pump actuator, at least one valve actuator and a cassette interface, the cassette interface including: (i) a plate that abuts the cassette; (ii) at least one pump aperture defined by the plate; (iii) at least one pump head moveable out of and retractable into the at least one pump aperture to operate a pumping portion of the cassette; (iv) at least one valve aperture defined by the plate; (v) at least one valve apparatus moveable out of and retractable into the at least one valve aperture to operate a valve portion of the cassette; (vi) at least one sensor aperture defined by the plate; and (vii) at least one sensor located in the least one sensor aperture, the at least one sensor operable with a sensor portion of the cassette.

5 Claims, 24 Drawing Sheets

(56) References Cited

U.S. PATENT DOCUMENTS

| | | |
|---|---|---|
| 3,485,245 A | 12/1969 | Lahr et al. |
| 3,620,215 A | 11/1971 | Tysk et al. |
| 3,626,670 A | 12/1971 | Pecker |
| 3,656,873 A | 4/1972 | Schiff |
| 3,689,204 A | 9/1972 | Prisk |
| 3,703,959 A | 11/1972 | Raymond |
| 3,707,967 A | 1/1973 | Kitrilakis et al. |
| 3,709,222 A | 1/1973 | DeVries |
| 3,792,643 A | 2/1974 | Scheafer |
| 3,902,490 A | 9/1975 | Jacobsen |
| 3,955,901 A | 5/1976 | Hamilton |
| 3,966,358 A | 6/1976 | Heimes et al. |
| 3,976,574 A | 8/1976 | White |
| 3,979,284 A | 9/1976 | Granger |
| 4,086,653 A | 4/1978 | Gernes |
| 4,126,132 A | 11/1978 | Portner et al. |
| 4,140,118 A | 2/1979 | Jassawalla |
| 4,142,524 A | 3/1979 | Jassawalla et al. |
| 4,158,530 A | 6/1979 | Bernstein |
| 4,181,245 A | 1/1980 | Garrett et al. |
| 4,187,057 A | 2/1980 | Xanthopoulos |
| 4,199,307 A | 4/1980 | Jassawalla |
| 4,235,231 A | 11/1980 | Schindler et al. |
| 4,236,880 A | 12/1980 | Archibald |
| 4,252,651 A | 2/1981 | Soderstrom |
| 4,265,601 A | 5/1981 | Mandoian |
| 4,273,121 A | 6/1981 | Jassawalla |
| 4,277,226 A | 7/1981 | Archibald |
| 4,303,376 A | 12/1981 | Siekmann |
| 4,310,141 A | 1/1982 | Tamura |
| 4,316,466 A | 2/1982 | Babb |
| 4,375,346 A | 3/1983 | Kraus et al. |
| 4,381,003 A | 4/1983 | Buoncristiani |
| 4,381,005 A | 4/1983 | Bujan |
| 4,382,753 A | 5/1983 | Archibald |
| 4,391,600 A | 7/1983 | Archibald |
| 4,410,322 A | 10/1983 | Archibald |
| 4,430,048 A | 2/1984 | Fritsch |
| 4,456,218 A | 6/1984 | Kawabata et al. |
| 4,468,222 A | 8/1984 | Lundquist |
| 4,479,760 A | 10/1984 | Bilstad et al. |
| 4,479,761 A | 10/1984 | Bilstad et al. |
| 4,479,762 A | 10/1984 | Bilstad et al. |
| 4,482,584 A | 11/1984 | Hess et al. |
| 4,504,038 A | 3/1985 | King |
| 4,530,759 A | 7/1985 | Schal |
| 4,552,552 A | 11/1985 | Polaschegg et al. |
| 4,559,036 A | 12/1985 | Wunsch |
| 4,559,044 A | 12/1985 | Robinson et al. |
| 4,560,472 A | 12/1985 | Granzow et al. |
| 4,585,436 A | 4/1986 | Davis et al. |
| 4,613,327 A | 9/1986 | Tegrarian et al. |
| 4,618,343 A | 10/1986 | Polaschegg |
| RE32,303 E | 12/1986 | Lasker et al. |
| 4,634,430 A | 1/1987 | Polaschegg |
| 4,639,245 A | 1/1987 | Pastrone et al. |
| 4,642,098 A | 2/1987 | Lundquist |
| 4,648,810 A | 3/1987 | Schippers et al. |
| 4,648,872 A | 3/1987 | Kamen |
| 4,657,490 A | 4/1987 | Abbott |
| 4,694,848 A | 9/1987 | Jorgensen et al. |
| 4,696,671 A | 9/1987 | Epstein et al. |
| 4,703,773 A | 11/1987 | Hansen et al. |
| 4,710,166 A | 12/1987 | Thompson et al. |
| 4,717,117 A | 1/1988 | Cook |
| 4,747,822 A | 5/1988 | Peabody |
| 4,769,134 A | 9/1988 | Allan et al. |
| 4,778,356 A | 10/1988 | Hicks |
| 4,778,451 A | 10/1988 | Kamen |
| 4,784,576 A | 11/1988 | Bloom et al. |
| 4,808,161 A | 2/1989 | Kamen |
| 4,816,019 A | 3/1989 | Kamen |
| 4,818,186 A | 4/1989 | Pastrone et al. |
| 4,818,190 A | 4/1989 | Pelmulder et al. |
| 4,823,552 A | 4/1989 | Ezell et al. |
| 4,826,482 A | 5/1989 | Kamen |
| 4,828,545 A | 5/1989 | Epstein et al. |
| 4,830,586 A | 5/1989 | Herter et al. |
| 4,842,582 A | 6/1989 | Mahurkar |
| 4,842,584 A | 6/1989 | Pastrone |
| 4,848,722 A | 7/1989 | Webster |
| 4,850,805 A | 7/1989 | Madsen et al. |
| 4,852,851 A | 8/1989 | Webster |
| 4,855,356 A | 8/1989 | Holub et al. |
| 4,859,319 A | 8/1989 | Borsari |
| 4,865,584 A | 9/1989 | Epstein et al. |
| 4,872,813 A | 10/1989 | Gorton et al. |
| 4,886,432 A | 12/1989 | Kimberlin |
| 4,927,411 A | 5/1990 | Pastrone et al. |
| 4,942,735 A | 7/1990 | Mushika et al. |
| 5,002,471 A | 3/1991 | Perlov |
| 5,006,050 A | 4/1991 | Cooke et al. |
| 5,006,601 A | 4/1991 | Lutz et al. |
| 5,062,774 A | 11/1991 | Kramer et al. |
| 5,088,515 A | 2/1992 | Kamen |
| 5,094,820 A | 3/1992 | Maxwell et al. |
| 5,098,262 A | 3/1992 | Wecker et al. |
| 5,108,844 A | 4/1992 | Blemberg et al. |
| 5,125,891 A | 6/1992 | Hossain et al. |
| 5,141,493 A | 8/1992 | Jacobsen et al. |
| 5,163,900 A | 11/1992 | Wortrich |
| 5,176,956 A | 1/1993 | Jevne et al. |
| 5,178,182 A | 1/1993 | Kamen |
| 5,185,084 A | 2/1993 | Lapidus et al. |
| 5,195,960 A | 3/1993 | Hossain et al. |
| 5,207,642 A | 5/1993 | Orkin et al. |
| 5,241,985 A | 9/1993 | Faust et al. |
| 5,245,693 A | 9/1993 | Ford et al. |
| 5,252,044 A | 10/1993 | Raines et al. |
| 5,292,306 A | 3/1994 | Wynkoop et al. |
| 5,302,093 A | 4/1994 | Owens et al. |
| 5,316,452 A | 5/1994 | Bogen et al. |
| 5,332,372 A | 7/1994 | Reynolds |
| 5,344,292 A | 9/1994 | Rabenau et al. |
| 5,350,357 A | 9/1994 | Kamen et al. |
| 5,378,126 A | 1/1995 | Abrahamson et al. |
| 5,389,243 A | 2/1995 | Kaplan |
| 5,397,222 A | 3/1995 | Moss et al. |
| 5,409,355 A | 4/1995 | Brooke |
| 5,415,528 A | 5/1995 | Ogden et al. |
| 5,421,208 A | 6/1995 | Packard et al. |
| 5,421,823 A | 6/1995 | Kamen et al. |
| 5,429,485 A | 7/1995 | Dodge |
| 5,431,626 A | 7/1995 | Bryant et al. |
| 5,458,468 A | 10/1995 | Ye et al. |
| 5,474,683 A | 12/1995 | Bryant et al. |
| 5,476,368 A | 12/1995 | Rabenau et al. |
| 5,482,438 A | 1/1996 | Anderson et al. |
| 5,487,649 A | 1/1996 | Dorsey, III et al. |
| 5,522,769 A | 6/1996 | DeGuiseppi |
| 5,526,844 A | 6/1996 | Kamen |
| 5,533,389 A | 7/1996 | Kamen et al. |
| 5,536,412 A | 7/1996 | Ash |
| 5,540,568 A | 7/1996 | Rosen et al. |
| 5,542,919 A | 8/1996 | Simon et al. |
| 5,554,013 A | 9/1996 | Owens et al. |
| 5,556,263 A | 9/1996 | Jacobsen et al. |
| 5,570,716 A | 11/1996 | Kamen et al. |
| 5,575,310 A | 11/1996 | Kamen et al. |
| 5,578,012 A | 11/1996 | Kamen et al. |
| 5,580,460 A | 12/1996 | Polaschegg |
| 5,586,868 A | 12/1996 | Lawless et al. |
| 5,588,816 A | 12/1996 | Abbott et al. |
| 5,591,344 A | 1/1997 | Kenley et al. |
| 5,603,354 A | 2/1997 | Jacobsen et al. |
| 5,609,572 A | 3/1997 | Lang |
| 5,620,312 A | 4/1997 | Hyman et al. |
| 5,628,908 A | 5/1997 | Kamen et al. |
| 5,632,606 A | 5/1997 | Jacobsen et al. |
| 5,634,896 A | 6/1997 | Bryant et al. |
| 5,669,764 A | 9/1997 | Behringer et al. |
| 5,718,692 A | 2/1998 | Schon et al. |
| 5,722,947 A | 3/1998 | Jeppsson et al. |
| 5,758,563 A | 6/1998 | Robinson |

(56) References Cited

U.S. PATENT DOCUMENTS

| | | |
|---|---|---|
| 5,788,671 A | 8/1998 | Johnson |
| 5,790,752 A | 8/1998 | Anglin et al. |
| 5,807,075 A | 9/1998 | Jacobsen et al. |
| 5,814,004 A | 9/1998 | Tamari |
| 5,816,779 A | 10/1998 | Lawless et al. |
| 5,836,908 A | 11/1998 | Beden et al. |
| 5,871,566 A | 2/1999 | Rutz |
| 5,919,369 A | 7/1999 | Ash |
| 5,921,951 A * | 7/1999 | Morris .................. 604/6.11 |
| 5,924,975 A | 7/1999 | Goldowsky |
| 5,931,647 A | 8/1999 | Jacobsen et al. |
| 5,938,634 A | 8/1999 | Packard |
| 5,944,495 A | 8/1999 | Jacobsen et al. |
| 5,944,684 A | 8/1999 | Roberts et al. |
| 5,965,433 A | 10/1999 | Gardetto et al. |
| 5,989,423 A | 11/1999 | Kamen et al. |
| 6,007,310 A | 12/1999 | Jacobsen et al. |
| 6,017,194 A | 1/2000 | North, Jr. |
| 6,036,668 A | 3/2000 | Mathis |
| 6,041,801 A | 3/2000 | Gray et al. |
| 6,065,941 A | 5/2000 | Gray et al. |
| 6,126,403 A | 10/2000 | Yamada |
| 6,129,699 A | 10/2000 | Haight et al. |
| 6,165,154 A | 12/2000 | Gray et al. |
| 6,208,107 B1 | 3/2001 | Maske et al. |
| 6,210,361 B1 | 4/2001 | Kamen et al. |
| 6,223,130 B1 | 4/2001 | Gray et al. |
| 6,228,047 B1 | 5/2001 | Dadson |
| 6,231,320 B1 | 5/2001 | Lawless et al. |
| 6,234,991 B1 | 5/2001 | Gorsuch |
| 6,234,997 B1 | 5/2001 | Kamen et al. |
| 6,245,039 B1 | 6/2001 | Brugger et al. |
| 6,248,093 B1 | 6/2001 | Moberg |
| 6,254,567 B1 | 7/2001 | Treu et al. |
| 6,270,673 B1 | 8/2001 | Belt et al. |
| 6,280,408 B1 | 8/2001 | Sipin |
| 6,302,653 B1 | 10/2001 | Bryant et al. |
| 6,343,614 B1 | 2/2002 | Gray et al. |
| 6,364,857 B1 | 4/2002 | Gray et al. |
| 6,382,923 B1 | 5/2002 | Gray |
| 6,416,293 B1 | 7/2002 | Bouchard et al. |
| 6,484,383 B1 | 11/2002 | Herklotz |
| 6,491,656 B1 | 12/2002 | Morris |
| 6,491,658 B1 | 12/2002 | Miura et al. |
| 6,497,676 B1 | 12/2002 | Childers et al. |
| 6,503,062 B1 | 1/2003 | Gray et al. |
| 6,542,761 B1 | 4/2003 | Jahn et al. |
| 6,595,948 B2 | 7/2003 | Suzuki et al. |
| 6,645,166 B2 | 11/2003 | Scheunert et al. |
| 6,666,842 B1 | 12/2003 | Sakai |
| 6,672,841 B1 | 1/2004 | Herklotz et al. |
| 6,743,201 B1 | 6/2004 | Dönig |
| 6,752,172 B2 | 6/2004 | Lauer |
| 6,764,761 B2 | 7/2004 | Eu et al. |
| 6,814,547 B2 | 11/2004 | Childers et al. |
| 6,846,161 B2 | 1/2005 | Kline et al. |
| 6,888,269 B1 | 5/2005 | Arndt et al. |
| 6,939,111 B2 | 9/2005 | Huitt et al. |
| 6,948,918 B2 | 9/2005 | Hansen |
| 6,949,079 B1 | 9/2005 | Westberg et al. |
| 6,953,323 B2 | 10/2005 | Childers et al. |
| 7,004,924 B1 | 2/2006 | Brugger et al. |
| 7,033,539 B2 | 4/2006 | Krensky et al. |
| 7,107,837 B2 | 9/2006 | Lauman et al. |
| 7,115,228 B2 | 10/2006 | Lundtveit et al. |
| 7,153,286 B2 | 12/2006 | Busby et al. |
| 7,175,606 B2 | 2/2007 | Bowman, Jr. et al. |
| 7,500,962 B2 | 3/2009 | Childers et al. |
| 7,815,595 B2 | 10/2010 | Busby et al. |
| 7,988,686 B2 | 8/2011 | Beden et al. |
| 8,435,408 B2 | 5/2013 | Beden et al. |
| 2001/0018937 A1 | 9/2001 | Nemoto |
| 2001/0034502 A1 | 10/2001 | Moberg et al. |
| 2002/0041825 A1 | 4/2002 | Scheunert et al. |
| 2002/0045851 A1 * | 4/2002 | Suzuki et al. .................. 604/28 |
| 2002/0062109 A1 | 5/2002 | Lauer |
| 2002/0077598 A1 | 6/2002 | Yap et al. |
| 2003/0217961 A1 | 11/2003 | Hopping |
| 2003/0220606 A1 | 11/2003 | Busby et al. |
| 2003/0220607 A1 | 11/2003 | Busby et al. |
| 2005/0118038 A1 | 6/2005 | Grey et al. |
| 2009/0216211 A1 | 8/2009 | Beden et al. |

FOREIGN PATENT DOCUMENTS

| | | |
|---|---|---|
| DE | 19919572 | 11/2000 |
| DE | 19929572 | 11/2000 |
| DE | 10034711 | 2/2002 |
| DE | 10039196 | 2/2002 |
| DE | 10042324 | 2/2002 |
| DE | 10053441 | 5/2002 |
| DE | 10157924 | 6/2003 |
| DE | 10224750 | 12/2003 |
| EP | 0 028 371 | 5/1981 |
| EP | 0 033 096 | 8/1981 |
| EP | 0 052 004 | 5/1982 |
| EP | 0 097 432 | 1/1984 |
| EP | 0 157 024 | 10/1985 |
| EP | 0 206 195 | 12/1986 |
| EP | 0 319 272 | 6/1989 |
| EP | 0 402 505 | 12/1990 |
| EP | 0 410 125 | 1/1991 |
| EP | 0 660 725 | 7/1995 |
| EP | 0 947 814 | 10/1999 |
| EP | 0 956 876 | 11/1999 |
| EP | 1 201 264 | 5/2002 |
| EP | 0 957 954 | 5/2003 |
| EP | 1314443 | 5/2003 |
| EP | 1 403 519 | 3/2004 |
| EP | 1 546 556 | 12/2006 |
| EP | 1 754 890 | 2/2007 |
| GB | 1 326 236 | 8/1973 |
| JP | 03-06859 | 10/1991 |
| PT | 1201264 | 10/2001 |
| WO | 85/04813 | 11/1985 |
| WO | 86/01115 | 2/1986 |
| WO | 87/05223 | 9/1987 |
| WO | 89/01795 | 3/1989 |
| WO | 90/13795 | 11/1990 |
| WO | 94/20158 | 9/1994 |
| WO | 98/22167 | 5/1998 |
| WO | 03/099355 | 12/2003 |

OTHER PUBLICATIONS

Bran & Luebbe GmbH, Diaphragm Metering Pumps, Chem. Eng'g Progress, Apr. 1987, at 18-24.

Brochure entitled Fresenius Delivers 90/2 Peritoneal Therapy Cycler (Apr. 2001).

Brochure entitled, AP Hauni: Automatisches Peritonealdialyse-Great (1970).

Brochure entitled, for Volume Measurement, Temperature Control and Cycling of Dialysing Fluid, Peritoneal Dialyser PD700, 1970.

Brochure entitled, Peritoneal Dialyser PD700, May 1979.

Defendants' Final Invalidity Contentions for U.S. Patent No. 6,814,547, *Baxter Healthcare Corporation v. Fresenius Medical Care Holdings*, Case No. C 07-01359 PJH (JL), filed Apr. 1, 2009.

Defendants' Preliminary Invalidity Contentions for U.S. Patent No. 6,814,547, *Baxter Healthcare Corporation v. Fresenius Medical Care Holdings*, Case No. C 07-01359 PJH (JL), filed Jan. 31, 2008.

Document entitled 90/2 Cycler Software, Version 3.96 (Jan. 24, 1992).

Drukker et al., Replacement of Renal Function by Dialysis, 2nd Ed., Ch. 21, 1983.

Elsevier Science Ltd., Air-Operated Diaphragm Pumps, World Pumps, Jan. 1996, at 38.

Expert Witness Report of Ronald J. Adrian Regarding Lack of Written Description, Lack of Enablement, and Indefiniteness of the Asserted Claim (Claim 12) of U.S. Patent No. 6,814,547, Apr. 24, 2009.

Fresenius Delivers 90/2 Peritoneal Therapy Cycler (on information and belief, on sale in United States by 1991).

(56) References Cited

OTHER PUBLICATIONS

Fresenius USA/Delmed 90/2 Peritoneal Dialysis System Operators Manual, dated Feb. 6, 1991.
Memorandum of Donald X. Vaccarino entitled 90/2 History File (1991-1992).
Operator's Instructions, Fresenius 90/2 Peritoneal Therapy Cycler (Rev. C. copyright 1991-2000).
PD700 Peritoneal Dialyser Users Hand-book, Dec. 1977.
Peritoneal Dialyser PD700 Service Manual, Jun. 1977.
Technical Note, PD700 Peritoneal Dialyser, Jan. 29, 1979.
Defendants' L.P.R. 2.3 Initial Non-Infringement and Invalidity Contentions (w/Exhibits), Nov. 20, 2012.
Defendants' L.P.R. 3.1 Final Invalidity Contentions, Mar. 29, 2013.
Exhibit 1 to Defendants' L.P.R. 3.1 Final Invalidity Contentions, Mar. 29, 2013.
Exhibit 2 to Defendants' L.P.R. 3.1 Final Invalidity Contentions, Mar. 29, 2013.
Exhibit 3 to Defendants' L.P.R. 3.1 Final Invalidity Contentions, Mar. 29, 2013.
Fresenius Medical Care Sleep-Safe Communicating Therapy, Bates range F0504536-0504544, Copyright 1999.
Frenius Medical Care Slide Presentation for sleepsafeTM, Bates range F0000376-F0000500, Oct. 13, 1999.
SleepsafeTM Brochure, Bates range F0000501-0000526, 2001.
Fresenius Medical Care Acute Dialysis Operating Instructions for acu-men Software Version 1.0, Bates range F0000902-0001047, May 1, 1996.
Phillips et al., "Artificial Heart Evaluation Using Flow Visualization Techniques," published in Transactions: American Society for Artificial Internal Organs, vol. XVIII (1972).
Ronco et al., "Evolution of Machines for Automated Peritoneal Dialysis", Technical Aspects and Solutions for ADP, 1999, pp. 142-161, vol. 129.
Non-Final Office Action for U.S. Appl. No. 10/155,754 mailed Sep. 11, 2003.
Final Office Action for U.S. Appl. No. 10/155,754 mailed Mar. 24, 2004.
Sleep-safeTM Technical Manual, Part No. 6778071, 2nd Edition, Dec. 2001.
Non-Final Office Action for U.S. Appl. No. 11/614,858 mailed May 13, 2010.
Non-Final Office Action for U.S. Appl. No. 11/617,527 mailed Nov. 24, 2008.
Non-Final Office Action for U.S. Appl. No. 10/446,068 mailed May 12, 2006.
Final Office Action for U.S. Appl. No. 10/446,068 mailed Nov. 7, 2006.
Non-Final Office Action for U.S. Appl. No. 10/446,068 mailed Sep. 7, 2007.
Final Office Action for U.S. Appl. No. 10/446,068 mailed Feb. 28, 2008.
Final Office Action for U.S. Appl. No. 10/446,068 mailed Jul. 31, 2008.
Non-Final Office Action for U.S. Appl. No. 10/446,068 mailed Nov. 14, 2008.
Non-Final Office Action for U.S. Appl. No. 11/773,787 mailed Jul. 28, 2010.
Non-Final Office Action for U.S. Appl. No. 12/506,738 mailed Jun. 24, 2011.
Non-Final Office Action for U.S. Appl. No. 12/903,902 mailed Jul. 6, 2011.
Non-Final Office Action for U.S. Appl. No. 12/903,887 mailed Jul. 6, 2011.
Non-Final Office Action for U.S. Appl. No. 12/408,432 mailed Mar. 3, 2011.
Non-Final Office Action for U.S. Appl. No. 11/617,543 mailed Sep. 24, 2007.
Final Office Action for U.S. Appl. No. 11/617,543 mailed May 30, 2008.
Non-Final Office Action for U.S. Appl. No. 11/617,543 mailed Oct. 20, 2008.
Final Office Action for U.S. Appl. No. 11/617,543 mailed Jul. 22, 2009.
Non-Final Office Action for U.S. Appl. No. 12/987,738 mailed Apr. 29, 2011.
European Search Report issued Jul. 18, 2012, for related European Appln. No. 10075477.9.
European Search Report issued Mar. 25, 2013 for related European Appln. No. 100754795.5.
Fresenius Freedom Cycler Operating Instructions, Bates Nos. FRES2078159-FRES2078220.
Peritoneal Dialyser PD700 Instruction Manual, Bates Nos. FRES2070909-FRES2070926.
Translation of brochure, SIF 901 Perugia, Bates Nos. FRES068838-FRES068842.
Translation of Certificate for translation of brochure entitled SIF 901 Perugia, Bates No. FRES068843.
Fresenius Medical Care Sleep-Safe Product Range F0504245-0504550, 2001.
Fresenius Medical Care, The Sign for Safe and Biocompatible CAPD, Stay Safe Balance.
Operating Instructions, Peritoneal Dialyser, PD700, For Serial No. 300.

* cited by examiner

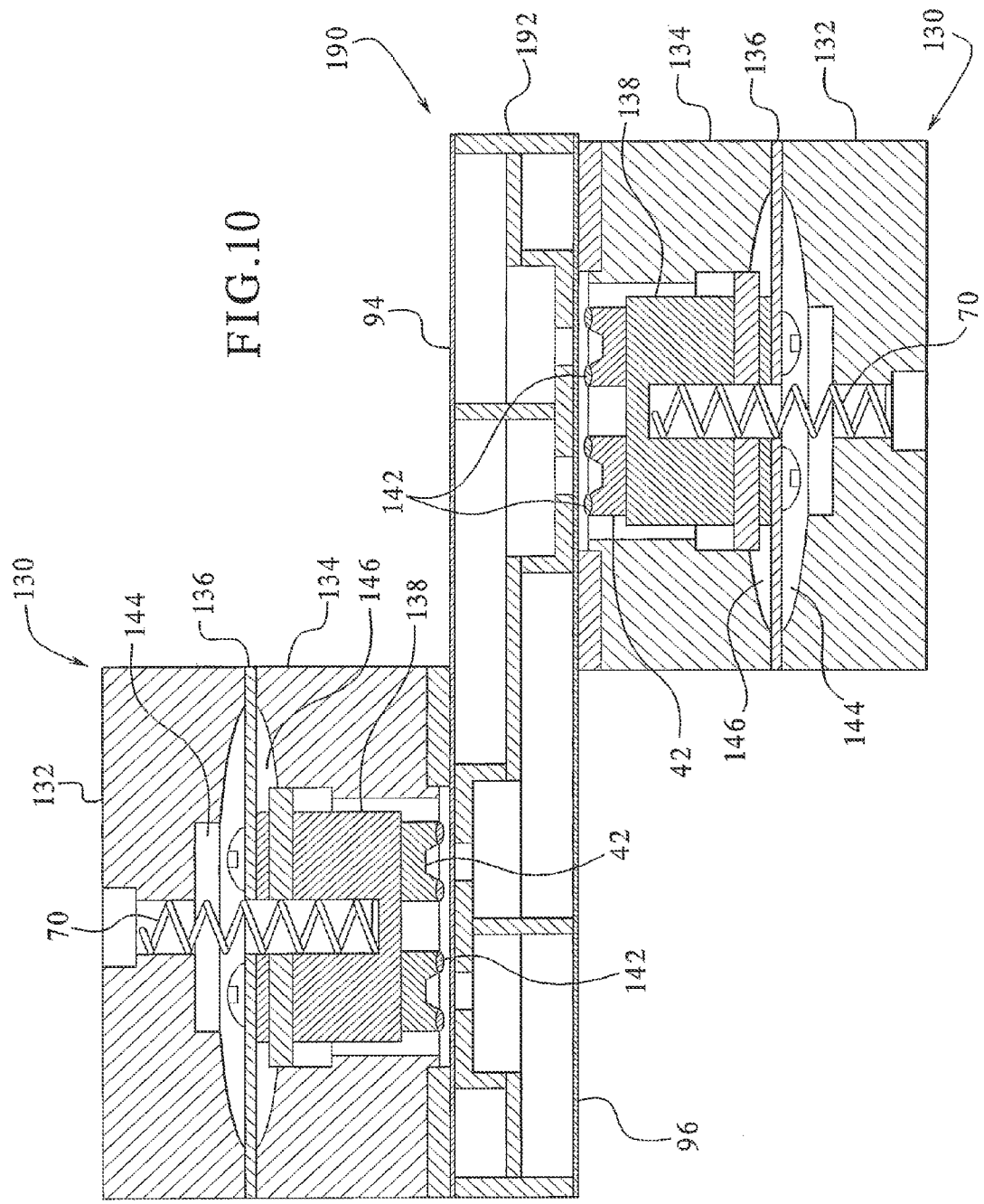

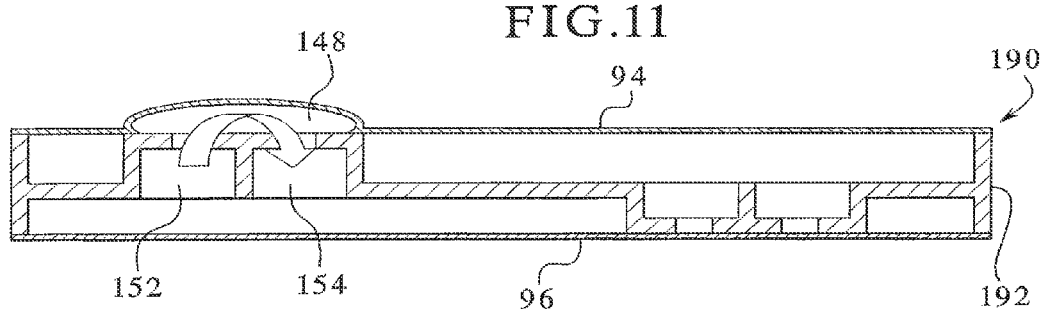
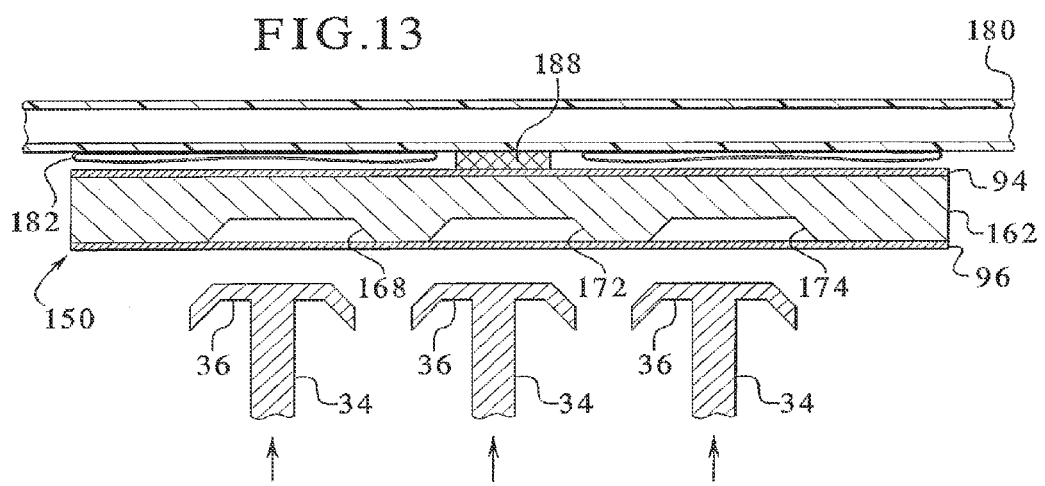
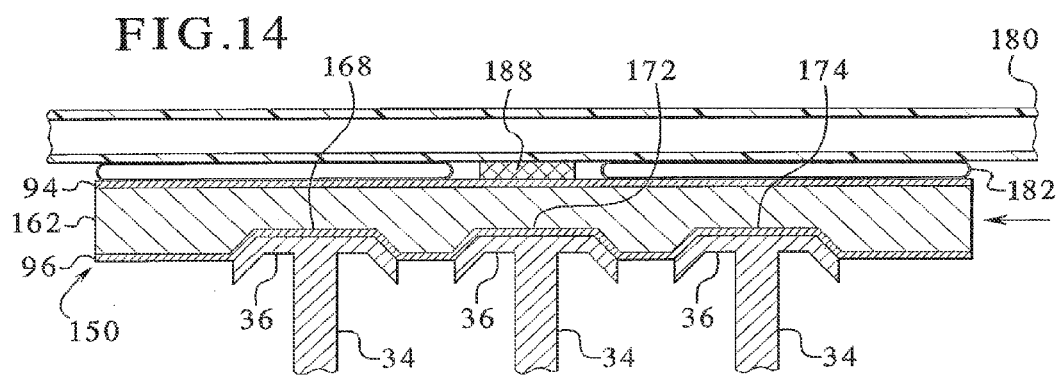

FIG. 18

|  | 12 sec | | 24 sec | | 36 sec | | 48 sec | | 1 min | |
|---|---|---|---|---|---|---|---|---|---|---|
| Pump 1 | 10ml | --- | 10ml | --- | 10ml | --- | 10ml | --- | 10ml | --- |
| Pump 2 | --- | 10ml | --- | 10ml | --- | 10ml | --- | 10ml | --- | 10ml |

FIG. 19

| Additive ml/min | One Total Chamber Volume Every X Strokes (P1 + P2) | One Total Chamber Volume Every Y Minutes |
|---|---|---|
| 0.2 | 500.0 | 50.0 |
| 0.5 | 200.0 | 20.0 |
| 1.0 | 100.0 | 10.0 |
| 1.5 | 66.7 | 6.7 |
| 2.0 | 50.0 | 5.0 |
| 3.0 | 33.3 | 3.3 |

FIG. 20

| Remove ml/min | One Full Chamber Volume Every X Strokes (P1 + P2) | One Full Chamber Volume Every Y Minutes |
|---|---|---|
| 1.0 | 100.0 | 10.0 |
| 2.0 | 50.0 | 5.0 |
| 3.0 | 33.3 | 3.3 |
| 4.0 | 25.0 | 2.5 |
| 5.0 | 20.0 | 2.0 |
| 6.0 | 16.7 | 1.7 |
| 7.0 | 14.3 | 1.4 |

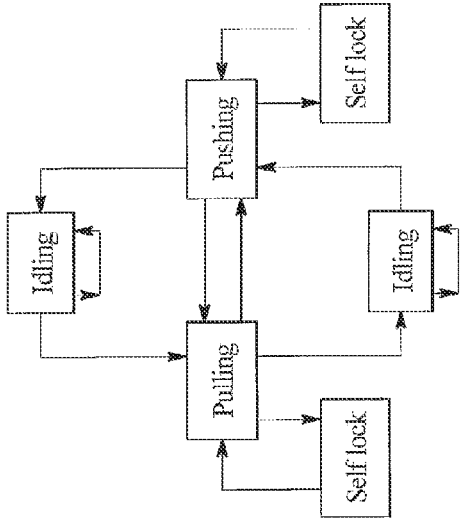

FIG. 22

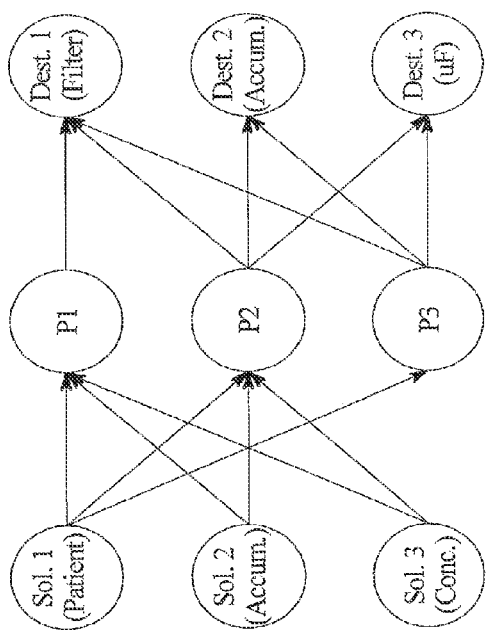

1. If from Solution 1 to Destination 1, then use Pump 1, Pump 2 or Pump 3.
2. If from Solution 2 to Destination 1, then use Pump 1 or Pump 2.
3. If from Solution 3 to Destination 1, then use Pump 1 or Pump 2.
4. If from Solution 1 to Destination 2, then use Pump 2 or Pump 3.
5. If from Solution 1 to Destination 3, then use Pump 2 or Pump 3.
6. If from Solution 3 to Destination 2, then use Pump 2.
7. No pumping from Solution 2 to Destination 2.
8. No pumping from Solution 2 to Destination 3.
9. No pumping from Solution 3 to Destination 3.
10. If any pump is pulling from Solution 2/3, no other pump can pull from Solution 3/2, respectively.
11. If any pump is pushing to Destination 2/3, no other pump can push to Destination 3/2, respectively.
12. Each pump pulls fluid from one solution at one time.
13. Each pump pushes fluid to one destination at a time.

FIG. 27

Pump Scheduling Inputs - Total Therapy       272

Stroke Volume =                              10.0 ml
Therapy Time =                               480.0 min
Dialysate Flow Rate =                        250.0 ml/min
Concentrate Add Flow Rate =                  5.0 ml/min
uF Removal Flow Rate =                       2.0 ml/min
Patient uF Generate Flow Rate =              2.0 ml/min
R = Dialysate Flow Rate/Accumulator Flow Rate = 3.0

FIG. 28

CycleTime =                      TherapyTime/NumberofCycles                                          274
StrokeTime =                     StrokeVolume *60/DialysateFlowRate
FromPatientCycleStrokes =        CycleTime*60.0/StrokeTime;
AccumulatorFlowRate =            DialysateFlowRate/R
To/FromAccumulatorCycleStrokes = CycleTime*AccumulatorFlowRate/StrokeVolume;
FromConcentrationCycleStrokes =  CycleTime*ConcentrateAddFlowRate/StrokeVolume;
To uFCycleStrokes =              CycleTime*(uFRemovalFlowRate+ConcentrateAddFlowRate)/StrokeVolume;

FIG. 29

| Pump Scheduling Outputs - Total Therapy | |
|---|---|
| Stroke Time = | 2.4 sec |
| From Patient Stroke Number = | 12000 |
| To/From Accumulator Stroke Number = | 4000 |
| From Concentrate Stroke Number = | 240 |
| To uF Stroke Number = | 336 |
| Pump Scheduling Outputs - Cycle of 10 Minutes | |
| From Patient Cycle Stroke Number = | 250 |
| To/From Accumulator Cycle Stroke Number = | 83 |
| From Concentrate Cycle Stroke Number = | 5 |
| To uF Cycle Stroke Number = | 7 |
| To Cartridge Cycle Stroke Number = | 248 |
| Total Fill Stroke Number = | 338 |

| From Patient Pumping | To Cartridge Pumping | From Accum. Pumping | To Accum. Pumping | From Conc. Pumping | To uF Pumping |
|---|---|---|---|---|---|
| P2 |  |  |  | P1 | P3 |
| P3 | P1 |  | P2 |  |  |
| P1 | P3 |  |  |  |  |
| P3 | P1 |  |  |  |  |
| P2 | P3 | P1 |  |  |  |
| P3 | P1 |  | P2 |  |  |
| P2 | P3 | P1 |  |  |  |
| P3 | P1 |  | P2 |  |  |
| P1 | P3 |  |  |  |  |
| P3 | P1 |  |  |  |  |
| P2 | P3 | P1 |  |  |  |
| P3 | P1 |  | P2 |  |  |
| P2 | P3 | P1 |  |  |  |
| P3 | P1 |  | P2 |  |  |
| P1 | P3 |  |  |  |  |
| P3 | P1 |  |  |  |  |
| P2 | P3 | P1 |  |  |  |
| P3 | P1 |  | P2 |  |  |
| P2 | P3 | P1 |  |  |  |
| P3 | P1 |  | P2 |  |  |
| P1 | P3 |  |  |  |  |
| P3 | P1 |  |  |  |  |
| P2 | P3 | P1 |  |  |  |
| P3 | P1 |  | P2 |  |  |
| P2 | P3 | P1 |  |  |  |

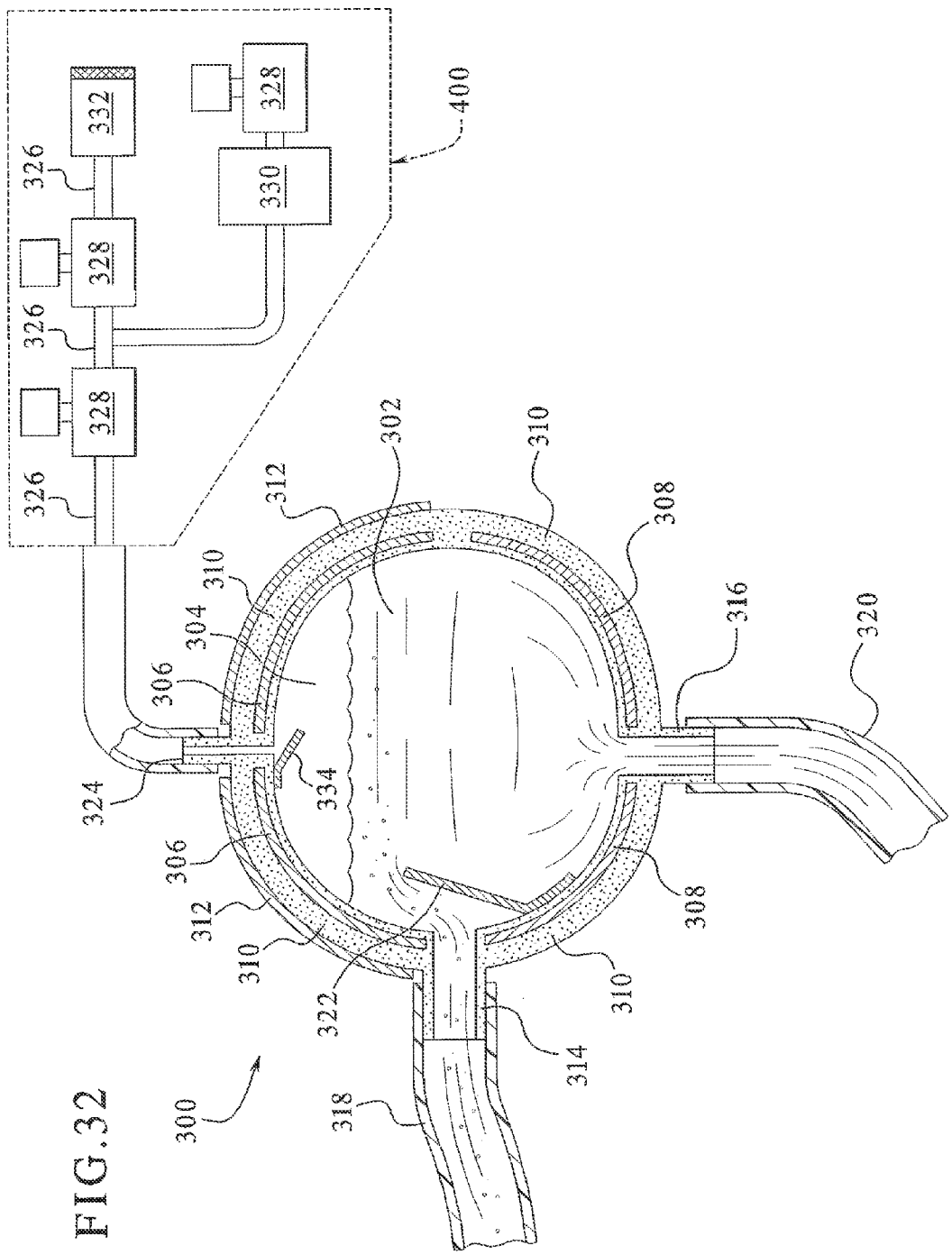

PUMPING SYSTEMS FOR CASSETTE-BASED DIALYSIS

PRIORITY

This application claims priority to and the benefit as a divisional application of U.S. Patent Application entitled Pumping Systems for Cassette-Based Dialysis", Ser. No. 13/528,502, filed Jun. 20, 2012, which claims priority to and the benefit as a continuation application of U.S. Patent Application entitled "Pumping Systems For Cassette-Based Dialysis", Ser. No. 11/773,148, filed Jul. 3, 2007, now U.S. Pat. No. 8,206,338, issued Jun. 26, 2012, which claims priority to and the benefit as a continuation application of U.S. Patent Application entitled "System Including Machine Interface For Pumping Cassette-Based Therapies", Ser. No. 11/617,527, filed Dec. 28, 2006, now U.S. Pat. No. 7,867,189, issued Jan. 11, 2011, which claims priority to and the benefit as a continuation application of U.S. Patent Application entitled "System Including Machine Interface For Pumping Cassette-Based Therapies", Ser. No. 10/335,646, filed Dec. 31, 2002, now U.S. Pat. No. 7,238,164, issued Jul. 3, 2007, which claims priority to and the benefit of U.S. Provisional Application Ser. Nos. 60/397,045 and 60/397,268, filed Jul. 19, 2002.

BACKGROUND OF THE INVENTION

The present invention generally relates to medical fluid systems. More specifically, the present invention relates to systems and methods of performing cassette-based dialysis and devices related thereto.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Peritoneal dialysis uses a dialysis solution or "dialysate", which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), including tidal flow APD and continuous flow peritoneal dialysis ("CFPD"). CAPD is a manual dialysis treatment. The patient connects manually an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from the dialysate source, through the catheter, into the patient's peritoneal cavity and allow the dialysate to dwell within the cavity and the transfer of waste, toxins and excess water to take place. APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all the fluid from the patient over a longer period of time, a portion of the fluid is removed and replaced after smaller increments of time.

Continuous flow or CFPD systems clean or regenerate spent dialysate instead of discarding it. The systems flow fluid into or out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are more complicated typically than batch systems.

Hemodialysis, APD (including tidal flow) and CFPD systems can employ a pumping cassette. The pumping cassette typically includes a flexible membrane that is moved mechanically to push and pull dialysis fluid out of and into, respectively, the cassette. Certain known systems include flexible sheeting on one side of the cassette, while others include sheeting on both sides of the cassette. Positive and/or negative pressure can be used to operate the pumping cassettes.

One problem with the pumping cassettes is leakage. If the flexible membranes experience a pinhole or tear, fluid and air can move from one side of the membrane to the other. Movement of fluid from inside the cassette to the inner workings of the machine can damage the machine. Movement of air from the machine into the cassette can compromise the sterility of the fluid pathways defined by the cassette. There are detection systems that determine when fluid leaks from the cassette to the machine. It is more difficult, however, to detect fluid leaking into the cassette.

Another problem with cassette-based pumping occurs when the cassette is loaded improperly into the machine. Proper alignment is important because portions of the flexible membrane must match corresponding machine portions, e.g., pump and valve actuators. Improper loading can lead to undue mechanical stress being placed on the cassette, harming potentially the cassette and/or the actuator. Improper cassette loading will also likely degrade or prohibit performance of the system.

A further dilemma, especially in CFPD, is the coordination of multiple fluid delivery. Cassette-based peritoneal pumping systems that administer fluids continuously to patients are required to withdraw fluid (ultrafiltrate) from and add fluid (concentrate) to a continuously flowing dialysis fluid loop. The additional fluids have typically necessitated additional dedicated pumps, which make the cassette and dialysis machine larger and noisier. Scheduling the operation of multiple pumps also presents a challenge to system implementers.

Another problem associated with cassette-based pumping is the entrapment of air or other gas into the fluid pathways. Air can enter the system via leaking connections, improper priming, faulty tubing and faulty cassettes. Patient therapy also produces various gases that enter the system. Cassette-based pumps are designed to pump fluid, not gas. Moreover, the removal and delivery of fluid from and to the patient needs to be monitored and controlled. Air and gases upset volume measurement systems that assume no air or gas exists in the fluid pathways. Air and gases can also be uncomfortable for the patient and impede proper waste removal.

It is desirable to remove air and gas from the dialysis fluid before the fluid enters the patient. To this end, cassette-based systems have been provided with air or gas vents. A need continues however to provide for more economical venting systems. Further, prior to infusion, the dialysis fluid solution is heated to body temperature, releasing gas from the solution. Known vents do not vent air or gas due to fluid heating. It is also desirable to have a method for detecting air and fluid, so that the volume of both can measured, detecting air for purging and detecting fluid for ensuring proper therapy.

SUMMARY OF THE INVENTION

In general, the present invention relates to medical fluid delivery systems that employ a pumping cassette. In particular, the present invention provides systems, methods and apparatuses for cassette-based dialysis therapies including hemodialysis, CAPD, APD (including tidal modalities) and CFPD, as these therapies have been described above.

In one embodiment, the systems, methods and apparatuses of the present invention are used with CFPD. The CFPD therapy includes, generally, a fluid circuit or loop connected to a patient, allowing dialysate or other suitable therapy fluid to be circulated into, through and out of the patient's peritoneal cavity to remove a therapeutic effective amount of excess water and solutes, such as uremic toxins, urea, creatinine and the like.

In an embodiment, the dialysate is continuously circulated along the fluid loop multiple times prior to discharge. The volume of dialysate consumed is minimized with respect to batch systems. The circulation can take the form of a single pass or multiple passes. One single pass system operable with the cassette-based systems, methods and apparatuses of the present invention is described in document Ser. No. 10/623, 317. One multiple pass system operable with the cassette-based systems, methods and apparatuses of the present invention is described in document Ser. No. 10/624,150.

As discussed above, the present invention is not limited to CFPD. One APD system operable with the cassette-based systems, methods and apparatuses of the present invention is described in U.S. patent application Ser. No. 10/155,603, Publication No. 20030220598, published Nov. 27, 2003, entitled, "Automated Dialysis System," the teachings of which are incorporated herein by reference. With these types of dialysis systems in mind, some of the various embodiments of the present invention are hereafter summarized.

In one embodiment, the present invention provides an actuator assembly that operates with the disposable cassette. The assembly includes a housing that holds both the pump actuators and the valve actuators. The pump/valve manifold eliminates the need for separate valve manifolds. This in turn reduces significantly the amount of tubing and tubing connections that would otherwise have to be made between one or more valve manifolds and a pump actuator housing. The combination pump/valve manifold also conserves space and materials, allowing for a smaller, lighter and more cost effective dialysis machine.

In another embodiment of the present invention, a fail safe valve and pump arrangement is provided. The arrangement allows fluid to flow only from the cassette into the machine in the event of a cassette failure. A positive pressure gradient is maintained from the cassette to the machine, generally preventing air from entering the cassette. The arrangement also ensures that all valves close in the event of a system failure or power failure, preventing fluid from mixing across fluid pathways in the cassette.

The arrangement includes a disposable cassette operable with one or more diaphragm pump chambers, one or more diaphragm valve seats and one or more fluid pathways. The cassette is constructed of a rigid or semi-rigid body portion (referred to collectively herein as "rigid portion") having flexible sheeting sealed to one or both sides of the portion. The cassette with sheeting is mated with at least one pump and at least one valve driver mechanism, creating an interconnected fluidics system.

During operation, a vacuum is normally maintained between the cassette sheeting and the pump/valve driver interface wherever a pump, valve, or fluid pathway is created. This creates a positive pressure gradient from the cassette to the components of the dialysis machine. The valve plungers press the sheeting against the rigid portion of the cassette, closing the valves unless a vacuum (or pressure) is provided to mechanisms that retract the valve plungers.

The pump actuators may be configured to extend, retract or hold position in the event of system failure and include a piston having a piston head. The piston head pushes against a flexible membrane of the disposable cassette to dispel fluid from the cassette. Various actuators are provided to move the piston heads. One actuator, for example, includes a first or deep vacuum that draws the piston head away from the cassette and a second shallow vacuum that pulls the membrane away from the cassette, causing dialysis fluid to enter the cassette. In an embodiment, a spring cavity is located on the end of the piston opposite the piston head. The spring cavity houses a spring, which when the deep vacuum is not present, pushes the piston, piston head and cassette sheet into the rigid portion of the cassette. When the deep vacuum is applied, the deep vacuum overcomes the compression resistance of the spring and compresses the spring.

To separate the deep and shallow vacuums, a rolling diaphragm is sealed to the pump piston and the walls of the spring housing. The rolling diaphragm includes enough take-up material to allow the piston to move back and forth. To ensure that the take-up material of the diaphragm rolls or moves properly, a shallow vacuum is left in the spring housing (i.e., in place of the deep vacuum) when the deep vacuum is removed. The shallow vacuum is not strong enough to overcome the compression resistance of the spring but is strong enough to keep the rolling diaphragm from inverting due to the shallow vacuum maintained around the piston head that seals the membrane to the piston head. Alternatively, multiple rolling diaphragms are used, with atmospheric air applied between the diaphragms.

One alternative valve actuator replaces the diaphragm with a piston-cylinder, which is activated via negative or positive pressure. Another alternative valve actuator replaces the diaphragm, spring and deep vacuum altogether with an electrically operated actuator, such as a stepper motor (linear or rotary), servo motor or other type of linear actuator. A shallow vacuum is still applied to seal the cassette membrane to the piston head.

A fail safe valve is also provided, which makes use of the deep and shallow vacuum in an embodiment. The valve utilizes a spring and negative pressure to operate a valve plunger that contacts the flexible membrane of the disposable cassette. The valve also seals to a moveable diaphragm that separates different vacuums. A deep vacuum is applied to compress the spring, moving the valve plunger away from the cassette. A shallow vacuum is applied to the opposite side of the diaphragm from the spring housing and causes the flexible membrane of the cassette to move with the valve plunger. The shallow vacuum also aids the spring to push the plunger against the flexible membrane, increasing the valve sealing force. The deep vacuum is strong enough therefore to overcome the spring's compression resistance and the shallow vacuum.

In a further embodiment of the present invention, a method and apparatus for automatically aligning the disposable cassette within the machine is provided. The procedure attempts to correct smaller misalignments, sends an error for larger misalignments, helps to ensure cassette quality and provides cassette integrity testing.

The method includes loading the cassette into the dialysis machine and, before inflating a sealing bladder, moving one or more pump piston towards a respective pump cavity. This action causes the cassette to shift, if need be, into its proper position. If a resistance to the movement of the piston(s) is detected, the dialysis machine knows that a problem has occurred either with the cassette or the mechanics of the machine and can take action appropriately. The procedure is operable whether the cassette loads horizontally on top of the machine, or vertically on a side of the machine.

After the alignment procedure takes place, a bladder inflates and compresses the cassette against an inner surface of the dialysis machine, the pump pistons and valve plungers. The cassette is then ready for use. A sensor is also provided, such as a strain gauge, which monitors the force exerted by the moving pistons on the cassette. If the disposable cassette is out of alignment to the point that alignment cannot be corrected, the sensor detects the undue stress placed on the piston head, sends an error message and de-energizes the pumps.

In yet another embodiment of the present invention, a material for the flexible membrane is provided. The material is fabricated from a non-PVC containing, thermoplastic polymeric material and can be of a monolayer structure or a multiple layer structure. The film can be fabricated using standard thermoplastic processing techniques such as extrusion, coextrusion, extrusion lamination, lamination, blown extrusion, tubular extrusion, cast extrusion or coextrusion, compression molding and thermoforming.

In still a further embodiment of the present invention, a valve arrangement is provided that allows different fluids to be combined and removed from a medical fluid system. The valve arrangement is operable with a single pump or multiple fluid pumps. The arrangement is described in connection with CFPD but is operable with other types of dialysis. In the illustrated embodiment, the arrangement allows concentrate to be added and ultrafiltrate to be withdrawn from a dialysis fluid in a continuous or semi-continuous manner, without requiring additional fluid pumps.

The valve arrangement adds an additional inlet valve and outlet valve for each pump. To this end, each pump operates with a main intake valve that provides on/off control for the inlet flow of dialysate in a continuous loop (CFPD) or from a supply bag (APD). A second intake valve operates in parallel with the main intake valve and provides on/off control for a concentrate or additive (CFPD) or parallel dialysate supply (APD). Each pump operates with a main exhaust valve that provides on/off control for the outlet flow of dialysate, e.g., to the patient. A second exhaust valve operates in parallel with the main outlet valve and provides on/off control for, e.g., the removal of ultrafiltrate from the dialysis fluid.

When the second intake and exhaust valves are open, the main valves are closed and vice versa in an embodiment. The relevant amount of time that the main versus the second valves are open determines how quickly concentrate is added or ultrafiltrate is removed. For instance one pump volume's worth of concentrate can be pumped once every thirty-three pump strokes or once every five-hundred pump strokes.

In one implementation, a pair of multiplexed pumps is provided, yielding alternating and virtually continuous flow of fluid to the patient. In this implementation, a number of variations arise. For example, the secondary intake valves or the secondary exhaust valves can be opened simultaneously, doubling concentrate intake or ultrafiltrate removal. Still further, partial fills can be employed via the second valves by only partially moving the pump piston.

In still a further embodiment of the present invention, an expert system and method for scheduling the pumping of one or more solutions, via one or more pumps and to one or more destinations is provided. The system and method are illustrated with respect to CFPD but are also applicable to APD and hemodialysis. The expert system uses a set of rules. The rules are derived from physical limitations, e.g., fluid flow connections and pumping state limitations. The rules are also derived from therapy limitations, e.g., it is undesirable to pump concentrate directly to ultrafiltrate collection, and arbitrary limitations, e.g., no partial pump strokes.

The expert system also accounts for a number of parameters inputted by the patient or doctor. The system applies various algorithms to the inputted values to yield the output requirements for the therapy, e.g., overall flow volume, flowrate, therapy time, total concentrate added, etc. Using the outputs and the rules or restrictions, the expert system develops a pumping schedule having a number of entries. Each entry directs one or more pump to pull or push from one or more solution or to one or more destination, respectively. The controller of the system commands the pumps to execute the pumping profile set forth in the schedule. The schedule may represent a portion of the overall therapy, wherein the schedule is cycled a number of times until therapy is complete. In the end, the outputs are achieved according to the rules and other limitations, such as fluid pressure level limitations.

In yet another embodiment of the present invention, a port vent for venting air purged from the dialysis fluid is provided. The port vent is integral to the cassette and vents the priming volume as well as air entrained due to pumping and patient exhaust gases. The cassette-based port vent is molded integrally with the rigid portion of the cassette, taking advantage of the fact that the rigid portion is otherwise a molded structure. A filter, such as a 0.2 micron filter is then fixed, e.g., bonded, heat sealed, adhered or mechanically fixed, to the port vent. The filter is made of a material, such as PTFE, Gortex or other polymer, which can be bonded, heat sealed, adhered or fixed mechanically. In an embodiment, the filter is made of a hydrophobic material. Alternatively, the filter is bonded, heat sealed, adhered or fixed to a bushing that fits onto and is suitably attached to the molded port.

Moreover, in an embodiment an additional air separation chamber for a medical fluid system is provided. The cassette-based port vent provides a first venting mechanism that separates air entrained in the fluid at the point of pumping. After the dialysis fluid leaves the pumping cassette, however, the fluid passes through a heater. The addition of heat releases gas trapped in the solution. This additional released gas must also be purged before the solution enters the patient.

The additional gas separation chamber is located downstream from the fluid heater. The heat released gas rises to and is trapped at the top of the chamber, while the heated fluid passes through the bottom of the chamber. The chamber houses one or more capacitive sensors that detect the amount of gas in the chamber. When the amount reaches a predetermined level, one or more exhaust valve opens and allows the gas to vent.

The gases vent through a membrane. To keep the membrane dry, a series of exhaust valves may be employed. To this end, a sump fluid trap may alternatively or additionally be provided.

In still another embodiment, a gas separation device is provided that includes a series of valves that are operated sequentially. A fluid trap is provided in between the valves. The sequential operation of the valves and trap enables gas but not fluid to escape from the system.

In consideration of the embodiments described herein, it is therefore an advantage of the present invention to provide a cassette actuator assembly that houses both the pump and valve actuators.

Another advantage of the present invention is to provide a cassette-based medical fluid system having fail safe valve and pump actuation.

A further advantage of the present invention is to provide a cassette-based medical fluid system having a positive pressure gradient between the cassette fluid pathways and the outlying components of the dialysis machine.

Still another advantage of the present invention is to provide a cassette-based medical fluid system having a cassette auto-alignment feature.

Yet another advantage of the present invention is to provide a cassette-based medical fluid system having a cassette misalignment output and a cassette integrity feature.

Moreover, an advantage of the present invention is to provide an improved material for the flexible membrane of the cassette.

Still further, an advantage of the present invention is to provide a cassette-based medical fluid system having a multiplexing valve arrangement.

Further still, an advantage of the present invention is to provide a cassette-based medical fluid system having an expert fluid pumping management system that uses a knowledge base to derive a pumping schedule after parameters are inputted by a doctor/patient.

Still a further advantage of the present invention is to provide a cassette-based integrally formed port vent.

Yet a further advantage of the present invention is to provide an air separation chamber downstream of a medical fluid heater.

Moreover, a further advantage of the present invention is to allow the dialysis fluid to purge entrained gas while the fluid is being pumped.

Additional features and advantages of the present invention are described in, and will be apparent from, the following Detailed Description of the Invention and the figures.

BRIEF DESCRIPTION OF THE FIGURES

FIGS. 10 and 11 are sectioned elevation views of one embodiment of a pneumatically and mechanically actuated valve of the present invention.

FIGS. 13 and 14 are sectioned elevation views taken through lines XIII-XIII and XIV-XIV, respectively, in FIG. 12 illustrating the cassette auto-alignment feature of the present invention.

FIGS. 17 to 20 illustrate an embodiment for a valve arrangement of the present invention allowing multiple fluids to be pumped into and out of the same fluid pump chamber.

FIG. 21 is a schematic process flow diagram illustrating various fluid flow connections between a plurality of solutions, a plurality of pumps and a plurality of fluid destinations for an expert pumping system of the present invention.

FIG. 22 is a diagram that illustrating schematically the possible states of the fluid pumps for the expert pumping system of the present invention.

FIG. 23 is a sample list of software rules implemented to control the flow for the expert pumping system of the present invention.

FIGS. 27 to 29 illustrate various inputs, outputs and algorithms used by the expert pumping system of the present invention to output a fluid flow schedule illustrated in FIG. 30.

FIG. 30 is a table showing a portion of a fluid flow schedule of the expert pumping system and method of the present invention, the schedule organizing the flow of fluid from various pumps to achieve desired flow rates and volumes of various fluids to various destinations over a desired period of time.

FIG. 32 is a sectioned elevation view of one embodiment of an air separation chamber using capacitance fluid volume sensing.

DETAILED DESCRIPTION OF THE INVENTION

The present invention relates to cassette based medical fluid delivery systems. In particular, the present invention provides various improvements to the cassette and components operating with the cassette, in fluid communication with the cassette or in connection with managing the flow of fluids through the cassette in complex systems having a multitude of fluid sources, a multitude of fluid pumps and a multitude of fluid destinations. These improvements are particularly well suited therefore for CFPD, which is typically more complex than other forms of dialysis treatment. It is expressly contemplated however that the embodiments set forth are not limited to CFPD and are operable with APD (including tidal flow systems), hemodialysis, hemofiltration and any combination thereof.

I. Combined Pump and Valve Housing

Figure 1:
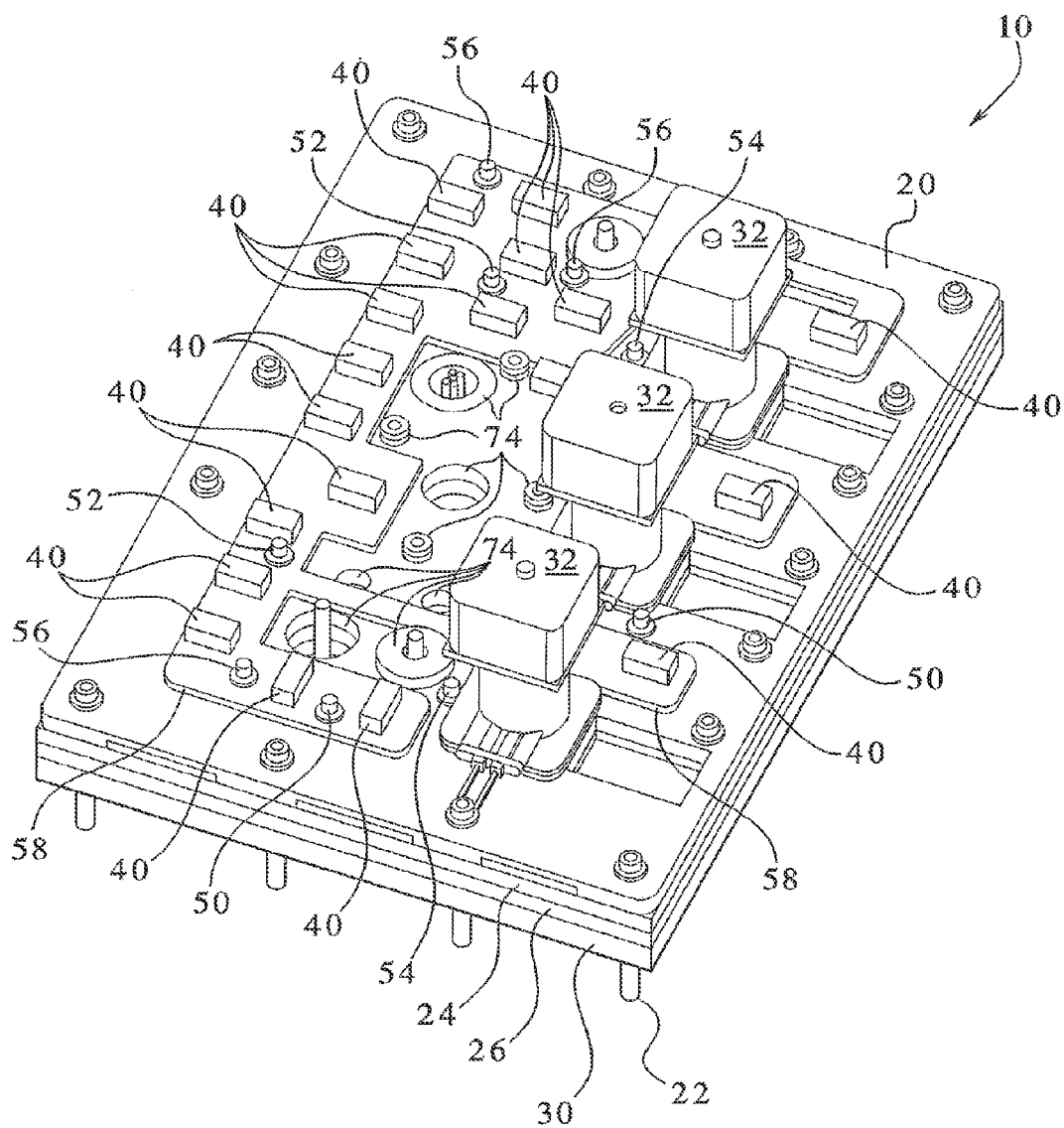
FIGS. 1 and 2 illustrate opposing views of an embodiment of a value and pump actuation assembly having a value/pump housing that houses in combination a valve manifold and a plurality of pump actuators.
Figure 2:
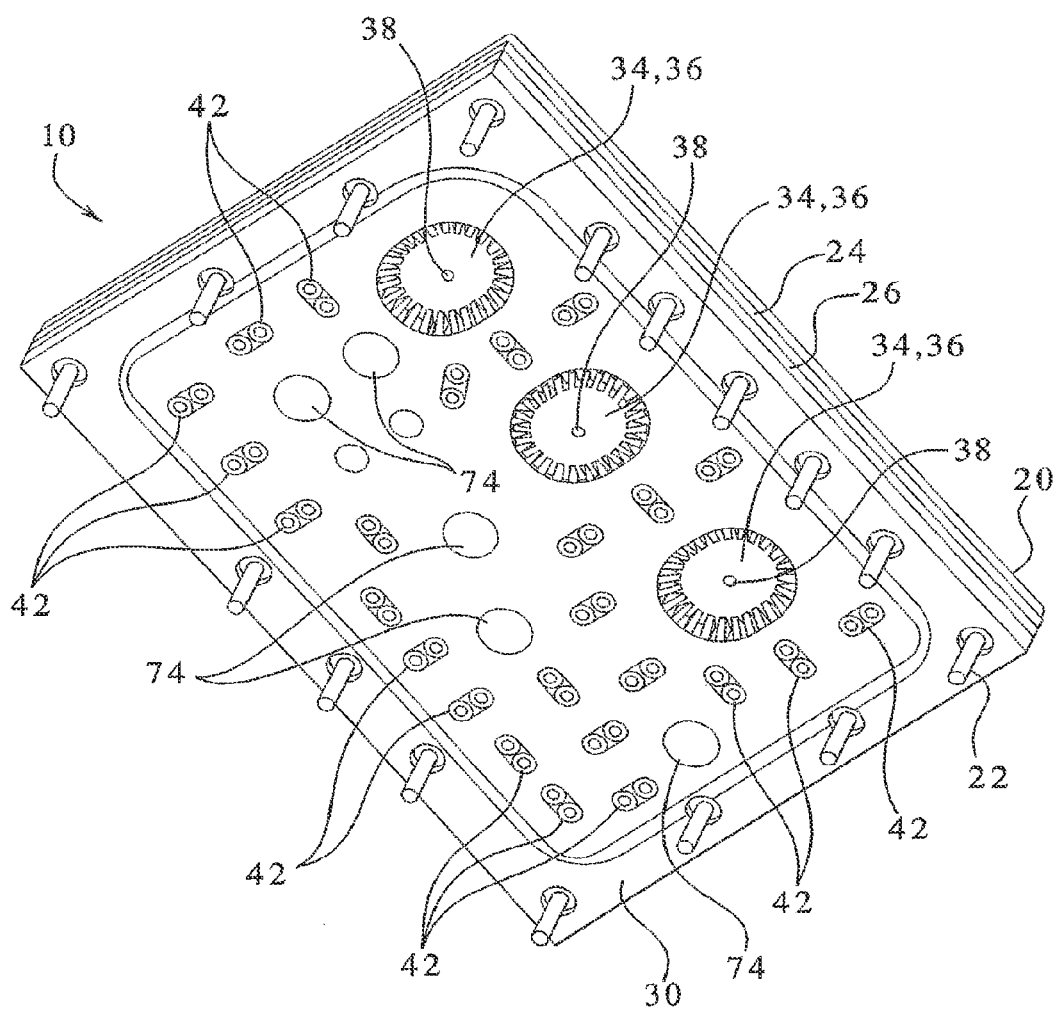

Referring now to the drawings and in particular to FIGS. 1 to 5, a combination valve manifold and pump housing assembly 10 is illustrated. FIGS. 1 and 2 illustrate that assembly 10 includes a number of components, including a valve/pump housing 20, a number of intermediate plates 24 and 26 and a front plate 30. Assembly 10 in other embodiments can have less or more than four components depending upon the complexity of the medical fluid system, for example, depending on the number and type of pumps and the number and type of fluid valves.

Figure 12:
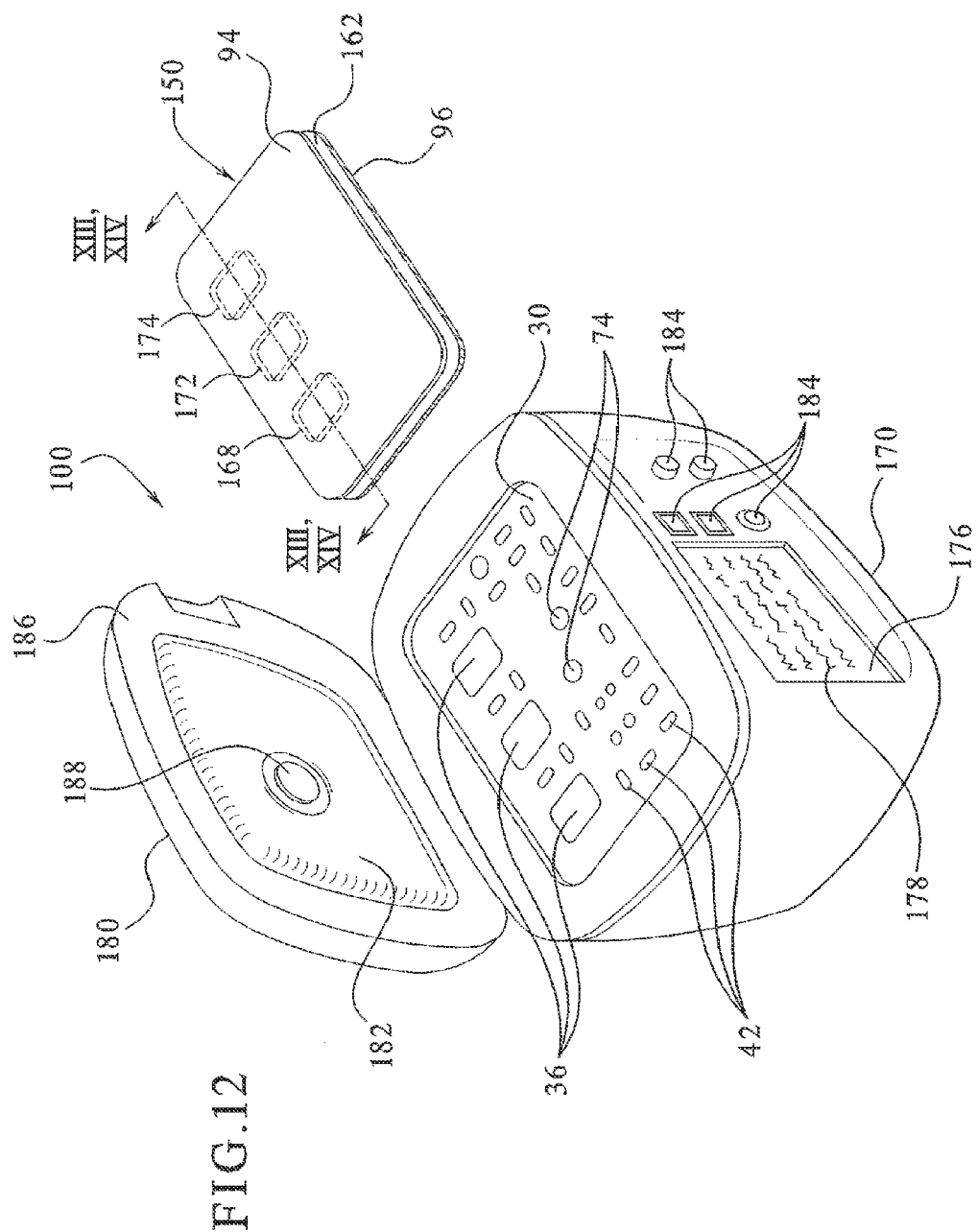
FIG. 12 is a perspective view of a dialysis hardware machine showing the loading of a disposable cassette and an embodiment of an auto-alignment feature of the present invention.

The assembly 10 is housed inside of an automated peritoneal dialysis machine, wherein the valve/pump housing 20 and the components mounted to the housing face inward towards the center of the machine. The front plate 30 faces upward and outward toward the disposable cassette (see FIG. 12 showing machine 100 and cassette 150). A number of bolts or other type of fastening devices 22 hold housing 20, intermediate plates 24 and 26 and front plate 30 together. Mounting devices 22 can also bolt assembly 10 to the dialysis machine in an embodiment.

A gasket may also be placed between any mating component, such as between the valve/pump housing 20 and intermediate plate 24, between intermediate plates 24 and 26 and/or between intermediate plate 26 and front plate 30. As illustrated below in connection with FIGS. 6, 7 and 9 to 11, one or more vacuum chambers are used in various embodiments in connection with the valves and the pumps of the present invention. A portion of the vacuum chambers is defined by apertures collectively made by one or more or all of the housing 20 and plates 24, 26 and 30, requiring an airtight seal between these components. In an embodiment, a negative pressure of about −2 to −20 psig. and preferably about −6 psig. to about −10 psig. is applied within the vacuum chambers. The gaskets between components 20, 24, 26 and 30 are selected and sized to withstand this level of vacuum.

Figure 6:
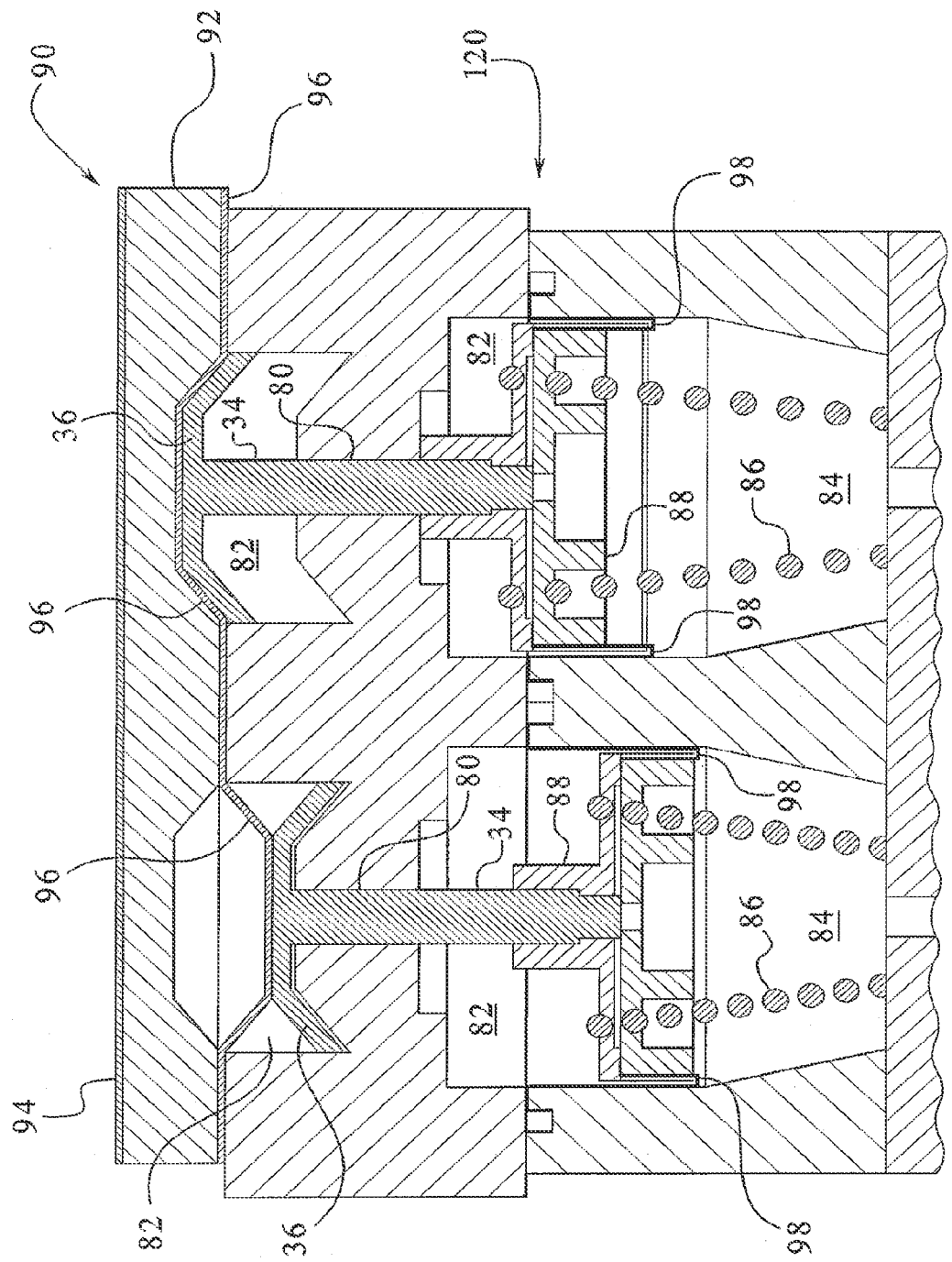
FIG. 6 is a sectioned elevation view of mechanically and pneumatically operated pumps of the present invention shown in combination with a fluid pumping cassette.
Figure 7:
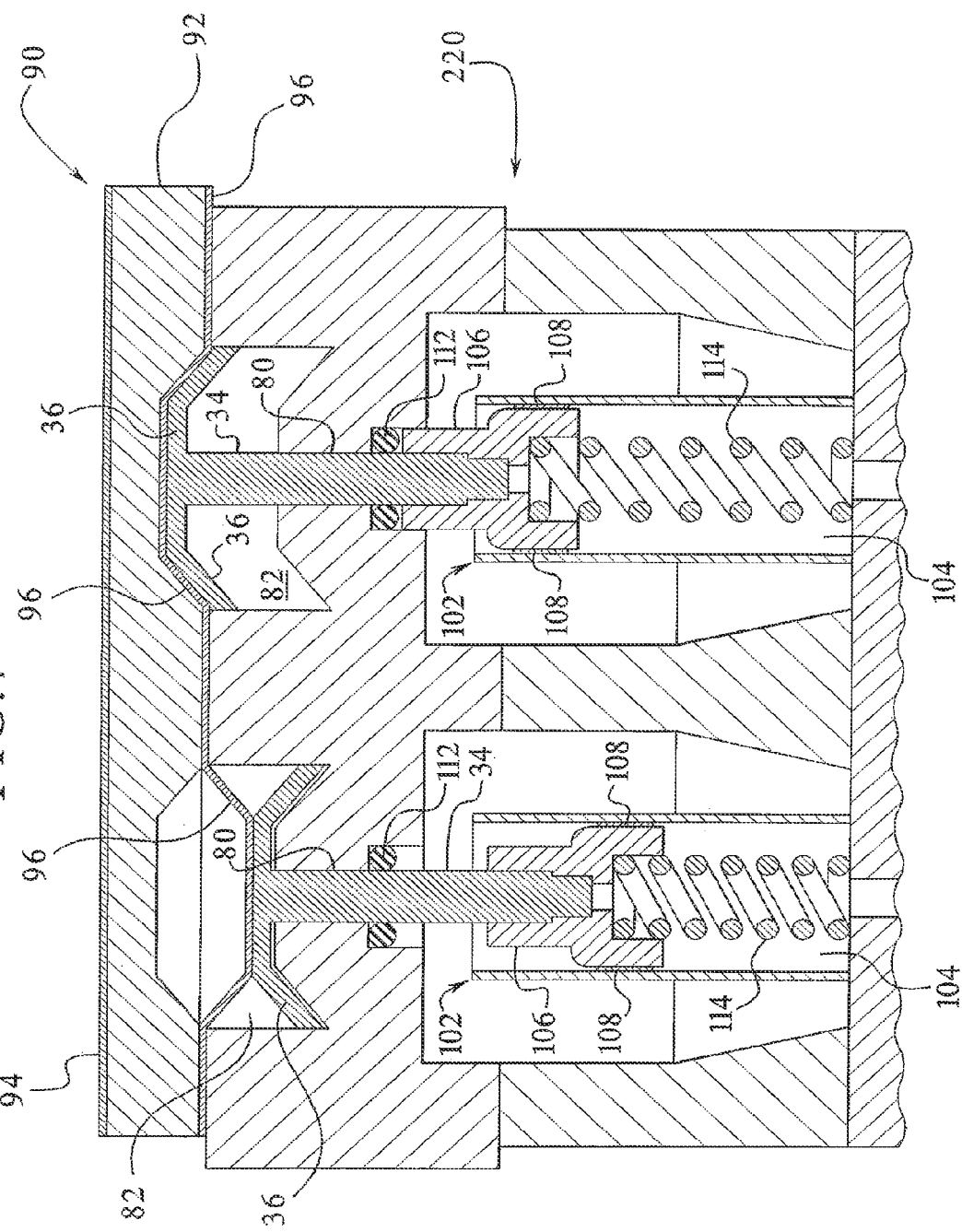
FIG. 7 is a sectioned elevation view of another embodiment of mechanically and pneumatically operated pumps of the present invention shown in combination with a fluid pumping cassette.

FIG. 1 illustrates that three pump actuators 32 mount to the valve/pump housing 20, however, alternative embodiments of the present invention may use one pump, two pumps or more than three pumps. Pump actuators 32 in an embodiment are linear motors, such as linear stepper motors made by Hayden Switch and Instrument Inc., Waterbury, Conn. FIGS. 6 and 7 illustrate that the pump actuators are alternatively springs. In further alternative embodiments, the pump actuators could be piston cylinders driven by positive or negative pressure, rotary motors in combination with a rotational to linear motion converter or other type of linear motion producing device.

As illustrated below, and as seen in FIG. 2 on front plate 30, the output of the pump actuator is a pump piston 34 having a pump piston head 36. Pump actuator 32 pulls piston heads 36 back from the face of front plate 30 towards valve/pump housing 20, pulling via a vacuum a flexible membrane of the disposable cassette (not shown), which in turn pulls dialysis fluid into the cassette. Pump actuators 32 push piston 34 and piston head 36 outward from the face of front plate 30, pushing on the flexible membrane in towards a rigid portion of the cassette to dispel fluid from the cassette. As illustrated in FIG. 2, the piston head 36 is in a retracted or pulled back position for the outer two pumps and is in a pushed forward position for the middle pump.

The pistons 34 and piston heads 36 each define a vacuum channel 38 in an embodiment. Vacuum channels 38 allow a vacuum applied beneath front plate 30 to communicate fluidly through the piston 34 and piston head 36 with the flexible membrane of the disposable cassette. Alternatively, the vacuum extends around the piston head 36, which is disposed in a vacuum chamber, to seal the membrane to piston head 36.

A plurality of valves 40 also mount to the valve/pump housing 20 as illustrated by FIG. 1. Valves 40 are actuated electrically in an embodiment, however, valves 40 can be pneumatically operated in an alternative embodiment. FIG. 2 illustrates that a valve plunger 42 is operable with each of the valves 40. As illustrated in more detail below in connection with FIGS. 10 and 11, valve plungers 42 are pressed mechanically against the flexible membrane of the disposable cassette, for instance by a spring. The valve plungers are retracted away from the flexible membrane of the disposable cassette via negative pressure facilitated by valves 40.

Valve plungers 42 also define vacuum orifices in an embodiment that enable a vacuum to pull the flexible membrane outward, i.e., to open a fluid flow path in the disposable cassette, when the valve plunger 42 is retracted or pulled inward from the face of plate 30. Plunger 42 is retracted when pneumatic valve 40 is energized, allowing the spring to see negative pressure, compressing the spring. The vacuum alternatively flows around the valve plunger to seal the membrane to the plunger 42.

Figure 3:
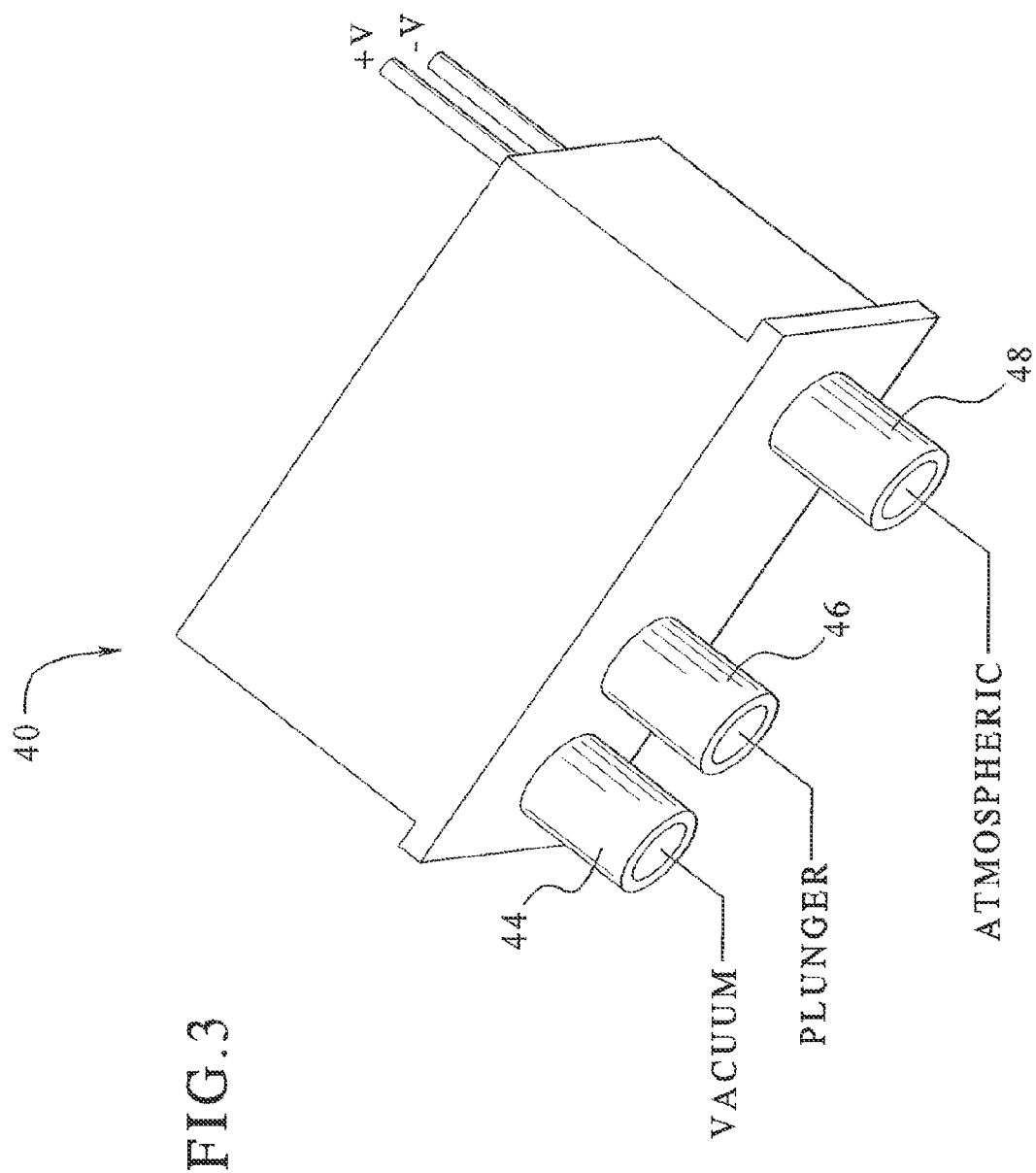
FIG. 3 is a perspective view of one embodiment of a valve actuator used in the present invention.

Referring now to FIG. 3, an embodiment of a pneumatic valve 40 is illustrated. Suitable three port valves are provided by Pneutronics, Inc. of Hollis, N.H., Fluid Automation Systems (FAS) of Versoix, Suisse, SMC Pneumatics and Lee Corporation.

Valve 40 has a housing defining a normally closed or vacuum port 44, a common or plunger port 46 and a normally open or atmospheric air port 48. The common port 46 connects fluidly to a vacuum chamber for operating the valve plunger 42, for example, vacuum chamber 144 illustrated in FIG. 10.

In an embodiment, an open fluid flow path exists when no voltage is supplied to electrical lines V+ and V− between the atmospheric air port 48 and the plunger port 46. Pneumatic valve 40 is therefore normally open between ports 46 and 48. When a voltage is placed across electrical lines V+ and V−, a solenoid within valve 40 is energized so that the fluid path across 46 and 48 is closed and so that a fluid pathway opens between vacuum port 44 and plunger port 46.

With valve 40, a fluid pathway in the cassette is opened when a voltage is applied to lines V+ and V−, for example, +−5 VDC or +−24VDC. Upon energizing, a vacuum supply evacuates air from a chamber defined by plunger port 46, an aperture defined by valve/pump housing 20, mating apertures in plates 24, 26 and 30, to activate a valve plunger 42 fitted within the vacuum chamber. A separate vacuum pulls the cassette membrane outward from the disposable cassette when the valve plunger 42 is retracted.

When the voltage is removed from electrical lines V+ and V−, the solenoid returns to its normal state. Atmospheric air is drawn into the vacuum chamber through ports 48 and 46, allowing a valve spring to push the valve plunger against the flexible membrane of the disposable cassette, closing the associated fluid pathway The valve springs are sized appropriately to provide the desired amount of sealing pressure. The spring force in an embodiment is between 0 and 10 lbs., and in one preferred embodiment about two to six lbs.

FIG. 1 illustrates that a plurality of different types of fluid connectors are attached to valve/pump housing 20. Connectors can be any type of tubing or piping connectors known to those of skill in the art, such as hose barbs, nut and ferrule type connectors, threaded connectors, quick disconnect type connectors, etc. Connectors 50 connect to negative pressure supply tubes that run to a source of negative pressure (not illustrated). Negative pressure connectors 50 connect fluidly to negative pressure supply channel 60 defined by surface 64 of housing 20 as illustrated in FIG. 4.

A plurality of atmospheric air inlet connectors 52 are also mounted to valve/pump housing 20. Atmospheric air connectors 52 attach to tubes that connect fluidly to one or more air filters. The filtered air runs through connectors 52 to an atmospheric air supply channel 62 defined by the valve/pump housing 20 illustrated in FIG. 4. Negative supply channel 60 feeds each of the vacuum ports 44 of the valve 40 (FIG. 3), while atmospheric air supply channel 62 feeds each of the atmospheric air ports 48 of the pneumatic valve 40. In an embodiment, to evenly distribute the vacuum, a negative pressure connector 50 is placed near each of the ends of the negative pressure channel 60, while the atmospheric air inlet connectors 52 are spaced suitably apart along the atmospheric air supply channel 62.

FIG. 1 illustrates that valve/pump housing 20 defines or is attached in an airtight manner to a raised bridge 58. Valves 40 and various ones of the connectors 50 and 52 mount to raised bridge 58. Raised bridge 58 allows the valve 40 to sit slightly above channels 60 and 62, so that ports 44 and 48 of the valve 40, respectively, can extend into channels 60 and 62. A suitable gasket may be placed about channels 60 and 62 between the surface 64 (FIG. 4) of housing 20 and bridge 58. Otherwise, bridge 58 is formed integrally with housing 20 or is permanently attached, e.g., welded, to housing 20.

Figure 4:
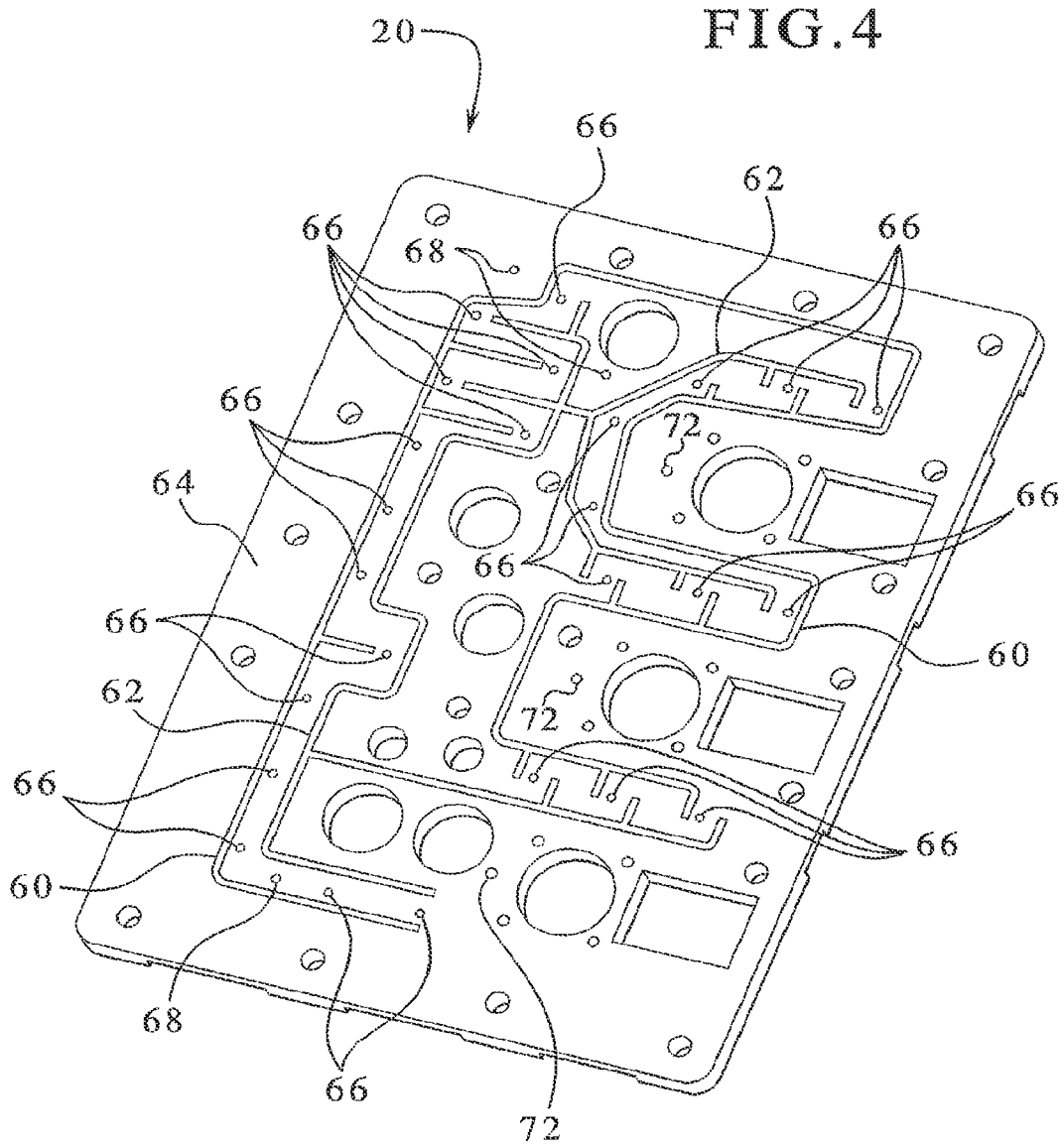
FIG. 4 is a perspective view of a surface of the valve/pump housing illustrated in FIG. 1 that remains after a portion of the housing is cutaway, the surface showing vacuum and atmospheric air flow paths.

FIG. 4 illustrates housing 20 with the bridge 58 removed, exposing channels 60 and 62 defined in surface 64. Removing bridge 58 also exposes various apertures defined by housing 20. For example, housing 20 defines a plunger aperture 66 for each pneumatic valve 40. The plunger port 46 of valve 40 (FIG. 3) extends into apertures 66. The gasket (not illustrated) surrounding channels 60 and 62 also surrounds each of the plunger apertures 66 in an embodiment. Plunger apertures 66 allow negative pressure or atmospheric air to extend from inner surface 64 of housing 20 to the valve plunger side of housing 20, illustrated in FIG. 5. It should be appreciated that the vacuum is supplied through connectors 50, through channel 60, through vacuum port 44, through plunger port 46, through plunger apertures 66 and through corresponding apertures defined by one or more of the plates 24 and 26 and front plate 30 to compress the plunger spring and open a fluid pathway in the disposable cassette. As illustrated below, the vacuum can also be bounded or housed in part by a flexible diaphragm, existing for example between two of the plates 24, 26 and 30.

Valve/pump housing 20 also defines valve sheeting apertures 68. Valve sheeting apertures 68 communicate fluidly with negative pressure connectors 56 illustrated in FIG. 1. Negative pressure connectors 56 communicate fluidly with a negative pressure source and enable a vacuum to be applied through the orifices of the valve plungers 42 (or around valve plungers 42) to the flexible membrane of the disposable cassette. The negative pressure source (not illustrated) pulls a vacuum through the connectors 56, through the valve sheeting apertures 68 and through the valve plungers 42 to seal the flexible membrane to the valve plungers.

Similar to the negative pressure for the valve sheet, valve/pump housing 20 defines, for each fluid pump, a pump sheeting aperture 72. Pump sheeting apertures 72 communicate fluidly with negative pressure inlet connectors 54, which in turn communicate fluidly with a negative pressure source (not illustrated). The negative pressure source pulls a vacuum through connectors 54, through apertures 72, through or around the piston 34 and piston head 36 to seal the flexible membrane of the disposable cassette to the piston head.

It should be appreciated that three separate vacuums in an embodiment are applied in connection with the valve/pump housing 20 of assembly 10. Namely, a first vacuum is applied to vacuum channel 60 defined by surface 64 of housing 20, a second vacuum is applied to seal the flexible membrane to the valve plungers and a third vacuum is applied to seal the flexible membrane to the pump piston heads 36. The fluid flow system can provide multiple vacuum sources that operate each of these vacuums separately. Alternatively, one or more sources operate these vacuums sequentially. Further alternatively, the level of vacuum is the same for two or more of the required vacuums, wherein a single vacuum source can supply at least two of the vacuums simultaneously.

FIGS. 1 and 2 illustrate that assembly 10, including valve/pump housing 20, houses various types of sensors 74. The various types of sensors include but are not limited to pressure sensors, temperature sensors, liquid level sensors, air detection sensors, bubble sensors, volume measurement sensors, conductivity sensors, pH sensors, turbidity sensors, color detection sensors, particle sensors, and chemical sensors, etc. As illustrated, sensors 74 extend through housing 20, intermediate plates, 24 and 26 and front plate 30. Sensor wiring and sensing leads extend into the dialysis machine from valve/pump housing 20. Sensing heads or sensor portions are located flush approximately with the face of front plate 30 and contact the disposable cassette to sense a fluid parameter of the dialysis fluid flowing through the cassette. A seal is made in an embodiment between the cassette and the front plate 30 around the sensors so that a vacuum can be applied, bringing the cassette membrane into intimate contact with the sensors. The vacuum is provided through assembly 10 around the sensors in a manner similar to that provided between the valve plungers 42 and the cassette membrane.

Figure 5:
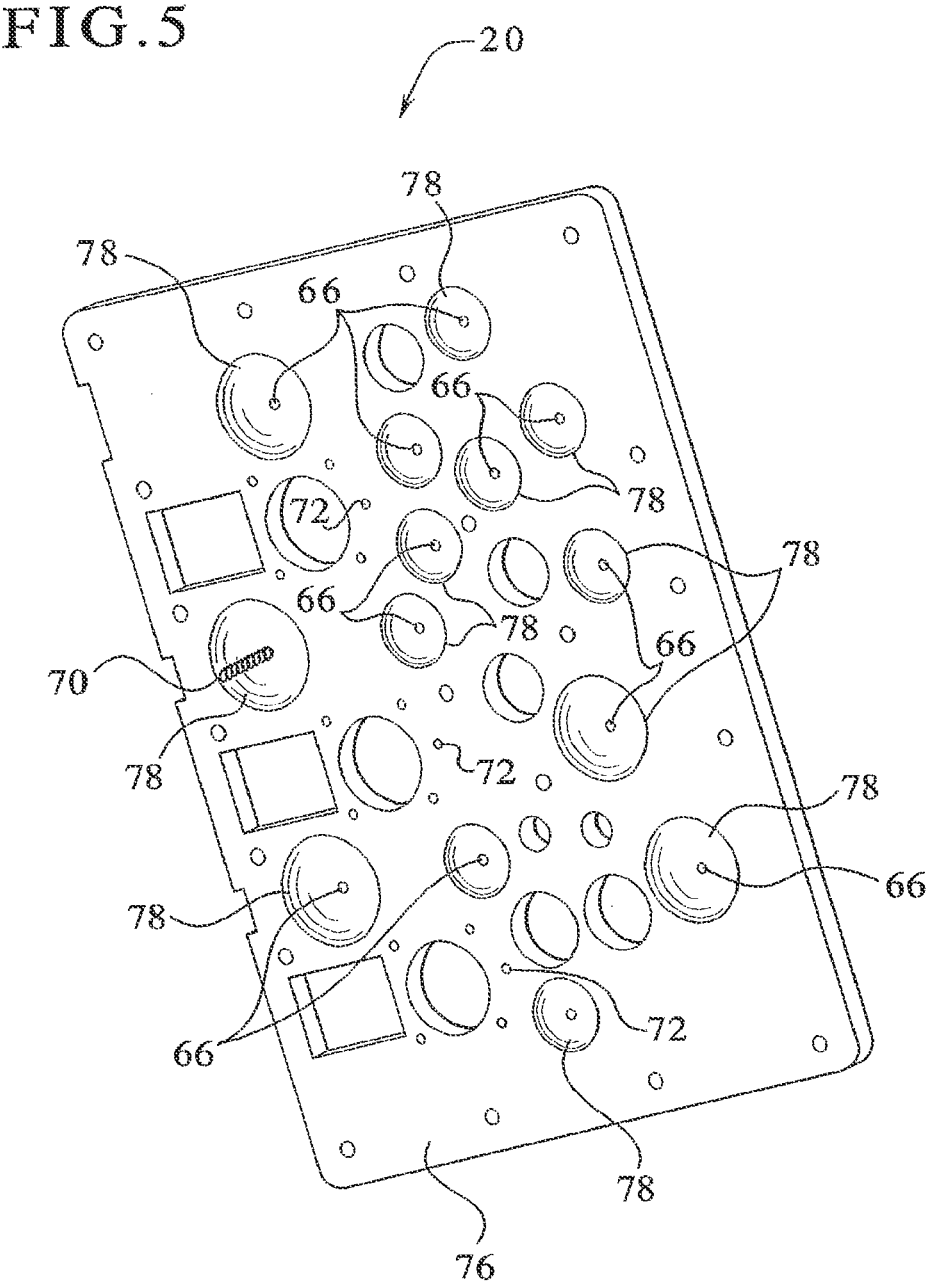
FIG. 5 is a perspective view of the opposing side of the valve/pump housing from the side illustrated in FIG. 4, the opposing side showing a plurality of valve plunger cavities.

Referring to FIG. 5, the valve/pump housing 20 is illustrated showing surface 76, which opposes surface 64 illustrated above in connection with FIG. 4. For reference, a majority of the plunger apertures 66 that communicate with the plunger port 46 of pneumatic valve 40 are illustrated, as are the pump sheeting apertures 72 that communicate fluidly with the negative pressure inlet connectors 54. At least some of the valve plunger apertures 66 are located in the middle of cavities or craters 78 defined by surface 76 of housing 20. Housing 20, defining cavities 78, is made in various embodiments of molded plastic or aluminum composite. Cavities or craters 78 enable the plungers and plunger seats (not illustrated) to situate properly with respect to plunger apertures 66. For reference, a plunger spring 70 is illustrated centered about an aperture 66, which in turn is centered in one of the cavities 78. Although not illustrated, it should be appreciated that the valve seats and valve plungers fit around spring 70 and sit inside or are supported by cavity 78.

II. Fail Safe Pump and Valve Operation

Figure 8:
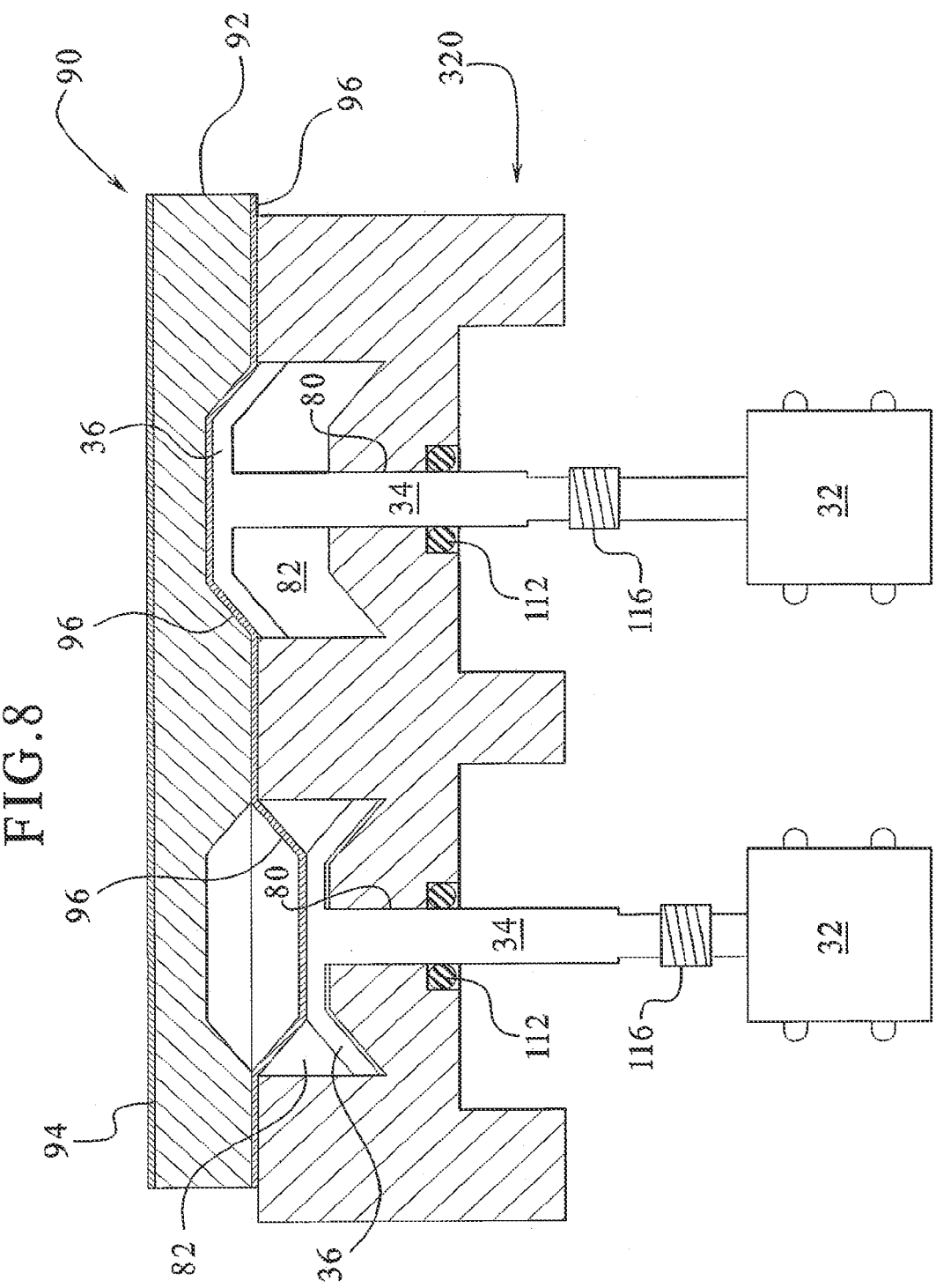
FIG. 8 is a sectioned elevation view of electrically operated pumps of the present invention connected operably to a fluid pumping cassette.

Referring now to FIGS. 6 to 11, various embodiments for operating the pumps and valves described above in connection with assembly 10 and valve/pump housing 20 are illustrated. FIGS. 1 to 5 illustrate an assembly 10, which includes a combination valve/pump housing 20 and adjoining plates 24, 26 and 30. The present invention is not however limited to the this configuration. FIGS. 6 to 8 for example show three alternative configurations that each include alternative valve/pump housings 120, 220 and 320, respectively. Each of the housings 120, 220 and 320 define an aperture 80 through which piston 34 moves back and forth to pump fluid to and from a disposable cassette 90. Disposable cassette 90 is illustrated schematically in its operating position with respect to the housings 120, 220 and 320. Disposable cassette 90 can have various forms and in an embodiment includes a rigid portion (term includes rigid and semi-rigid) 92 that defines a plurality of fluid pathways bounded also by upper and lower flexible membranes 94 and 96, respectively (which are sealed to rigid portion 92). One preferred material for the flexible membranes 94 and 96 is discussed below in connection with Section IV.

Housings 120, 220 and 320 each define a vacuum chamber 82 within which a vacuum is applied to pull the lower flexible membrane or front sheet 96 away from rigid portion 92 of cassette 90 when piston 34 and piston head 36 are retracted inward towards the inside of the dialysis machine. FIGS. 6 to 8 each illustrate two pumps, however, the system of the present invention can have any number of pumps including one pump and more than two pumps. FIGS. 6 to 8 show the left pump in a retracted position, wherein dialysis fluid is pulled either from a supply (not illustrated) in a batch system, or from the patient (not illustrated), in a regeneration or CFPD type of dialysis system. With CFPD, the pump pulls dialysis fluid from the patient through one or more regeneration device, which contains materials that clean or regenerate the dialysate.

Various regeneration devices and materials are described in documents Ser. Nos. 10/623,317 and 10/624,150. Generally, any type of device that utilizes any suitable amount and type of material to clean effectively the dialysate prior to reuse can be used. In an embodiment, the cleaning device includes a material that is capable of non-selective removal of solutes from the dialysate that have been removed from the patient during therapy. The material can include any suitable sorbent material, such as carbon, activated carbon or other like material that is contained within a suitable housing, such as a cartridge, in any acceptable manner.

Other materials in addition to those which can non-selectively remove solutes from the dialysate can be used. The additional other materials include, for example, materials that can selectively remove certain solutes or the like from solution. In an embodiment, the additional materials can include a binder or reactive sorbent material capable of selectively removing urea, a binder or reactive sorbent material capable of selectively removing phosphate and/or the like. The use of materials capable of selective removal of solutes, particularly urea, can enhance the cleaning efficiency of the system so that the amount of dialysate necessary for effective treatment is minimized.

The materials that can selectively remove solutes from solution, such as binder materials, can include a variety of suitable and different materials including, for example, polymeric materials that are capable of removing nitrogen-containing compounds, such as urea, creatinine, other like metabolic waste and/or the like in solution. In general, these types of materials contain a functional group(s) that chemically binds with urea or other like solutes. One type of material includes alkenylaromatic polymers containing phenylglyoxal that function to chemically bind urea. In general, the phenylglyoxal polymeric material is made via acetylation performed in, for example, nitrobenzene followed by halogenation of the acetyl group and treatment with dimethylsulfoxide. Another example of a polymeric material that is capable of selectively removing solutes, such as urea, from solution includes polymeric materials that contain a tricarbonyl functionality commonly known as ninhydrin. The present invention can include any suitable type of material or combinations thereof to selectively remove solutes, such as urea, from solution as previously discussed.

One type of regeneration device is a cleaning cartridge. The cleaning cartridge can include a number of components in addition to the sorbent materials capable of removing solutes from the dialysate. For example, the cleaning cartridge may have the capability to remove all or a portion of electrolytes, such as sodium, potassium, or the like, from the dialysate solution. Here, an additional source of electrolytes in solution may be needed to replenish the dialysate after it has been cleaned. The cartridge may also be configured to release bicarbonate or the like into the system depending on the type of sorbent material used. This can facilitate pH regulation of the dialysate. As necessary, the cartridge may be filtered to prevent proteins, particulate matter or like constituents from leaching or exiting from the cartridge into the dialysate.

The cleaning cartridge is coupled to a dialysate loop via a cleaning fluid loop in an embodiment. The cartridge can include three separate layers, such as a layer of carbon, a layer of a phosphate binder and a layer of a urea binder. The cleaning fluid path includes suitable components to control the flow through the loop. In an embodiment, the rate of flow of the dialysate through the cleaning fluid loop, e.g., the cleaning flow rate, is less than the flow through the main dialysis fluid loop.

In the illustrated embodiments, the vacuum communicates with membrane 96 through chamber 82 of housings 120, 220 and 320. As discussed above in connection with reference numeral 38 of FIG. 2, the vacuum is introduced in an embodiment into chamber 82 through a channel in piston 34 and piston head 36. Piston head 36 in an embodiment defines grooves, such as grooves forming a star shape extending from the vacuum channel 38 orifice outwardly along the upper surface of piston head 36 to enable the vacuum to spread more evenly between piston head 36 and lower flexible membrane 96. The vacuum is alternatively introduced into chamber 82 via a separate fluid pathway (not illustrated) in housings 120, 220 and 320 extending to a negative pressure source.

FIG. 6 illustrates one embodiment for actuating pump piston 34 and piston head 36. Housing 120 defines a lower vacuum chamber 84 for each of the pump assemblies in addition to upper vacuum chambers 82 described above. A spring 86 is placed inside vacuum chamber 84. The spring 86 is coupled to a member 88, which is in turn coupled to piston 34. In an alternative embodiment, member 88 and piston 34 are formed integrally. Member 88, piston 34 and piston head 36 can be of any suitable material, such as hard plastic or metal, for instance, aluminum, stainless steel or other non-corrosive material. Spring 86 pushes against a bottom of housing 120 and member 88 to force the piston 34 and piston head 36 to contact lower flexible membrane 96 and push membrane 96 upward into rigid portion 92 of cassette 90. Spring 86 acts therefore to push or dispel fluid from disposable cassette 90.

To pump fluid into cassette 90, a deep vacuum is applied to chamber 84, which compresses spring 86. The spring in turn pulls member 88 and retracts piston 34 and piston head 36. The deep vacuum applied to chamber 34 is strong enough to overcome the spring constant and compression force of spring 86. In an embodiment, the deep vacuum applied to chamber 84 is from about −5 to about −30 psig.

When the deep vacuum is applied to chamber 84, a shallow vacuum is applied to chamber 82 simultaneously to pull lower flexible membrane 96 against the retracting piston head 36. The shallow vacuum is between 0 and −10 psig. In one embodiment a rolling diaphragm 98 is provided between member 88 and an inner wall of vacuum chamber 84. The diaphragm 98 seals to member 88 and the inner wall and separates the vacuums applied to chamber 82 and chamber 84. The back and forth movement of member 88, piston 34 and piston head 36 due to the expansion and retraction of spring 86 and the alternating application of a deep vacuum and a shallow vacuum to chamber 84 guides the rolling diaphragm 98 so that a nearly frictionless linear movement is generated.

When the deep vacuum 84 is removed so that spring 86 begins to expand, it is possible that due to the movement of the piston assembly or to a continuing shallow vacuum in chamber 82, rolling diaphragm 98 will invert from the generally downwardly extending orientation shown in FIG. 6. To prevent this from happening, a shallow vacuum is applied in chamber 84 during the push fluid stroke. The shallow vacuum in chamber 84 is also between 0 and −10 psig. in one embodiment. The shallow vacuum in an embodiment is the same shallow vacuum applied to chamber 82 so that the forces on either side of the diaphragm 98 via the shallow vacuums cancel one another. The shallow vacuum in chamber 84 is not large enough to overcome the spring constant of spring 86. Spring 86 is sized to apply the appropriate amount of force via piston head 36 to the lower flexible membrane 96, which can be as high as 35 lbs., taking into account that a negative force via the shallow vacuum in chamber 84 is acting against spring 86 during the pump out or dispel stroke.

FIGS. 6 to 8 illustrate one preferred sequence for operating multiple pumps. Pump pistons 34 move in and out alternatively, filling and emptying associated pump fluid chambers defined between rigid portion 92 and lower flexible membrane 96. The alternating pumps create a virtually constant flow of fluid to the patient. Dialysate intake and exhaust valves defined in part by disposable cassette 90 are opened and closed in conjunction with the movement of the pump pistons 34. In an embodiment, an intake valve (not illustrated) is open as an associated pump piston 34 retracts. The intake valve closes when the pump piston 34 extends towards cassette 90. The dialysis cassette also defines an exhaust valve that is closed as the associated pump piston retracts. The exhaust valve opens as the pump piston extends into cassette 90.

FIG. 7 illustrates an alternative pump actuator housed inside housing 220. The shallow vacuum is again applied to chamber 82, for example, via an orifice in pump piston 34 and piston head 36. The shallow vacuum draws the lower flexible membrane 96 up against pump piston heads 36. As in any of the embodiments described herein, the shallow vacuum within chamber 82 can be maintained or not maintained when pump piston 34 extends toward cassette 90 to dispel fluid from cassette 90. In FIG. 7, the member 88 and rolling diaphragm 98 of FIG. 6 are replaced by a cylinder 102 defining a deep vacuum chamber 104. A piston rod 106 attaches to piston 34 and seals against an inner surface of cylinder 102 via seals 108. A shaft seal, which can be of any known type, hereafter referred to as o-ring 112 is also placed within housing 220 between shaft opening 80 and the piston 34 to maintain the vacuum within chamber 82.

The operation of the cylinder 102 and cylinder rod 106 in conjunction with piston 34 is substantially the same as described above with diaphragm 98 and spring 86 of FIG. 6. In FIG. 7, a spring 114 is provided within each cylinder 102. The spring 114 pushes against cylinder rod 106, which in turn pushes piston 34 and piston head 36 towards rigid cassette 90. In an alternative embodiment, piston rod 106 can be eliminated, wherein piston 34 seals directly to the inner surface of cylinder 102, and wherein spring 114 is sized to push directly against piston 34. To withdraw the piston 34, a deep vacuum is applied to chamber 104 within cylinder 102, which overcomes the spring constant and compression resistance of spring 114.

Because the rolling diaphragm is not used, a shallow vacuum need not be maintained within chamber 104 in connection with the pump-out or fluid dispelling stroke. A shallow vacuum may be maintained within chamber 82 as described above, however, upon the pump-out or fluid dispelling stroke. Spring 114 does not need to overcome a residual negative pressure as in the case with embodiment of FIG. 6. Spring 114 may therefore be of a slightly decreased strength with respect to spring 86 and the deep vacuum may accordingly be slightly less than the deep vacuum employed with FIG. 6.

In an alternative embodiment, a positive pressure is applied outside of cylinder 102 to push rod 106 and compress spring 114 as opposed to drawing a vacuum within chamber 104 of cylinder 102. The o-ring seal 112 is still required to separate the positive pressure outside of cylinder 102 from the vacuum introduced into chamber 82. When the positive pressure is relieved, spring 114 pushes rod 106 and piston 34 as described above.

Referring now to FIG. 8, a further alternative embodiment eliminates the deep vacuum altogether and instead uses an electrically operated linear or rotary/linear actuator 32. Actuator 32 is also illustrated above in connection with FIG. 1. Linear actuator 32 in an embodiment is a linear stepper motor, a rotary stepper motor coupled to a lead or ball screw, a rotary servo motor coupled to a lead or ball screw or other type of electrically, pneumatically or hydraulically operated linear actuator. Pump actuator 32 couples in an embodiment directly to piston 34 via a coupler 116, which in an embodiment allows for slight misalignment between piston 34 and an output shaft of pump actuator 32. Pump actuator 32 eliminates altogether the need for the vacuum chamber 84, the deep vacuum and the residual shallow vacuum. A shallow vacuum is still required in chamber 82 to pull lower flexible membrane 96 away from rigid portion 92 when piston head 36 retracts away from cassette 90. O-ring 112 is provided between opening 80 in housing 320 and shaft 34 to form in part the enclosed vacuum chamber 82.

Figure 9:
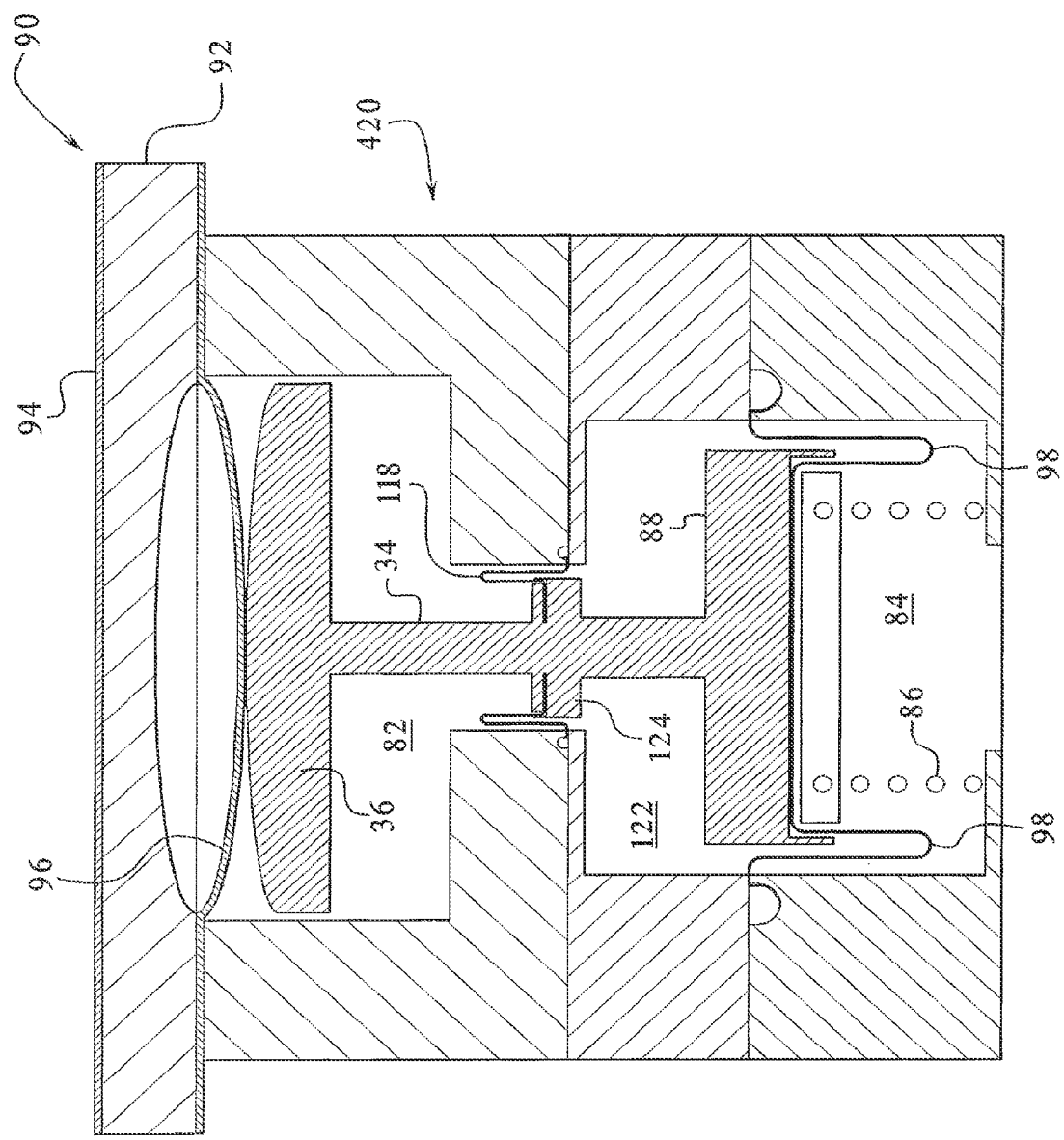
FIG. 9 is a sectioned elevation view of a further alternative embodiment of a pneumatically and mechanically operated pump of the present invention.

Referring now to FIG. 9, a further alternative embodiment for a pump actuator is illustrated. A portion of a housing 420 is illustrated. Housing 420 includes many of the same components as housing 120, such as the a shallow vacuum chamber 82, the deep vacuum chamber 84, the spring 86 and the rolling diaphragm 98 that couples sealingly to member 88 (connected to piston 34) and an inner surface of housing 420 (defining deep chamber 84). These components operate as described above, wherein a shallow vacuum is applied to chamber 82 to pull lower flexible membrane 96 away from rigid portion 92 of cassette 90. A deep vacuum is applied to chamber 84 to compress spring 86, which is coupled to member 88 and piston 34. Compression of spring 86 pulls piston 34 away from cassette 90. When the deep vacuum is removed from chamber 84, spring 86 decompresses and pushes piston 34 and piston head 36 towards cassette 90 to dispel fluid that exists between flexible member 96 and rigid portion 92.

The embodiment of FIG. 9 includes an additional rolling diaphragm 118. Each of the rolling diaphragms 98 and 118 is made of a strong, air impermeable and flexible material, such as silicone rubber sheeting or fabric reinforced silicone rubber. The additional rolling diaphragm 118 connects sealingly to an additional member 124 coupled to piston 34 and also sealingly to an inner surface of housing 420.

The combination of rolling diaphragms 98 and 118 creates a third sealed chamber 122 between chambers 82 and 84. The shallow vacuum in chamber 82 does not have the ability to corrupt the operation of diaphragm 98 as with the embodiment in FIG. 6. A separate shallow vacuum does not therefore need to be maintained in chamber 84 upon the fluid push or dispelling stroke. The spring constant 86 does not need to be chosen to overcome additionally the shallow vacuum in chamber 84. Because the spring 86 can be smaller, the level of deep vacuum in chamber 84 can likewise be decreased.

A number of options exists for controlling the pressure within third chamber 122. The pressure within third chamber 122 can be either be atmospheric or positive. If atmospheric, the negative pressure maintained within chambers 82 and 84 maintains the rolling diaphragms 118 and 98, respectively, in the proper illustrated orientations. A positive pressure applied to chamber 122 acts additionally to compress spring 86, push diaphragms 98 and 118 into their proper orientation, and may be used to withdraw piston 34 from cassette 90 during the fill stroke in place of or in addition to the deep vacuum maintained in chamber 84 to overcome the force of spring 86.

Referring now to FIGS. 10 and 11, an embodiment for actuating the valve plungers 42 illustrated above in FIG. 2 is illustrated. As also seen in FIG. 5, a plunger spring 70 operates to push plunger 42 towards one of the flexible membranes 94 or 96 of an alternative disposable cassette 190. Flexible membranes 94 and 96 seal to a semi-rigid or rigid, i.e., plastic, portion 192. In the embodiments described in connection with FIGS. 1 to 5, plunger spring 70 is housed within valve/pump housing 20, intermediate sheets 24 and 26 and front plate 30. In the alternative embodiment illustrated in FIG. 10, plunger spring 70 and plunger 42 are housed within a valve housing 130.

Valve housing 130 as with any of the pump housings 120, 220, 320 and 420, can be of a suitable hard plastic or be metal, such as a light metal, for example, aluminum. Valve housing 130 includes an outer section 132 and an inner section 134. A diaphragm 136 is sealed between outer section 132 and inner section 134. Diaphragm 136 in an embodiment is of the same material described above for rolling diaphragms 98 and 118 and is strong, flexible and air impermeable in one preferred embodiment. The plungers 42 connect to their respective diaphragms 136 via members 138. In the illustrated embodiment, diaphragms 136 are secured to members 138 via attachment mechanisms, such as bolts. Plunger spring 70 pushes against member 138, moving member 138 and plunger 42.

In an embodiment a compliant material 142 is placed at the end of the valve plunger 42 facing the respective flexible membrane 94 and 96. The compliant material can be rubber, for example, silicone rubber, neoprene rubber, Viton or ethylene propylene dienemethylene ("EPDM"). The compliant material aids in creating an airtight seal between valve plunger 42 and flexible sheet 94 or 96, compensating for minor surface imperfections in membranes 94 and 96 and/or in the rigid portion of 192 of cassette 190. The surface of rigid portion 192 that contacts and seals to the flexible membranes 94 and 96 is smooth in an embodiment or alternatively contains one or more concentric sealing rings which: (i) prevents the sheeting from adhering to rigid portion 192 when the valve is commanded to open; and (ii) provides multiple seals, dividing effectively the fluid pressure within cassette 190 that must be overcome by a factor of two or three, etc.

Similar to the operation of the pump in connection with FIG. 6, a deep vacuum is applied to chamber 144 defined by section 132 of housing 130, diaphragm 136 and member 138. A shallow vacuum is applied to chamber 146, which is defined by section 134 of housing 130, diaphragm 136 and member 138. The shallow vacuum applied within chamber 146 acts to pull the sheet 94, 96 against plunger 142 to open a fluid passageway 148 as illustrated by FIG. 11. Fluid passage 148 allows dialysis fluid to flow from passageway 152 defined by rigid portion 192 to passageway 154 defined by rigid portion 192 as illustrated by the arrow in FIG. 11.

To open fluid passageway 148, a deep vacuum is applied within chamber 144. Simultaneously, a shallow vacuum is applied within chamber 146. The deep vacuum is strong enough to overcome the force provided by plunger spring 70, e.g., two to ten lbs., as well as a counteracting force applied to diaphragm 136 via the shallow vacuum within chamber 146. In an embodiment, plunger spring 70 and plunger 42 apply a force of between zero and about 35 psig. to seal the membrane against pumping pressures, which can range from one to over 10 psig., providing a safety factor of three to one. FIG. 10 also illustrates that it is possible to have valves operate on multiple sides of cassette 190. Although not illustrated, it should be appreciated that multiple pumps can operate with multiple sides of the cassette 190 as well.

To close fluid passageway 148, the deep vacuum is removed within chamber 144. The shallow vacuum applied within chamber 146 may or may not be maintained. Spring 70 pushes plunger 42 against membrane 94, 96, which in turn seals against rigid portion 192. Spring 70 is between 0.5 and 1.25 inches when compressed and 0.75 to 1.5 inches in free length. The spring rates can range from about 5 to about 10.

III. Cassette Auto Alignment Feature

Referring now to FIGS. 12 to 14, an apparatus and method for automatically aligning the disposable cassette within a dialysis machine is illustrated. The apparatus and method also detect whether a cassette misalignment problem or a cassette integrity problem exists. FIG. 12 illustrates a dialysis machine 100 and a disposable cassette 150, wherein the cassette 150 is about to be loaded into machine 100. Cassette 150, like the cassettes described above, includes a rigid, e.g., plastic portion 162, an upper flexible membrane 94 and a lower flexible membrane 96. Rigid portion 162 and lower flexible membrane 96 define three pump chambers 168, 172 and 174. As discussed above, each of the embodiments of the present invention can have one or more pump chambers.

The dialysis machine 100 includes a housing having a base 170 and lid 180, which in the illustrated embodiment, is hinged to base 170 so as to form a clamshell-like structure. In the illustrated embodiment, assembly 10 of FIGS. 1 to 5 is housed inside of base 170. Front plate 30 of assembly 10 faces outward and is positioned to abut against and operate with cassette 150. As described above, pump piston heads 36 extend through front plate 30. For reference, valve plungers 42 and sensors 74 are also illustrated. For further reference, machine 100 is shown having a screen 176 with various indicia 178 shown thereon.

To control the dialysis therapy, a number of input devices 184 are provided, such as buttons, knobs and other types of switches. Alternatively, screen 176 is operable with a touch screen and a touch screen controller that allows an operator or patient to control the dialysis therapy through input devices displayed on screen 176. A controller (not illustrated), which can include multiple processors, such as a supervisory processor and a plurality of delegate processors: (i) controls screen 176; (ii) accepts inputs from devices 184; (iii) accepts inputs from sensors 74; and (iv) controls the actuation of the pistons 34, piston heads 36 and valve plungers 42, as well as other functions.

An inflatable bladder 182 is provided to inflate and lock cassette 150 against front plate 30 when the cassette 150 is in position. In the illustrated embodiment, inflatable bladder 182 is located on an inner surface 186 of lid 180. After cassette 150 is placed against front plate 30, lid 180 is closed. The controller then commands a pressure source to inflate inflatable bladder 182 to lock cassette 150 in place. Prior to the inflation of bladder 182, it is possible for cassette 150 to move slightly between front plate 30 and inner surface 186 of lid 180. It is also possible that either: (i) cassette 150 is misaligned with respect to front plate 30 when placed inside machine 100; and/or (ii) an integrity problem, e.g., a leak, exists between one of the flexible membranes 94, 96 and rigid portion 162.

FIGS. 13 and 14 illustrate a cross section taken through lines XIII-XIII and XIV-XIV respectively, of FIG. 12 after cassette 150 has been loaded into machine 100 and before inflatable bladder 182 has been inflated. A section of lid 180, which is hollow in an embodiment, is illustrated in the closed position residing directly above cassette 150. The lid is locked mechanically in an embodiment before the bladder 182 inflates, the pumps activate, etc. Inflatable bladder 182 loosely contacts upper flexible membrane 94. It should be appreciated that the cassette 150 can be loaded vertically in an alternative embodiment. Front plate 30 would then be disposed vertically inside base 170.

FIG. 13 illustrates that a slight misalignment exists between the pump chambers and piston heads. Pump chambers 168, 172 and 174 of cassette 150 are slightly to the right of the proper position above piston heads 36. Cassette 150 is slightly misaligned therefore to the right. In the dialysis therapy startup sequence of the present invention, the controller (not illustrated) commands at least one and in one preferred embodiment all of the pump pistons 34 and associated piston heads 36 to move upwards (or laterally for side load) to the fluid discharge position. FIG. 13 includes arrows illustrating this upward movement.

FIG. 14 shows an arrow pointing to the left indicating that as the piston heads 36 move upward, the heads contact lower flexible membrane 96 and abut rigid portion 162, causing the cassette 150 to slide to the left and move into the proper operating position. As illustrated, piston heads 36 and fluid pump chambers 168, 172 and 174 are tapered at their respective ends, which aids in aligning cassette 150 with respect front plate 30. The provision of at least two pump pistons ensures alignment in two dimensions. In an alternative embodiment pump pistons 34 can be slightly misaligned with respect to one another so as to provide an offset in both horizontal dimensions. If cassette 150 and front plate 30 are disposed vertically, multiple pump pistons 34 provide alignment in multiple vertical dimensions.

The cassette 150 may be misaligned to the point that piston heads 36 are too far out of alignment with respect to fluid pumping chambers 168, 172 and 174 for the misalignment to be corrected automatically. One or more sensors 188, such as strain gauge sensors, are provided to sense a resistance to the movement of the pump piston 34 and piston head 36. If the cassette 150 does not move into alignment, the force applied by pistons 134 to the rigid portion 162 of the cassette 150 is transferred across rigid portion 162 and is sensed by strain gauge 188. Strain gauge 188 sends an input to the controller. The controller is programmed to withdraw the pump pistons 34 and send an error message to screen 176 if the strain gauge input increases to an alarm set-point level.

It is also possible that due to improper formation of the rigid portion 162, or improper placement of flexible membrane 96 onto rigid portion 162, that the movement of one or more of the pistons 34 may be impeded. In such a case, as before, a force is transferred by the impeded piston, through the rigid portion 162, to the force sensor 188. Once again, sensor 188 sends a signal to the controller, which sends an alarm message to screen 176. In an embodiment, the alarm message alerts the user to the fact that the cassette could be misaligned or have an integrity problem. In an alternative environment, such as when multiple sensors 188 are provided, it may be possible for the controller to determine whether the problem is misalignment or integrity and send the proper corresponding message to screen 176. In either case, the controller halts the upward movement of the pump piston(s) and can retract same to alleviate the associated stress.

Once cassette 150 is determined to be in the proper position, as illustrated in connection with FIG. 14, the controller commands a pressure source to inflate inflatable bladder 182, locking cassette 150 between lid 180 and front plate 30. Either at this time, prior to this time or after this time, one or more of the pump pistons 34 can retract if needed.

IV. Flexible Membrane Material

Figure 15:
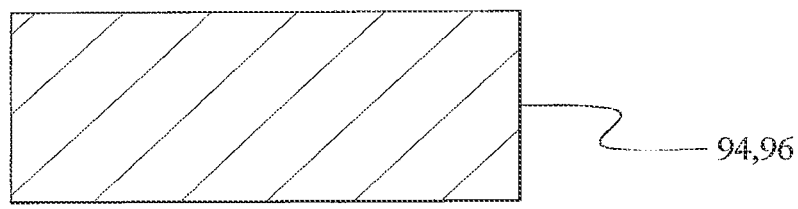
FIGS. 15 and 16 illustrate various embodiments of an improved membrane pumping material of the present invention.
Figure 16:
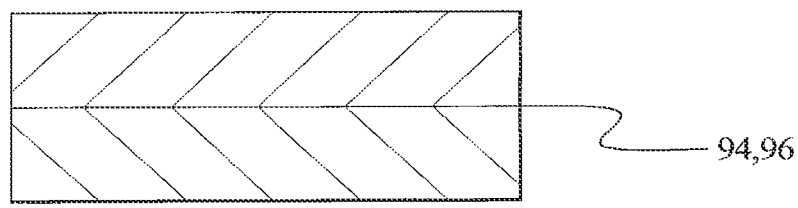
Figure 17:
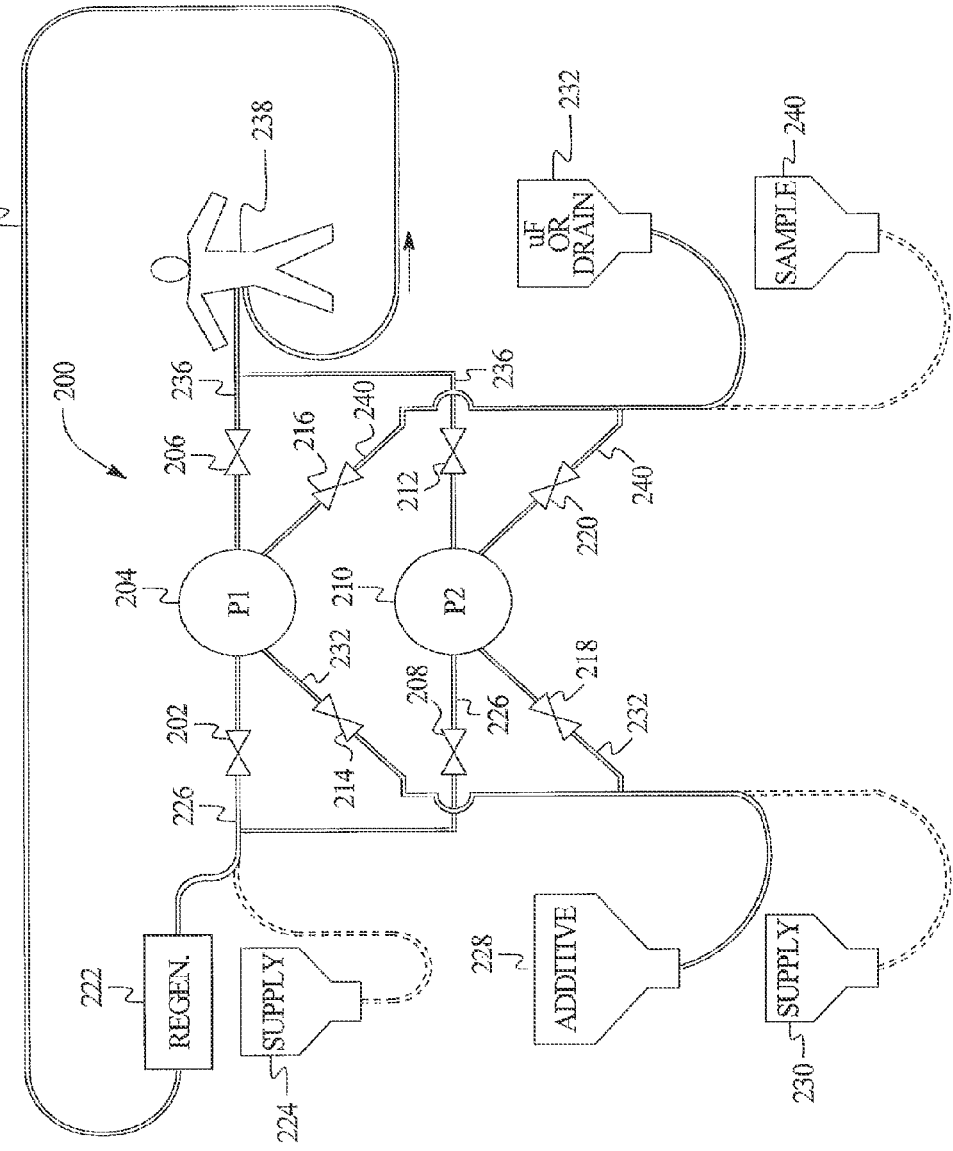

The pumping membrane film referred to herein with reference numerals 94 and 96 preferably is fabricated from a non-PVC containing, thermoplastic polymeric material and can be of a monolayer structure as shown in FIG. 15 or a multiple layer structure as shown in FIG. 16. The film can be fabricated using standard thermoplastic processing techniques such as extrusion, coextrusion, extrusion lamination, lamination, blown extrusion, tubular extrusion, cast extrusion or coextrusion, compression molding and thermoforming. Thermoforming is one preferred method for fabricating the film as it is well suited for fabricating the film having an elongation from about 5% to 40% and more preferably from 10% to 30%, and most preferably from 20 to 25%. In a preferred form of the invention, a portion of the film and more preferably a central portion will be domed. In a more preferred form of the invention the dome will have a diameter of 1.60 inches and a depth of 0.26 inches. The film will have a thickness of less than 15 mils and more preferably less than 12 mils and more preferably from about 11 mils to about 4 mils In a preferred form of the invention, the film should satisfy certain physical property requirements to function as a pumping membrane as described herein. The film should have a mechanical modulus to achieve precise fluid volume delivery rates. In a preferred form of the invention the modulus of elasticity will be less than 20,000 psi, more preferably less than 15,000 psi and even more preferably less than 10,000 psi when measured in accordance with ASTM D-882. The modulus of elasticity should remain essentially constant over a temperature range of from 5 to 40° C.

The pumping membrane film should also be sufficiently compatible with the material of the cassette 92, 150 and 192 so that the membrane film can be permanently adhered to the cassette using standard sealing techniques such as thermal welding, sonic welding or solvent bonding. Most preferably the film is attached to the cassette by heat sealing.

The pumping membrane film should be capable of being deformed by the piston head 36 or valve plungers 42 for ten thousand pumping strokes without a significant change in the volume of fluid being delivered. The volume will not vary by more than about 15 percent, more preferably about 10 percent and most preferably about 5 percent after 10,000 pumping strokes or after a therapy session or the like.

The film should also show minimal variation in mechanical properties over operating temperatures of from 5 to 40° C. In a preferred form of the invention the film can withstand contact with a 75° C. surface heater and withstand a spot temperature of 95° C. for 1 to 3 seconds. In yet another preferred form of the invention the film can have a heat transfer coefficient of greater than 0.20 Watts/Minute-Kelvin (K) for a film having a thickness of 5 mils.

In yet another preferred form of the invention a surface of the film facing the piston head 36 or valve plungers 42 will not stick to these devices to the extent it interrupts the pumping operation. In one preferred form of the invention, the film will have a textured surface to assist in preventing sticking of these devices to the film. The textured surface can include a matte or taffeta finish or other surface modification to reduce the surface area of the outer surface of the film the piston head 36 or valve plungers 42 contacts. The surface texture can be embossed or otherwise imparted to the film using techniques well known to the skilled artisan in the field of polymeric film processing.

The film, in a preferred form of the invention, will have a minimum or be free of gels. Gels are a heterogeneity in the film that appears as a local thickness increase. Gels are undesirable as they are more susceptible than other portions of the film to forming leaks.

It is also preferred the film not readily or permanently stick to itself so that the film can be fabricated, stored and assembled into the devices described herein with a minimum of challenges well known to those skilled in the art that result from a film sticking to itself.

It is also desirable the film present a barrier to water vapor transmission so that a minimum or insignificant amount of water is lost through the film during an eight hour therapy session. In a preferred form of the invention the water vapor transmission rate (WVTR) of the film when measured at 37.8° C. at 100% relative humidity is less than about 0.500 g/100 in$^2$/day and more preferably less than 0.300 g/100 in$^2$/day. Also, in a preferred form of the invention, the WVTR when measured at 25° C. at 100% relative humidity will be less than 0.200 g/100 in$^2$/day and more preferably less than 0.150 g/100 in$^2$/day.

The film should also be resistant to tearing and cutting. The film should resist tearing when an unsupported portion of the film is impinged upon by a plunger having a diameter of 1.6 inches with a 5-pound force applied thereto. In another preferred form of the invention, the film has an Elmendorf tear strength when measured in accordance with ASTM D 1922 of from 300 to 3,000 g, more preferably from 500-1,000 g. The film, in a preferred form of the invention, should have a durometer from about 45 to about 65 Shore A.

The film, in a preferred form of the invention, is capable of being sterilized by gamma or ethylene oxide sterilization techniques.

Again, in a preferred form of the invention, the film will have high transparency such as an optical haze of less than 30%, and more preferably less than 15% and even more preferably less than 10% and most preferably less than 5%, when measured for a film 9 mils thick and in accordance to ASTM D-1003.

Suitable non-PVC containing polymers include polyolefins, ethylene and lower alkyl acrylate copolymers, ethylene and lower alkyl substituted alkyl acrylate copolymers, ethylene vinyl acetate copolymers, polybutadienes, polyesters, polyamides, and styrene and hydrocarbon copolymers.

Suitable polyolefins include homopolymers and copolymers obtained by polymerizing alpha-olefins containing from 2 to 20 carbon atoms, and more preferably from 2 to 10 carbons. Therefore, suitable polyolefins include polymers and copolymers of propylene, ethylene, butene-1, pentene-1, 4-methyl-1-pentene, hexene-1, heptene-1, octene-1, nonene-1 and decene-1. Most preferably the polyolefin is a homopolymer or copolymer of propylene or a homopolymer or copolymer of polyethylene.

Suitable homopolymers of polypropylene can have a stereochemistry of amorphous, isotactic, syndiotactic, atactic, hemiisotactic or stereoblock. In one preferred form of the invention the homopolymer of polypropylene is obtained using a single site catalyst.

Suitable copolymers of propylene are obtained by polymerizing a propylene monomer with an α-olefin having from 2 to 20 carbons. In a more preferred form of the invention the propylene is copolymerized with ethylene in an amount by weight from about 1% to about 20%, more preferably from about 1% to about 10% and most preferably from 2% to about 5% by weight of the copolymer. The propylene and ethylene copolymers may be random or block copolymers. In a preferred form of the invention, the propylene copolymer is obtained using a single-site catalyst.

It is also possible to use a blend of polypropylene and a α-olefin copolymers wherein the propylene copolymers can vary by the number of carbons in the α-olefin. For example, the present invention contemplates blends of propylene and α-olefin copolymers wherein one copolymer has a 2 carbon α-olefin and another copolymer has a 4 carbon α-olefin. It is also possible to use any combination of α-olefins from 2 to 20 carbons and more preferably from 2 to 8 carbons. Accordingly, the present invention contemplates blends of propylene and α-olefin copolymers wherein a first and second α-olefins have the following combination of carbon numbers: 2 and 6, 2 and 8, 4 and 6, 4 and 8. It is also contemplated using more than 2 polypropylene and α-olefin copolymers in the blend. Suitable polymers can be obtained using a catalloy procedure.

It may also be desirable to use a high melt strength polypropylene. High melt strength polypropylenes can be a homopolymer or copolymer of polypropylene having a melt flow index within the range of 10 grams/10 min. to 800 grams/10 min., more preferably 30 grams/10 min. to 200 grams/10 min, or any range or combination of ranges therein. High melt strength polypropylenes are known to have free-end long chain branches of propylene units. Methods of preparing polypropylenes which exhibit a high melt strength characteristic have been described in U.S. Pat. Nos. 4,916,198; 5,047,485; and 5,605,936 which are incorporated herein by reference and made a part hereof. One such method includes irradiating a linear propylene polymer in an environment in which the active oxygen concentration is about 15% by volume with high energy ionization energy radiation at a dose of 1 to $10^4$ megarads per minute for a period of time sufficient for a substantial amount of chain scission of the linear propylene polymer to occur but insufficient to cause the material to become gelatinous. The irradiation results in chain scission. The subsequent recombination of chain fragments results in the formation of new chains, as well as joining chain fragments to chains to form branches. This results in the desired free-end long chain branched, high molecular weight, non-linear, propylene polymer material. Radiation is maintained until a significant amount of long chain branches form. The material is then treated to deactivate substantially all the free radicals present in the irradiated material.

High melt strength polypropylenes can also be obtained as described in U.S. Pat. No. 5,416,169, which is incorporated in its entirety herein by reference and made a part hereof, when a specified organic peroxide (di-2-ethylhexyl peroxydicarbonate) is reacted with a polypropylene under specified conditions, followed by melt-kneading. Such polypropylenes are linear, crystalline polypropylenes having a branching coefficient of substantially 1, and, therefore, have no free end long-chain branching and will have a intrinsic viscosity of from about 2.5 dl/g to 10 dl/g.

Suitable homopolymers of ethylene include those having a density of greater than 0.915 g/cc and includes low density polyethylene (LDPE), medium density polyethylene (MDPE) and high density polyethylene (HDPE).

Suitable copolymers of ethylene are obtained by polymerizing ethylene monomers with an α-olefin having from 3 to 20 carbons, more preferably 3-10 carbons and most preferably from 4 to 8 carbons. It is also desirable for the copolymers of ethylene to have a density as measured by ASTM D-792 of less than about 0.915 g/cc and more preferably less than about 0.910 g/cc and even more preferably less than about 0.905 g/cc. Such polymers are often times referred to as VLDPE (very low density polyethylene) or ULDPE (ultra low density polyethylene). Preferably the ethylene α-olefin copolymers are produced using a single site catalyst and even more preferably a metallocene catalyst systems. Single site catalysts are believed to have a single, sterically and electronically equivalent catalyst position as opposed to the Ziegler-Natta type catalysts which are known to have a mixture of catalysts sites. Such single-site catalyzed ethylene α-olefins are sold by Dow under the trade name AFFINITY, DuPont Dow under the trademark ENGAGE® and by Exxon under the trade name EXACT. These copolymers shall sometimes be referred to herein as m-ULDPE.

Suitable copolymers of ethylene also include ethylene and lower alkyl acrylate copolymers, ethylene and lower alkyl substituted alkyl acrylate copolymers and ethylene vinyl acetate copolymers having a vinyl acetate content of from about 8% to about 40% by weight of the copolymer. The term "lower alkyl acrylates" refers to comonomers having the formula set forth in Diagram 1:

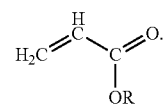

Diagram 1

The R group refers to alkyls having from 1 to 17 carbons. Thus, the term "lower alkyl acrylates" includes but is not limited to methyl acrylate, ethyl acrylate, butyl acrylate and the like.

The term "alkyl substituted alkyl acrylates" refers to comonomers having the formula set forth in Diagram 2:

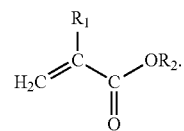

Diagram 2

$R_1$ and $R_2$ are alkyls having 1 to 17 carbons and can have the same number of carbons or have a different number of carbons. Thus, the term "alkyl substituted alkyl acrylates" includes but is not limited to methyl methacrylate, ethyl methacrylate, methyl ethacrylate, ethyl ethacrylate, butyl methacrylate, butyl ethacrylate and the like.

Suitable polybutadienes include the 1,2- and 1,4-addition products of 1,3-butadiene (these shall collectively be referred to as polybutadienes). In a more preferred form of the invention the polymer is a 1,2-addition product of 1,3 butadiene (these shall be referred to as 1,2 polybutadienes). In an even more preferred form of the invention the polymer of interest is a syndiotactic 1,2-polybutadiene and even more preferably a low crystallinity, syndiotactic 1,2 polybutadiene. In a preferred form of the invention the low crystallinity, syndiotactic 1,2 polybutadiene will have a crystallinity less than 50%, more preferably less than about 45%, even more preferably less than about 40%, even more preferably the crystallinity will be from about 13% to about 40%, and most preferably from about 15% to about 30%. In a preferred form of the invention the low crystallinity, syndiotactic 1,2 polybutadiene will have a melting point temperature measured in accordance with ASTM D 3418 from about 70° C. to about 120° C. Suitable resins include those sold by JSR (Japan Synthetic Rubber) under the grade designations: JSR RB 810, JSR RB 820, and JSR RB 830.

Suitable polyesters include polycondensation products of di-or polycarboxylic acids and di or poly hydroxy alcohols or alkylene oxides. In a preferred form of the invention the polyester is a polyester ether. Suitable polyester ethers are obtained from reacting 1,4 cyclohexane dimethanol, 1,4 cyclohexane dicarboxylic acid and polytetramethylene glycol ether and shall be referred to generally as PCCE. Suitable PCCE's are sold by Eastman under the trade name ECDEL.

Suitable polyesters further include polyester elastomers which are block copolymers of a hard crystalline segment of polybutylene terephthalate and a second segment of a soft (amorphous) polyether glycols. Such polyester elastomers are sold by Du Pont Chemical Company under the trade name HYTREL®.

Suitable polyamides include those that result from a ring-opening reaction of lactams having from 4 to 12 carbons. This group of polyamides therefore includes nylon 6, nylon 10 and nylon 12. Acceptable polyamides also include aliphatic polyamides resulting from the condensation reaction of di-amines having a carbon number within a range of 2 to 13, aliphatic polyamides resulting from a condensation reaction of di-acids having a carbon number within a range of 2 to 13, polyamides resulting from the condensation reaction of dimer fatty acids, and amide containing copolymers. Thus, suitable aliphatic polyamides include, for example, nylon 66, nylon 6,10 and dimer fatty acid polyamides.

The styrene of the styrene and hydrocarbon copolymer includes styrene and the various substituted styrenes including alkyl substituted styrene and halogen substituted styrene. The alkyl group can contain from 1 to about 6 carbon atoms. Specific examples of substituted styrenes include alpha-methylstyrene, beta-methylstyrene, vinyltoluene, 3-methylstyrene, 4-methylstyrene, 4-isopropylstyrene, 2,4-dimethylstyrene, o-chlorostyrene, p-chlorostyrene, o-bromostyrene, 2-chloro-4-methylstyrene, etc. Styrene is the most preferred.

The hydrocarbon portion of the styrene and hydrocarbon copolymer includes conjugated dienes. Conjugated dienes which may be utilized are those containing from 4 to about 10 carbon atoms and more generally, from 4 to 6 carbon atoms. Examples include 1,3-butadiene, 2-methyl-1,3-butadiene (isoprene), 2,3-dimethyl-1,3-butadiene, chloroprene, 1,3-pentadiene, 1,3-hexadiene, etc. Mixtures of these conjugated dienes also may be used such as mixtures of butadiene and isoprene. The preferred conjugated dienes are isoprene and 1,3-butadiene.

The styrene and hydrocarbon copolymers can be block copolymers including di-block, tri-block, multi-block, and star block. Specific examples of diblock copolymers include styrene-butadiene, styrene-isoprene, and the hydrogenated derivatives thereof. Examples of triblock polymers include styrene-butadiene-styrene, styrene-isoprene-styrene, alpha-methylstyrene-butadiene-alpha-methylstyrene, and alpha-methylstyrene-isoprene-alpha-methylstyrene and hydrogenated derivatives thereof.

The selective hydrogenation of the above block copolymers may be carried out by a variety of well known processes including hydrogenation in the presence of such catalysts as Raney nickel, noble metals such as platinum, palladium, etc., and soluble transition metal catalysts. Suitable hydrogenation processes which can be used are those wherein the diene-containing polymer or copolymer is dissolved in an inert hydrocarbon diluent such as cyclohexane and hydrogenated by reaction with hydrogen in the presence of a soluble hydrogenation catalyst. Such procedures are described in U.S. Pat. Nos. 3,113,986 and 4,226,952, the disclosures of which are incorporated herein by reference and made a part hereof.

Particularly useful hydrogenated block copolymers are the hydrogenated block copolymers of styrene-isoprene-styrene, such as a styrene-(ethylene/propylene)-styrene block polymer. When a polystyrene-polybutadiene-polystyrene block copolymer is hydrogenated, the resulting product resembles a regular copolymer block of ethylene and 1-butene (EB). As noted above, when the conjugated diene employed is isoprene, the resulting hydrogenated product resembles a regular copolymer block of ethylene and propylene (EP). One example of a commercially available selectively hydrogenated block copolymer is KRATON G-1652 which is a hydrogenated SBS triblock comprising 30% styrene end blocks and a midblock equivalent is a copolymer of ethylene and 1-butene (EB). This hydrogenated block copolymer is often referred to as SEBS. Other suitable SEBS or SIS copolymers are sold by Kurrarry under the tradename SEPTON® and HYBRAR®.

It may also be desirable to use graft modified styrene and hydrocarbon block copolymers by grafting an alpha,beta-unsaturated monocarboxylic or dicarboxylic acid reagent onto the selectively hydrogenated block copolymers described above.

The block copolymers of the conjugated diene and the vinyl aromatic compound are grafted with an alpha,beta-unsaturated monocarboxylic or dicarboxylic acid reagent. The carboxylic acid reagents include carboxylic acids per se and their functional derivatives such as anhydrides, imides, metal salts, esters, etc., which are capable of being grafted onto the selectively hydrogenated block copolymer. The grafted polymer will usually contain from about 0.1 to about 20%, and preferably from about 0.1 to about 10% by weight based on the total weight of the block copolymer and the carboxylic acid reagent of the grafted carboxylic acid. Specific examples of useful monobasic carboxylic acids include acrylic acid, methacrylic acid, cinnamic acid, crotonic acid, acrylic anhydride, sodium acrylate, calcium acrylate and magnesium acrylate, etc. Examples of dicarboxylic acids and useful derivatives thereof include maleic acid, maleic anhydride, fumaric acid, mesaconic acid, itaconic acid, citraconic acid, itaconic anhydride, citraconic anhydride, monomethyl maleate, monosodium maleate, etc.

The styrene and hydrocarbon block copolymer can be modified with an oil such as the oil modified SEBS sold by the Shell Chemical Company under the product designation KRATON G2705.

In a most preferred form of the invention the membrane film will be a monolayer structure as shown in FIG. 15 and be fabricated from a m-ULDPE resin. For multiple layer films having two layers as shown in FIG. 16 or more it is desirable for an inner, solution contacting layer to be a m-ULDPE and the layer or layers outward therefrom (outer layer) can be a polymeric material selected from a polymer set forth above, a metal foil or paper. The pumping film is attached to the cassette and has a portion attached to the cassette and another portion unsupported by the cassette and extends between supported portions of the cassette. The film is generally taught between the portions where the film attaches to the cassette. Thus, the film extends between a first support and a second support and satisfies one or more of the physical properties set forth above. The pumping film overlies a fluid reservoir and is moveable from a first position to a second position to move fluid through the reservoir. The film is moved between the first and second position in response to a single or a series of periodic impingements of the film by the piston head 36 or valve plungers 42 or the like on a portion of the film not supported. While the cassette shown herein is generally rectangular shaped, it could have numerous different shapes such as polygonal, round, elliptical and irregular shaped without departing from the scope of the invention.

The cassette is preferably fabricated from a thermoplastic polymer and more preferably from a rigid thermoplastic polymer. In a preferred form of the invention the cassette is fabricated from a polyolefin such as a homopolymer or copolymer of propylene as described above or a homopolymer or copolymer of a cyclic olefin or a homopolymer or copolymer of a bridged polycyclic hydrocarbon. Such polymers shall sometimes be collectively referred to as COCs.

Suitable homopolymer and copolymers of cyclic olefins and bridged polycyclic hydrocarbons and blends thereof can be found in U.S. Pat. Nos. 5,218,049; 5,854,349; 5,863,986; 5,795,945; 5,792,824; 4,993,164; 5,008,356; 5,003,019; and 5,288,560 all of which are incorporated in their entirety herein by reference and made a part hereof. In a preferred form of the invention these homopolymers, copolymers and polymer blends will have a glass transition temperature of greater than 50 degree C., more preferably from about 70 degree C. to about 180 degree C., a density greater than 0.910 g/cc and more preferably from 0.910 g/cc to about 1.3 g/cc and most preferably from 0.980 g/cc to about 1.3 g/cc and have from at least about 20 mole % of a cyclic aliphatic or a bridged polycyclic in the backbone of the polymer more preferably from about 30-65 mole % and most preferably from about 30-60 mole %.

In a preferred form of the invention, suitable cyclic olefin monomers are monocyclic compounds having from 5 to about 10 carbons in the ring. The cyclic olefins can selected from the group consisting of substituted and unsubstituted cyclopentene, cyclopentadiene, cyclohexene, cyclohexadiene, cycloheptene, cycloheptadiene, cyclooctene, cyclooctadiene. Suitable substituents include lower alkyl, acrylate derivatives and the like.

In a preferred form of the invention, suitable bridged polycyclic hydrocarbon monomers have two or more rings and more preferably contain at least 7 carbons. The rings can be substituted or unsubstituted. Suitable substitutes include lower alkyl, aryl, aralkyl, vinyl, allyloxy, (meth) acryloxy and the like. The bridged polycyclic hydrocarbons are selected from the group consisting of those disclosed in the above incorporated patents and patent applications. In a preferred form of the invention the polycyclic hydrocarbon is polymerized in an addition reaction in preference to a ring opening metathesis polymerization (ROMP). Suitable bridged polycyclic hydrocarbon containing polymers are sold by Ticona under the tradename TOPAS, by Nippon Zeon under the tradename ZEONEX and ZEONOR, by Daikyo Gomu Seiko under the tradename CZ resin, and by Mitsui Petrochemical Company under the tradename APEL.

Suitable comonomers include alpha-olefins having from 3 to 10 carbons, aromatic hydrocarbons, other cyclic olefins and bridged polycyclic hydrocarbons. It may also be desirable to have pendant groups associated with the above-mentioned homopolymers and copolymers. The pendant groups are for compatibilizing the cyclic olefin containing polymers and the bridged polycyclic hydrocarbon containing polymers with more polar polymers including amine, amide, imide, ester, carboxylic acid and other polar functional groups. Suitable pendant groups include aromatic hydrocarbons, carbon dioxide, monoethylenically unsaturated hydrocarbons, acrylonitriles, vinyl ethers, vinyl esters, vinylamides, vinyl ketones, vinyl halides, epoxides, cyclic esters and cyclic ethers. The monethylencially unsaturated hydrocarbons include alkyl acrylates, and aryl acrylates. The cyclic ester includes maleic anhydride.

It has been found that polymer blends may also be suitable to fabricate the cassette. Suitable two-component blends of the present invention include as a first component of a COC. The COCs can be present in an amount from about 1 to 99% by weight of the blend, more preferably from about 30 to 99%, and most preferably from about 35 to 99 weight percent or any combination or subcombination or ranges therein. In a preferred form of the invention the first components has a glass transition temperature of from about 70 degree C. to about 130 degree C. and more preferably from about 70 to 110 degree C.

The blends further include a second component in an amount by weight of the blend of from about 99-1%, more preferably from about 70-1% and most preferably from about 65-1%. The second component is selected from the group consisting of homopolymers and copolymers of ethylene, propylene, butene, hexene, octene, nonene, decene and styrene. The second component preferably has a density of from about 0.870 to 0.960 g/cc and more preferably from about 0.910 to 0.960 g/cc and more preferably from about 0.930 to 0.960 g/cc. In a preferred form of the invention the second component is and ethylene and alpha-olefin copolymer where the alpha-olefin has from 3 to 10 carbons, more preferably from 4 to 8 carbons and most preferably 6 carbons. Most preferably the ethylene and alpha-olefin copolymers are obtained using a metallocene catalyst.

Suitable three-component blends include as a third component a COC selected from those COCs described above and different from the first component. In a preferred form of the invention the second COC will have a glass transition temperature of higher than about 120 degree C. when the first COC has a glass transition temperature lower than about 120 degree C. In a preferred form of the invention, the third component is present in an amount by weight of from about 10 to 90% by weight of the blend and the first and second components should be present in a ratio of from about 2:1 to about 1:2 respectively of the first component to the second component.

In a preferred form of the invention, random and block copolymers of norbornene and ethylene are selected as the first component of the blend. These norbornene copolymers are described in detail in U.S. Pat. Nos. 5,783,273, 5,744,664, 5,854,349, and 5,863,986. The norbornene ethylene copolymer preferably has from at least about 20 mole percent norbornene monomer and more preferably from about 20 to 75 mole percent and most preferably from about 30 to 60 mole percent norbornene monomer or any combination or subcombination of ranges therein. The norbornene ethylene copolymer should have a glass transition temperature of from about 70 to 180 degree C., more preferably from 70 to 130 degree C. and even more preferably from about 70 to 100 degree C.

The second component is preferably an ethylene copolymerized with an alpha-olefin having from 4 to 8 carbons. Preferably, the ethylene and alpha-olefin copolymers are obtained using metallocene catalysts. Suitable catalyst systems, among others, are those disclosed in U.S. Pat. Nos. 5,783,638 and 5,272,236. Suitable ethylene and alpha-olefin copolymers include those sold by Dow Chemical Company under the AFFINITY and ENGAGE tradenames, those sold by Exxon under the EXACT tradename and those sold by Phillips Chemical Company under the tradename MARLEX.

As set forth above, the first component of the norbornene/ethylene copolymer can be present from about 1 to 99% by weight of the blend, more preferably from about 30 to 99% by weight, and most preferably 35 to 99% by weight. In a preferred three-component blend a second norbornene and ethylene copolymer is added to the two component norbornene-ethylene/ethylene alpha.-olefin blend. The second norbornene ethylene copolymer should have a norbornene monomer content of 30 mole percent or greater and more preferably from about 35 to 75 mole percent and a glass transition temperature of higher than 120 degree C. when the first component has a glass transition temperature of lower than 120 degree C.

The cassette may be fabricated from the COCs and blends set forth above. The cassette may be fabricated from the COCs by injection molding, blow molding, thermoforming processes or other plastic fabricating techniques. In a preferred form of the invention the cassette is formed by injection molding.

The tubing connected to the cassette is compatible with the cassette and is, in a preferred form of the invention, made from a polyolefin and more preferably from a m-ULDPE and even more preferably from a blend of m-ULDPE resins in accordance with commonly assigned U.S. Pat. No. 6,372,848 which is incorporated in its entirety herein by reference. The tubing is in fluid communication with the fluid reservoir and can convey fluid to and from the reservoir.

V. Multiplexing Dialysis Fluid Flow

Referring now to FIGS. 17 to 20, valve and pump arrangement 200 illustrates one possible arrangement for the pumps and valves of the present invention. FIGS. 18 to 20 set forth a set of values that illustrate one example of how the valves are sequenced in connection with the valve arrangement 200. Other sets of values are therefore possible.

The cassette-based improvements discussed herein are operable with various different types of dialysis therapies, such as hemodialysis and peritoneal dialysis. With peritoneal dialysis, for example, the system can be a batch system, a continuous flow system, a tidal flow system and any combination thereof. With batch type systems, dialysis fluid is pumped through the patient and then to drain. Tidal flow systems are modified batch type systems, wherein instead of pulling all the fluid out of the patient's peritoneal cavity, a portion of the fluid is pulled out more frequently and replaced. Tidal flow systems have properties similar to both batch and continuous therapies.

In continuous flow systems, dialysis fluid is pumped to a patient, through one or more filters and regeneration devices back to the patient. Continuous flow systems require typically one or more concentrates to be added to the fluid before the fluid reaches the patient. Also, a roughly equal amount of ultrafiltrate produced by the patient is removed from circulation, so that a total volume of fluid within the loop remains relatively constant. The components described herein can be used likewise in a variable volume CFPD system.

Pump and valve arrangement 200 is operable with each of these types of systems. Arrangement 200 is particularly suited for continuous flow therapies and is described in connection with CFPD accordingly, although it is not limited to CFPD. Pump/valve arrangement 200 includes a first intake valve 202 upstream of a first pump chamber 204 and a first exhaust valve 206 downstream of pump chamber 204. Pump/valve arrangement 200 includes a first intake valve 208 upstream of a second pump chamber 210 and a first exhaust valve 212 downstream of second pump chamber 210.

Operating in concert with the first inlet valve 202, a second intake valve 214 is located upstream of first pump chamber 204. Similarly, a second exhaust valve 216 is located downstream of first pump chamber 204. Operating in concert with first intake valve 208, a second intake valve 218 is placed upstream of second pump chamber 210. Operating in concert with first exhaust valve 212, a second exhaust valve 220 is located downstream of second pump chamber 210.

In a continuous flow system, regenerated dialysis fluid flows from one or more regeneration device 222, through a first inlet path 226, through first intake valves 202 and 208, to first and second pump chambers 204 and 210, respectively. In the continuous flow system, at the same time or at a slightly different time as discussed in more detail below, one or more additives or concentrates 228 flows through a second inlet path 232, through second intake valves 214 and/or 218, into first and second pump chambers 204 and/or 210, respectively. Pumps 204 and 210 in an embodiment alternate so that one pump draws in fluid as the second pump pushes fluid to the patient.

In arrangement 200, with respect to continuous flow dialysis, dialysis fluid flows from pumps 204 and 210, through first exhaust valves 206 and 212, respectively, through first outlet path 236 to patient 238. With continuous flow, fluid can be discharged alternatively from pumps 204 and 210, through second exhaust valves 216 and 220, respectively, through second outlet path 240, to an ultrafiltrate bag 232. In one embodiment, fluid flows from patient 238, through a regeneration path 234, to regeneration device 222.

In automated peritoneal dialysis ("APD") or in tidal flow, the regeneration device 222 and additives 228 are replaced by one or more supply bag 224 and 230. Here, pumps 204 and 210 pull fluid alternatively from supply bag 224, through first inlet line 226 and first intake valves 202 and 208 and/or from supply 230, through second inlet path 232 and second intake valves 214 and 218, respectively. In APD or tidal flow, pumps 204 and 210 pump to the patient 238 via first outlet path 236, through first exhaust valves 206 and 212. Alternatively, pumps 204 and/or 210 can pump via second outlet path 240 through second exhaust valves 216 and 220, to a sample bag 240 for example.

Thus, with APD or tidal flow, spent fluid is pumped from the patient to drain, so that first outlet path 236 operates as a from patient path and second outlet path 240 flows to drain 232. With CFPD, the flow can alternatively be reversed and flow instead from patient 238, through first outlet path 236, to one or both pumps 204 and 210, to ultrafiltrate collection 232. Here, first inlet path 226 and first outlet path 236 can have multiple lumens to allow flow in both directions simultaneously.

For the ease of illustration, the remainder of the present invention with respect to Section V is discussed in connection with CFPD. In CFPD, second inlet valves 214 and 218 enable intermittent injection of a second fluid, e.g., an additive, to the main dialysis fluid flowing continuously through first inlet path 226. Second exhaust valves 216 and 220 allow for intermittent withdrawal of fluid, e.g., ultrafiltrate, from the main dialysis fluid flowing continuously through first outlet path 236. The second inlet valves 214 and 218 and second outlet valves 216 and 220 enable the additional pumping functions to be accomplished without providing additional pumping chambers. Eliminating additional pumping chambers allows the disposable cassette, and consequently the overall dialysis machine, to be smaller, lighter and less costly. The operation of a machine having a smaller number of pump chambers is also less noisy than a machine with a greater number of pump fluid chambers.

FIGS. 18 to 20 illustrate one example of the sequencing of pump 204 and 210 and the various valves in connection with arrangement 200 for CFPD. FIG. 18 illustrates the cycling of pumps 204 and 210 with respect to the main flow of dialysis fluid from the regeneration devices 222, through first inlet path 226 and first outlet path 236, to patient 238. In the example the main dialysate flow through arrangement 200 is set at a rate of 100 ml/minute. In an embodiment, each pump chamber 204 and 210 has a total volume capability of 10 ml. The pump actuators and pistons 34 are operated so that one complete pump cycle (both valves performing a stroke) occurs every 12 seconds.

FIG. 18 illustrates the volume of fluid being delivered from the pumps 204 and 210 to patient 238. During the first six seconds, pump 204 (P1) pumps 10 ml of fluid through valve 206 and first exhaust path 236 to patient 238. First exhaust valve 212 operating with pump 210 is closed. During that same first six seconds, 10 ml of dialysis fluid is pumped from the one or more regeneration devices 222, through first inlet path 226, through first intake valve 208, into pump chamber 210. During this same time, first intake valve 202 is closed.

During the second six seconds or the second half of one complete pump cycle, pump 210 discharges fluid obtained during the first six seconds to patient 238. Pump 204 pulls fluid from regeneration device 222 in preparation for pumping to patient 238 in the second pump cycle. During the second six seconds of the first pump cycle, first exhaust valve 212 associated with pump 210 is open, while first exhaust valve 206 associated with pump 204 is closed. First intake valve 202 associated with pump chamber 204 is open, while first intake valve 208 associated with pump 210 is closed. Also during the second six seconds of the first complete cycle, pump 210 (P2) delivers 10 ml of fluid to patient 238. The complete cycle is then repeated four more times over a total of one minute, delivering a total of 100 ml of fluid.

FIGS. 19 and 20 illustrate various possibilities for sequencing the second inlet valves 214 and 218 to add one or more additives 228 and sequencing second exhaust valves 216 and 220 to remove ultrafiltrate 232, respectively. FIG. 19 illustrates the frequency with which pumps 204 and 210 need to pull alternatively from additive 228, through second inlet path 232, through valves 214 and 218 to achieve a particular flowrate of additive. For example, if it is desired to have an additive flowrate of one ml/minute, knowing the pump chamber volume to be a constant 10 ml, a total of one full chamber of dialysate must be pulled through pumps 204 and 210 collectively every ten minutes. This means that each pump will pump one full chamber of dialysis fluid once every twenty minutes.

Knowing that there is a total of ten output strokes (both pumps) per minute, each pump 204 and 210 must pump a chamber full of additive 228 every one hundred strokes to achieve individually one full chamber once every twenty minutes. For a flow of 1 ml of additive per minute when the total flow of dialysate to the patient is 100 ml/minute, for pump 204, first intake valve 202 opens ninety-nine consecutive times. Second intake valve 214 opens on the 100th intake stroke. Likewise, for pump 210, first intake valve 208 opens ninety-nine consecutive times. Valve 218 opens on the 100th intake stroke.

FIG. 19 illustrates the total chamber volume and stroke sequence for additive flowrates of 0.2, 0.5, 1.0, 1.5, 2.0 and 3.0 ml/min. It should be appreciated, however, that any desired percentage of additive versus dialysis flow can be achieved via the sequencing of second intake valves 214 and 218 with respect to the opening of main inlet valves 202 and 208, respectively.

Referring now to FIG. 20, an ultrafiltrate removal table is illustrated. The analysis described above for determining the values in the additive sequencing table FIG. 19 is the same used to determine the values in the ultrafiltrate table. Accordingly, to remove one ml per minute of fluid to ultrafiltrate container 232, each of the pumps 204 and 210 pumps one full chamber volume of 10 ml of fluid once every one hundred strokes to ultrafiltrate bag 232 (assuming overall flowrate of dialysis flow is 100 ml/minute as shown in FIG. 18). Pumps 204 and 210 pump collectively one chamber volume, e.g., 10 ml of fluid every 10 minutes to achieve an ultrafiltrate flowrate of one ml/minute Accordingly, first exhaust valves 206 and 212 are opened ninety-nine times consecutively. Thereafter, second exhaust valves 216 and 220 are opened upon the 100th stroke.

In both the control of the additive and ultrafiltrate, the opening of the second inlet valves 214 and 218 can be spaced apart as desired. For example, when the cycle is one every 100 strokes, opening valves 214 and 218 can be offset by fifty strokes. In a similar manner, the ultrafiltrate can be pulled through second outlet path 240 via valve 216 and fifty strokes later through valve 220. It should be appreciated from FIGS. 19 and 20 that the additive flowrate can be different than the ultrafiltrate flowrates. It may be necessary, however, to make up the total volume flowing through the loop if the removal rate is larger than the additive rate or vice versa. Ultrafiltrate produced by the patient must also be accounted for, for example, by removing ultrafiltrate at a faster rate than that at which concentrate is added.

In an embodiment, additive 228 and ultrafiltrate 232 are added and removed, respectively, virtually simultaneously by opening, for example, second inlet valve 214 operating in communication with pump 204 while simultaneously opening second exhaust valve 220 operating in communication with pump 210, when pump 204 is in a pull stroke and pump 210 is in a push stroke. This allows additive to be mixed into the system simultaneously with ultrafiltrate being pulled from the system in a way such that the additive is not being removed immediately from the patient loop. It should be appreciated that the pumping order can be reversed so that pump 210 pulls in additive 228, while pump 204 discharges ultrafiltrate to container 232.

Partial pump strokes can be used in an embodiment. With a positionable pump actuator, such as the linear or rotational stepper or servo motor in combination with a rotational to linear converter described above in connection with FIG. 8, it is possible to drive the piston 34 partially during a fill or discharge stroke to pump less than a full pump chamber volume worth of dialysate, additive 228 or ultrafiltrate 232.

The additive flowrate and the ultrafiltrate flowrate can be doubled by opening second intake valves 214 and 218, either simultaneously or during the same complete pump cycle or opening second exhaust valves 216 and 220 simultaneously or within the same overall pump cycle, respectively. The total volume of additive 228 and ultrafiltrate 232 is calculated knowing the total volume within fluid pumping changes 204 and 210, the number of strokes that the second intake and exhaust valves are opened over a given period of time, and the percentage of a stroke employed (partial stroke or full stroke). As described below in connection with Section VIII, the volume of fluid pumped can alternatively be measured, for example, using a capacitance fluid volume sensor.

While arrangement 200 has been illustrated with two pumps, it should be appreciated that the multiplexing flow illustrated in connection with FIGS. 17 to 20 is operable with dialysis systems having a single pump or three or more pumps. Further, while alternating pumps 204 and 210 is preferred in one embodiment, both pumps can be pulling fluid and discharging fluid at the same time in an alternative embodiment. Further, where three or more pumps exist, one pump can pull fluid while one or more pumps pulls fluid, pushes fluid or is idle.

VI. Knowledge-based Expert Fluid Delivery Systems

Any of the therapies operable with the cassette-based embodiments of the present invention (hemodialysis, CFPD, APD and tidal flow peritoneal dialysis) may employ multiple pumps, such as two, three, four or even more fluid pumps.

Also, multiple solutions may be used. Hemodialysis pumps blood and dialysate. CFPD uses a number of different solutions, such as the continuously flowing dialysate, a supply of one or more concentrated additives, ultrafiltrate produced by the patient, as well as others. With APD and tidal flow, the systems may employ a plurality of fluid supply bags operating in parallel.

The various therapies also include a multitude of fluid flow destinations. Besides the obvious destination of pumping fluid to the patient, the therapies also pump to an ultrafiltrate container, a drain bag, a sample container, an accumulator or other destination. The therapies yield a complex matrix of fluid flow starting points, fluid pumps and fluid flow destinations. Adding to the complexity, automated systems allow a multitude of input parameters typically to be varied by the patient or doctor. The patient or doctor can for example control the overall therapy time, the fluid flowrate and various dwell periods in connection with batch systems and a concentration of electrolyte or other additives in a CFPD solution, just to name a few.

It is very difficult if not impossible therefore to predetermine and store in memory a pumping schedule for each possible combination of parameters selected by the patient and/or doctor. Accordingly, the present invention provides the following expert system and method for determining a pumping schedule "on the fly" after the user inputs values for various parameters. The expert system and method for scheduling the pumping of the dialysis therapy is applicable to any combination of solutions, pumps, and destinations, such as one or more solutions, one or more pumps, and one or more destinations. FIG. 21 illustrates one possibility that includes three solutions, three pumps, and three destinations.

FIG. 21 illustrates schematically a hardware configuration for: (i) Solution 1 to Solution 3; (ii) pumps P1 to P3; and (iii) Destination 1 to Destination 3. To provide a frame of reference, Solution 1 is tabbed as a patient solution, i.e., the solution leaving the patient in CFPD, Solution 2 is an accumulator solution and Solution 3 is a concentrate solution. Destination 1 is tabbed as a filter or cartridge, Destination 2 is the accumulator and Destination 3 is an ultrafiltrate container. The CFPD system includes an accumulator in an embodiment that accumulates a portion of the fluid. The accumulator mixes various fluids and chemicals and stabilizes those fluids and chemicals. The accumulator can also be used to provide a sample of the fluid for analysis. Although a single chemical concentration additive is illustrated, the dialysis system, and in particular CFPD, can include many different chemicals and additives.

As illustrated, the accumulator is both a solution or source and a destination. The designation of a particular entity as a solution or destination may, in certain instances, be arbitrary, which is allowable as long as the entity is consistently maintained as a solution or destination. For example, the patient could be either a solution as illustrated, wherein a pump pulls the solution from the patient, or a destination (not illustrated), wherein a pump pushes fluid to the patient. The patient could further alternatively be a solution and a destination. On the other hand, the concentration solutions cannot alternatively be arbitrarily assigned as a destination. Likewise, the ultrafiltrate collection destination cannot otherwise be designated a solution.

FIG. 21 illustrates the various fluid pathways existing for one embodiment between the solutions, the pumps and the destinations. As illustrated, Pump 1 can pull from all three solutions but output to only Destination 1. This is a physical limitation set by the fluid pathways in the disposable cassette and/or by external tubing. Likewise, Pump 2 is connected fluidly to be able to pull fluids from any of the three solutions and to be able to pump to any of the three solutions. Pump 3 can only pull fluid from Solution 1 but can pump out to any of the three destinations. This arrangement is illustrated merely for purposes of describing the expert system of the present invention and can be altered to achieve any desired configuration.

Referring now to FIG. 22, a state diagram for each of the pumps is illustrated. The state diagram illustrates physical restraints existing inherently in the pumps as well as operational characteristics desired by the system implementers. For example, the pulling and pushing states include a self-lock that prevents a pump to transition from a pulling state to another pulling state or from a pushing state to another pushing state. This is due to the physical limitations of the pump. As described above, the pump includes a piston head 36 that pulls apart a flexible membrane from a rigid portion of the disposable cassette to pull in fluid and pushes that same membrane towards the rigid portion to push out fluid. Assuming a complete stroke is made (no partial stroke), the pumps are arranged physically so that the next movement after pulling must be a pushing movement and the next movement after pushing must be a pulling movement.

Each of the states is allowed to transition, however, to an idling state, a characteristic desired by the implementers. When a pump is done pulling, it may do nothing, i.e., idle. When a pump finishes pushing, it may also do nothing. When a pump is finished idling, it may idle again. A pump may idle for as long as is desired until transitioning to the next active state based on the previous activity of the state.

FIG. 23 sets forth various rules or restrictions that are placed in software to determine, in part, a pumping schedule. The schedule is based on: (i) the rules of FIG. 23; (ii) various inputs by the doctor/patient; (iii) a number of calculations based on the inputs; and (iv) a number of constants set for example by the physical limitations of the system (e.g., pump chamber volume is ten ml). The rules or restrictions serve to provide a basis upon which a microprocessor of the controller of the present invention can make decisions to develop a flow schedule.

Rules 1 to 6 codify the physical flow restraints between the solutions, pumps and destinations illustrated in connection with FIG. 21. FIG. 23 does not exhaust all the possible rules that may be derived from the physical connections between the solutions, pumps and destinations. Rules 1 to 6 set forth merely examples of rules that might be implemented based on the fluid flow connections.

Rules 7 to 13 set forth certain restrictions that are based on the state diagram of FIG. 22 and other restrictions based on the particular therapy employed. For example, although the system is connected fluidly so that Solution 2 can be pumped to Destination 2, Rule 7 in software forbids such a flow from taking place. Rules 8 and 9 set forth similar restrictions.

Rules 12 and 13 designate restrictions that simplify the calculations made to generate the flow schedule. Rule 12 specifies that a pump pumps only from one source during any giving pulling stroke. Rule 13 designates that a pump delivers fluid to only a single destination during a pump discharge stroke. These rules do not conflict with the multiplexing flow of Section V, wherein the pumps pump dialysate for a number of complete strokes and then pump an additive or ultrafiltrate for one or more complete strokes. One alternative embodiment in Section V does, however, include partial strokes which may or may not involve pumping fluid from more than one source or pumping fluid to more than one destination during a given stroke. The expert system can be modified to include such paprtial strokes; however, certain of the algorithms discussed below would be more complicated.

Figure 24:
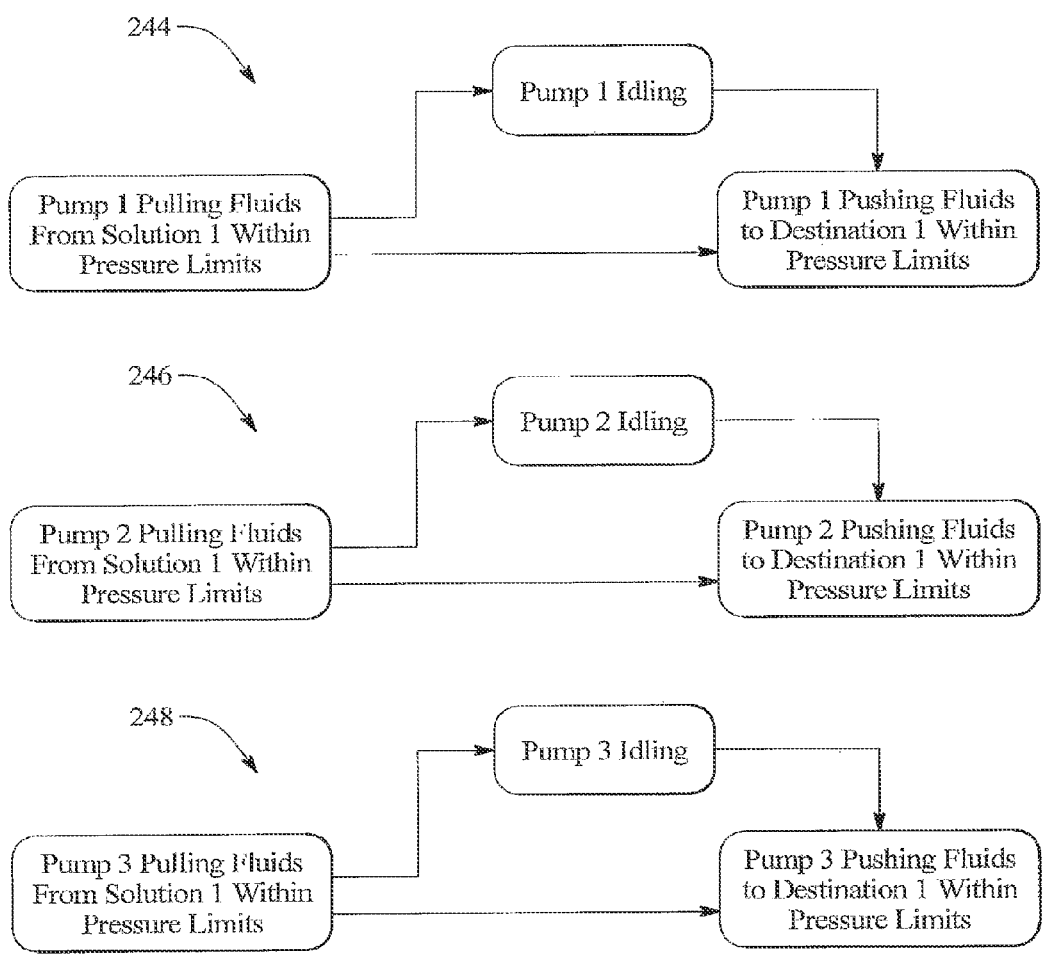
FIG. 24 shows schematic diagrams illustrating pumping modules that are part of the outcome of the fluid flow connections of FIG. 21, a state diagram of FIG. 22 and the software rules implemented in FIG. 23.

FIG. 24 sets forth one outcome from the diagrams and rules of FIGS. 21 to 23. FIG. 24 illustrates three function modules 244, 246 and 248 that provide the controller with three options based on Rule 1 illustrated above in FIG. 23. That is, Rule 1 allows pumping to occur from Solution 1, through Pump 1 to Destination 1, as indicated by function module 244; pumping to occur from Solution 1, through Pump 2 to Destination 1, according to function module 246; and pumping to occur from Solution 1, through Pump 3 to Destination 1, as indicated by function module 248. Each of the function modules 244, 246 and 248 also requires that the pumping be maintained within specified pressure limits. The pumping is controlled to occur over a designated period of time, moving the flexible membrane of the cassette at a particular velocity and moving the third under a specified pressure limit.

FIG. 24 illustrates three possible ways to accomplish moving fluid from Solution 1 to Destination 1, e.g., from the patient to the filter. Depending on other fluid pumping actions taking place simultaneously, one or more of the function modules 244, 246 and 248 may be eliminated due to other rules, such as rules restricting: (i) pumping from the same solution to two pumps at the same time; (ii) pumping two different solutions using the same pump at the same time; (iii) pumping to two different destinations using the same pump at the same time; or (iv) pumping from two pumps to the same destination at the same time. Thus, the schedule at a particular point in time may have to choose one of the three function modules 244, 246 and 248.

Alternatively, the controller can choose to pump from Solution 1 to Destination 1 at a different point in time, for example, if all three pumps are already assigned to another pumping assignment. The controller, however, is also bound by the therapy parameters that require a certain amount of fluid to be pumped from the patient to the filter over a certain amount of time. The controller cannot therefore delay the pumping from Solution 1 to Destination 1 for too long a period. It should be appreciated from this illustration that the rules and inputted parameters cooperatively provide the controller with a framework upon which to generate a pumping flow schedule.

Figure 25:
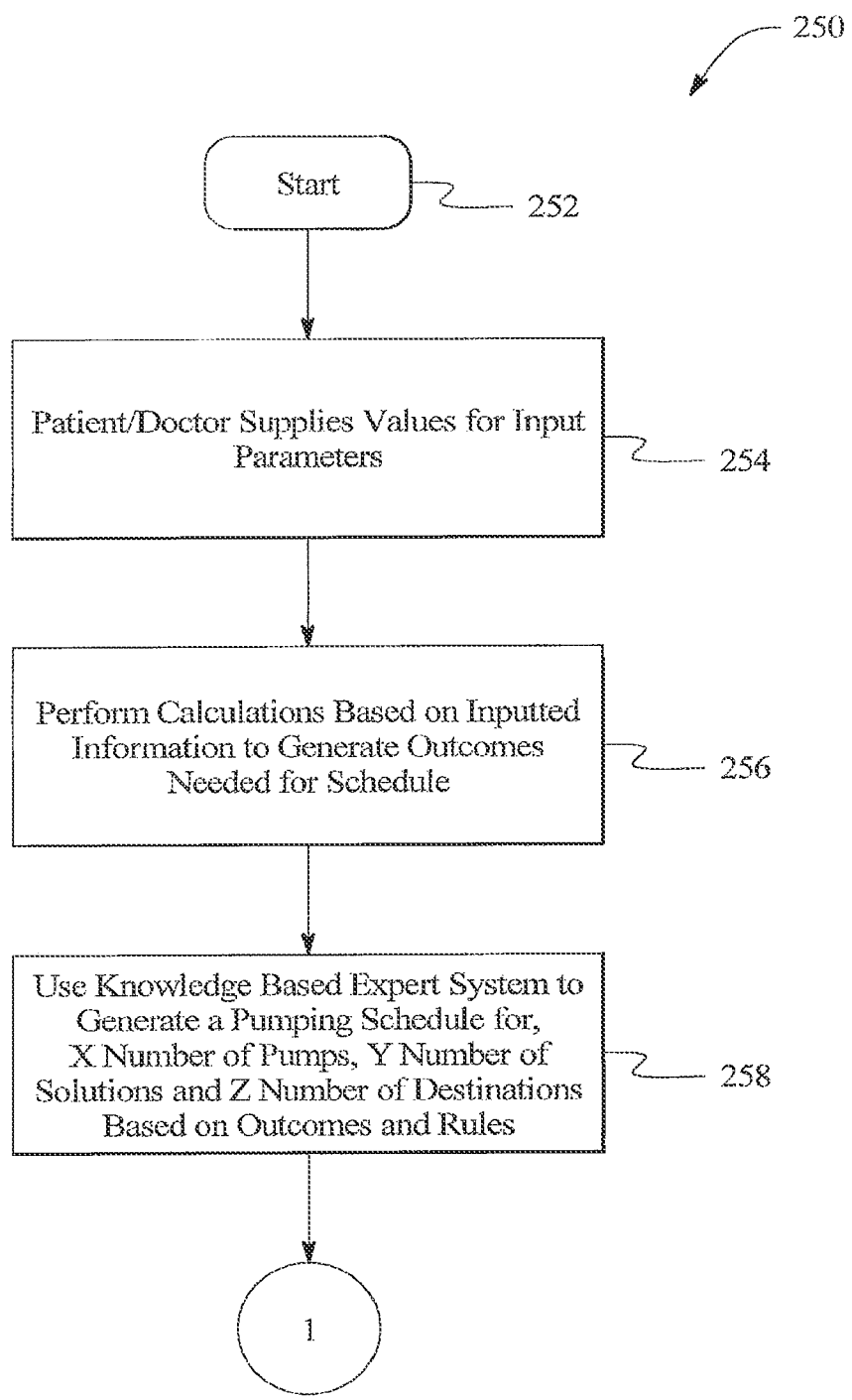
FIGS. 25 and 26 are process flow diagrams illustrating schematically an embodiment of the expert pumping system and method of the present invention.
Figure 26:
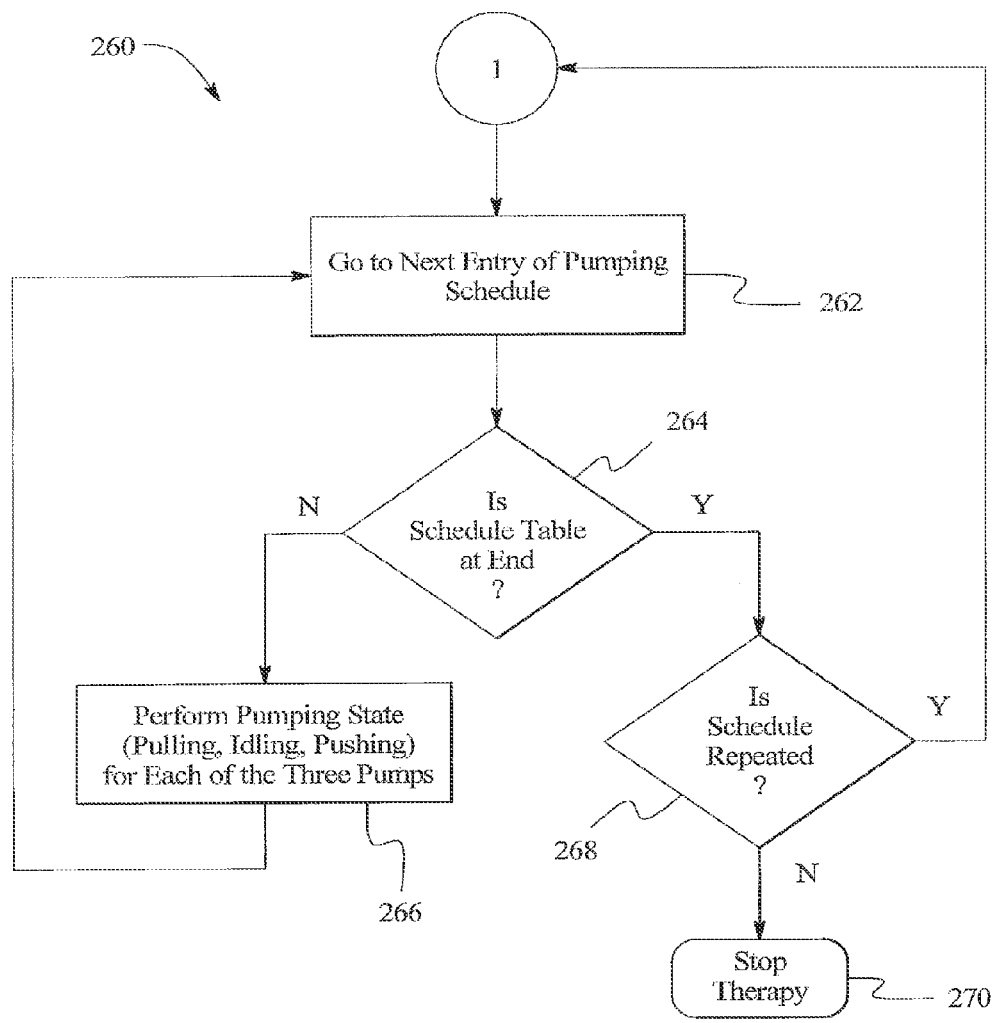

FIGS. 25 and 26 illustrate high level process flow diagrams 250 and 260 that show the control of the various pumps prior to and after developing the flow schedule, respectively. Process flow diagram 250 illustrates the generation of the pumping schedule. Process flow diagram 260 illustrates the actuation of the pumping schedule.

Upon starting therapy as indicated by oval 252, the patient or doctor supplies values for various input parameters, as indicated by block 254. Input devices, such as devices 184 shown in FIG. 12, can be used for example to select a value for a parameter from a range of possible values. Otherwise, the patient or doctor can type or key a value using a touch screen or hand key pad.

FIG. 27 illustrates various input parameters 272, such as the stroke volume (this can alternatively be a constant, e.g., 10 ml, as described above in connection with the multiplexing Section VI). The patient or doctor enters the total therapy time, which as illustrated in FIG. 27 is, for example, 480 minutes. The dialysis fluid flowrate is inputted to be 250 ml/minute in the example of FIG. 27. Concentrate is added at a flowrate of 5 ml/minute and ultrafiltrate is removed at a flowrate of 2 ml/minute. The patient or doctor enters the amount of ultrafiltrate that is expected to be generated by the patient, which is 2 ml/minute for example. The patient or doctor also enters a ratio (R) between the dialysate flowing through the main regeneration loop and flowing through an accumulator loop. FIG. 27 merely sets forth examples of inputs. The doctor or patient can make other types of inputs alternatively or additionally.

After providing the necessary inputs as indicated by block 254, the system and method performs a number of calculations based on the inputted information, as indicated by block 256. The calculations also use a number of constants and/or other variables. FIG. 28 illustrates various algorithms or formulas used by the expert system of the present invention to generate the outcomes needed, as indicated by block 256, to develop a knowledge-based schedule for pumping.

The equations 274 include calculating a cycle time, which is equal to the total therapy time divided by a number of cycles. In an embodiment, the schedule outputted is a portion of the total pumping schedule. The schedule is therefore repeated or cycled a number of times to achieve the overall goals of the therapy. Equations 274 also include a stroke time that is a function of the stroke volume and the dialysate flowrate. The system calculates a number of patient pump strokes, which is a function of the cycle time and the stroke time. An accumulator flowrate is calculated knowing the dialysate flowrate and the ratio R described above in connection with the inputs 272 of FIG. 27.

The number of accumulator strokes (number indicates to or from, not both) is equal to the cycle time multiplied by the accumulator flowrate, which is divided by the stroke volume. A number of strokes cycles pulling from the concentration source is calculated via the cycle time multiplied by the inputted concentration flowrate, which is divided by the constant stroke volume. The number of ultrafiltrate strokes is a function of the cycle time, the inputted ultrafiltrate removal rate, the inputted concentrate addition flowrate and the stroke volume. It should be appreciated that additional or alternative equations may be used. Equations 274 of FIG. 28 are illustrated merely to describe the expert system and method of the present invention.

FIG. 29 illustrates the outputs needed to generate the pumping schedule, as indicated by block 256 in FIG. 25. Outputs 276 are based on or are applied to the entire therapy or are otherwise constant throughout the entire therapy. Outputs 278 are based on or applicable to a single cycle. For example, assuming the desired number of cycles is 48 (schedule repeated 48 times) and the total therapy time is 480 minutes, the time for each cycle is ten minutes. The outputs 276 are based on the total therapy time of 480 minutes in the illustrated embodiment, while outputs 278 are based on a cycle time of 10 minutes.

Regarding outputs 276, the recirculation stroke number of 12,000 is the total number of times any of the three pumps (three pumps collectively) pump from the patient. In a similar manner, the number 4,000 represents the number of strokes that the three pumps make collectively to the accumulator. The pumps pump collectively another 4,000 strokes from the accumulator. The pumps in combination pump from the one or more concentration sources a total of 240 times over the therapy. The pumps in combination pump to the ultrafiltrate container a total of 336 times during the therapy. The difference in volume produced by the from concentrate and to ultrafiltrate strokes is due, at least in part, to a volume of ultrafiltrate produced by the patient.

The outputs 278 are based on the ten minute cycle and cover approximately ⅛sth of the time of the outputs 276, which cover the entire 480 minute therapy time. The final two outputs 278 set forth the number of strokes (248) to Destination 1, i.e., to the cartridge or filter. The last illustrated number (338) is the total number of fill strokes over the 10 minutes, which is a combination of the 250 patient strokes, the 83 from accumulator strokes and the five strokes from concentrate.

After performing the calculations and achieving the needed outputs as indicated by block 256, the expert system uses the calculated outcomes, the rules, the state diagram and the function modules set forth above to produce a pumping schedule, as indicated by block 258. The controller uses the schedule to control X number of pumps, for Y number of solutions and Z number of destinations, wherein X, Y and Z can each be one or greater. A portion of a sample schedule is illustrated in FIG. 30. Based on the information provided above, knowing that a stroke time is 2.4 seconds and each cycle lasts 10 minutes, the schedule 280 has two hundred fifty entries 282. For ease of illustration, twenty-five entries or one minute's worth of pumping is illustrated. In actuality, the schedule includes two hundred twenty-five additional entries 282 (as indicated by dots), i.e., nine additional minutes worth of pumping.

Schedule 280 includes a column for each of the solutions discussed above in connection with FIG. 21, namely, the patient solution, the accumulator solution, and the concentrate solution. Schedule 280 includes a column for each of the destinations discussed above in connection with FIG. 21, namely, the cartridge or filter, the accumulator and the ultrafiltrate container. Using the rules, desired outputs and ensuring that no pressure limit is exceeded, the controller generates the schedule of entries 282 as illustrated in FIG. 30. According to the first entry 282, during the first 2.4 seconds, Pump 2 makes one complete stroke pulling fluid from the patient, Pump 1 makes one complete stroke pulling fluid from the concentration, and Pump 3 makes one complete stroke pushing fluid to the ultrafiltrate container. In the next 2.4 seconds, the pumps maintain a different profile. As is seen readily, in various entries 282 less than all three of the pumps are activated. Any percentage of the pumps can be activated in any of the entries 282.

Schedule 280 allows other rules to be implemented. For example, the schedule can apportion equal pumping strokes for each pump over the total therapy or over a cycle, so that the pumps wear approximately evenly. Other rules may be implemented to rest a pump after a particular number of strokes, so that the pump can, for example, purge air or perform any necessary resetting function.

After generating the pumping schedule as indicated by block 258, the controller implements the pump schedule to achieve the desired flowrates and the desired overall fluid pumping volumes as indicated by process flow diagram 260 of FIG. 26. The system finds the next entry 282 of the pumping schedule as indicated by blocks 262. At the start of therapy or the start of a cycle within the therapy, the next entry is the first entry 282. Also, as determined in connection with diamond 264, the previous entry may have been the last entry. Otherwise, if the previous entry is not the last entry of the particular cycle table, the system performs the pumping state, e.g., pulling, idling, or pushing, for each of the three pumps, as indicated by block 266. Afterward, the system returns to block 262 and the current cycle is carried out until the schedule reaches the end, as indicated by diamond 268. When the cycle reaches its end, the system determines whether the schedule is repeated or not. As discussed above, the schedule represents one cycle of a plurality of cycles, e.g., ten cycles. If another cycle is required to complete the therapy as determined in connection with diamond 268, the entire sequence of process flow diagram 260 is repeated. If the total number of cycles has been completed as determined in connection with diamond 268, the therapy is ended, as indicated by oval 270.

VII. Integral Port Vent

Figure 31:
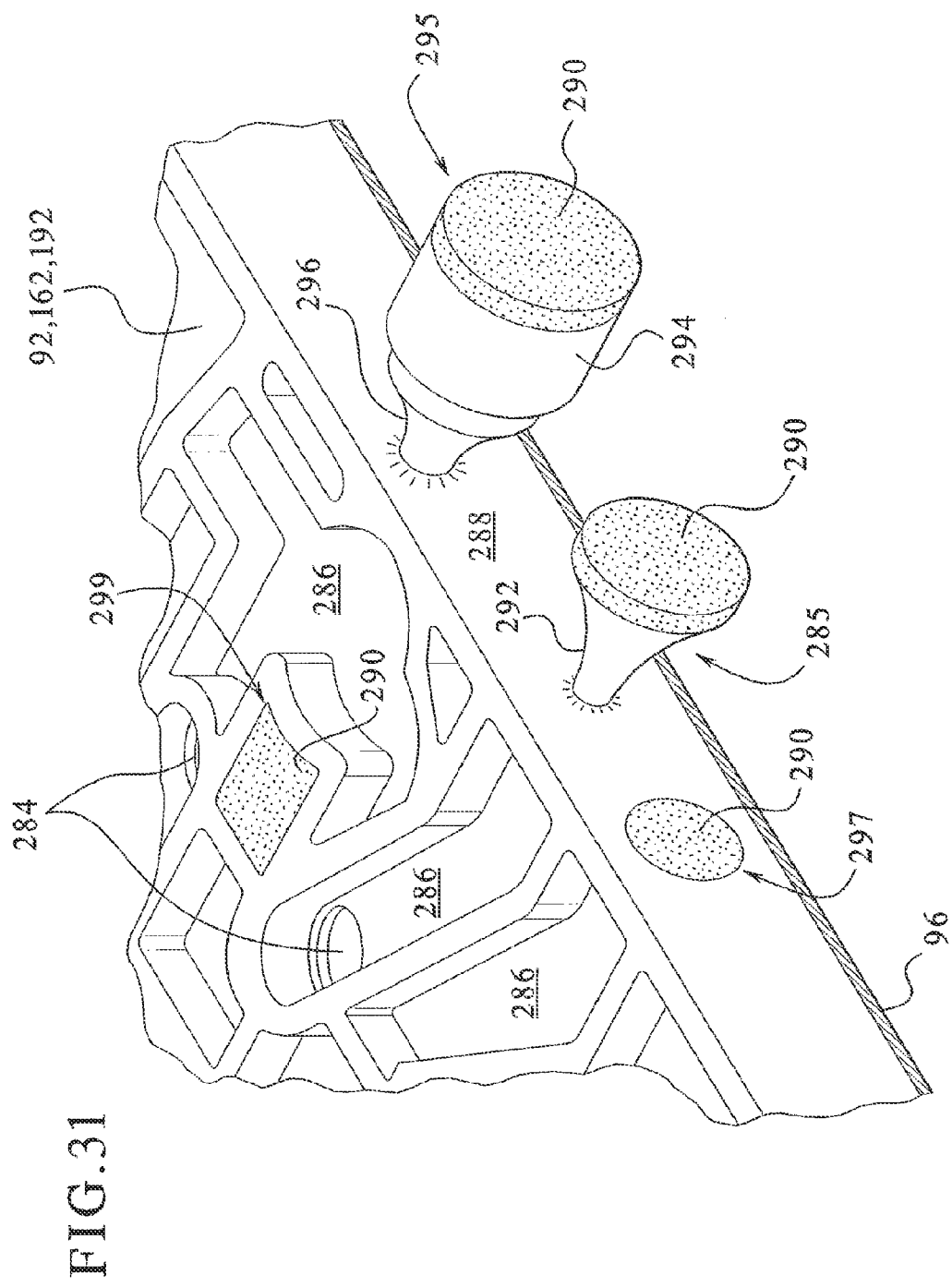
FIG. 31 is a cutaway perspective view of a rigid portion of a disposable cassette showing various embodiments for a port vent of the present invention.

Referring now to FIG. 31, various embodiments for cassette-based port vents of the present invention are illustrated. The disposable cassettes described herein include a vent port having a venting membrane. The membranes vent the priming volume (air existing in tubes before the start of therapy) and gasses generated during therapy. The cassette is provided with an air sensor, for example, a capacitance fluid sensor described below, which detects when air or other gases enter the system. When air or other gases, or a particular level thereof, enters the system, the controller of the system (not illustrated) vents the air or gases through a vent, such as vent 285 or 295.

The cassette has a portion shown above as reference numbers 92, 162 and 192, which are made of a rigid or semi-rigid plastic material as described above (referred collectively as rigid portion). Rigid portions 92, 162 and 192 define a plurality of holes or apertures 284 and slots 286. Apertures 284 operate, via one of the flexible membranes, with valve plungers 42 in an embodiment. Slots 286 form fluid or gas pathways when enclosed by the membranes 94 and 96. Certain slots lead to a venting port, such as port vents 285, 295, 297 and 299. The slots 286 communicate fluidly in an embodiment with a patient fluid line, a regeneration device for CFPD, a fluid supply for APD or other therapy component. Port vents 285, 295, 297 and 299 are operable with each of the therapies described herein.

Port vents 285, 295, 297 and 299 are alternative embodiments. Vents 285 and 295 include an extension that is formed integrally with the rigid portion 92, 162 or 192 of the associated disposable cassette. Vents 285 and 295 extend from sidewall 288. Vents 297 and 299 include apertures that are formed integrally with the rigid portion of the cassette. Port vent 297 for example is formed in sidewall 288 of the rigid portion. For convenience, the upper flexible membrane has been removed from the rigid portion to illustrate the holes 284, slots 286 and to better see Vent 299. Lower flexible membrane 96 is illustrated, adhered or sealed to the rigid portion.

Port vent 285 includes a flared port 292 that extends integrally from sidewall 288. Thus when rigid portion 92, 162 or 192 is formed, e.g., molded or extruded, to have the apertures 284 and slots 286, the flared port 292 is also formed. Port 292 defines a hole that communicates fluidly with a hole defined by sidewall 288, the port hole and sidewall hole in turn communicating fluidly with one of the slots or fluid pathways 286. Although port 292 is shown having a conical or flared shape, it should be appreciated that port 292 includes any suitable shape, such as a straight cylindrical shape, hose barbed shape or other shape that lends itself to being coupled to the filter 290.

Filter 290 is disposed on and supported by integral port 292 via any suitable method, such as adhering, heat sealing, mechanically attaching and any combination thereof, for coupling filter 290 to port 292. For any of the vent embodiments described herein, filter 290 is or includes a hydrophobic membrane. One suitable hydrophobic membrane is made by Millipore, 80 Ashby Road, Bedford, Mass. 01730. Alternatively, the filter is made from a material such as polytetrafluoroethylene ("PTFE"), Teflon, nylon, polyethylene, polypropylene, polystyrene, polyvinylchloride ("PVC"), polyvinylidene, a polyamide, Gortex and any combination of these. In an embodiment, the filter has a pore size of between zero and one micron, and in one preferred embodiment about 0.2 micron. A pore size of 0.2 micron is suitable to vent the priming volume and exhaust gases generated during therapy.

Alternative port vent 295 also includes an integrally formed flared port 296 that can alternatively be any of the shapes described above for port 292. Any of the embodiments for the filter 290 can also be used with port vent 295. The filter 290 is bonded, sealed or mechanically connected to a bushing 294. The bushing 294 can be a section of tubing or pipe of the same or different material as rigid portion 92, 162 and 192 and consequently of the same or different material as port 296. Bushing 294 is adhered, sealed or mechanically attached to integral port 296. In an embodiment, bushing 294 is removably attached to port 296, e.g., via mating threads.

Alternative vents 297 and 299 do not include an integrally formed port, such as ports 292 and 296. Instead, a feature of rigid portion 92, 162, 192 defines an opening sized to house a filter 290. For vent 297, sidewall 288 defines an aperture into or onto which filter 290 is filled. Filter 290 can be attached to sidewall 288 via any of the methods discussed above. A separate collar or cover (not illustrated) can be provided for additional support.

Vent 297 is disposed vertically. Vent 299 is disposed horizontally on or within a shape or feature defined by the rigid portion. The shape or feature is formed integrally as a hole 284 or slot 286. The hole or slot houses or supports filter 290 of vent 299 via any of the methods of attachment described above. Further, upper flexible membrane 94 can seal around or to an outer portion of filter 290 to provide additional mounting support for vent 299.

As described above, one or more pumps is connected fluidly to one or more solution supplies and one or more solution destinations. The pumping of the fluid may inadvertently entrain air within the fluid. Also ultrafiltrate produced by the patient may contain various off-gases from the peritoneal cavity. When the filter 290 is made of a hydrophobic material, i.e., one that allows air but not fluid escape therefrom, the port vents 285 and 295 can communicate directly with a fluid pathway, such as via one of the slots 286. Here, the filter 290 holds the pressure of the fluid pump. If the filter is not capable of separating air from fluid, the port vents 285 and 295 are alternatively connected to air flow lines that contain vent gases but not fluid. Such air flow lines can be achieved for example via fluid sumps and chambers that collect fluid at the bottom and collect air or other gases at the top. One such chamber is shown below in connection with FIG. 32. In FIG. 31, slots 286 that communicate with ports 292 and 296 of vents 285 and 295, respectively, and directly with vents 297 and 299 are alternatively air vent slots 286 rather than fluid pathways.

VIII. Air Separation Chamber

Referring now to FIG. 32, one embodiment of an air separation chamber 300 having a capacitance fluid volume sensor is illustrated. The capacitance sensor is also discussed in connection with a fluid pump in patent application entitled, "Capacitance Fluid Volume Measurement," Ser. No. 10/054, 487, filed on Jan. 22, 2002, incorporated herein by reference. The capacitance sensor in operation with the fluid pump enables air entrained in the medial fluid to be sensed and expelled at the time of pumping. The pumping cassette-based air separation chamber operates with the cassette-based port vents 285, 295, 297 or 299 described in Section VII.

The pumping cassette-based air separation chamber fluid is placed typically upstream of a fluid heater. In an embodiment, the cassette also defines a fluid heating path that receives fluid from one or more of the pumps. The pump or cassette-based air separation chamber is not able to remove air introduced into the fluid due to heating because the chamber operates upstream of the heater. Air separation chamber 300 is therefore placed downstream of the heater, e.g., downstream of the cassette, in one embodiment and removes air entrained in the medial fluid due to heating. The fluid leaving chamber 300 is pumped via a patient line to the patient. Both the pump-based separation chamber and the chamber 300 of FIG. 32 are operable while the system pumps fluid and do not require the system to stop to purge gas. It should be appreciated, however, that air separation chamber 300 is operable with medial fluid systems, such as dialysis systems, either upstream, downstream or upstream and downstream from the fluid heater.

The capacitance sensor uses capacitance measurement techniques to determine the volume of a fluid, including air, inside of a chamber. As the volume of the fluid changes, a sensed voltage that is proportional to the change in capacitance changes. Therefore, the sensor can determine whether the chamber is, for example, empty, an eighth full, quarter full, half full, full, or any other percent full of fluid or air. Each of these measurements can be made accurately, for example, at least on the order of the accuracy achieved by known gravimetric scales or pressure/volume measurements. The capacitance sensor, is simple, non-invasive, inexpensive and accurate.

Generally, the capacitance C between two capacitor plates changes according to the function $C=k*(S/d)$, wherein k is the dielectric constant, S is the surface area of the individual plates, and d is the distance between the plates. The capacitance between the plates changes proportionally according to the function $1/(R \times V)$, wherein R is a known resistance and V is the voltage measured across the capacitor plates.

The dielectric constant k of medical fluid or dialysate 302 is much higher than that of air or gas 304. As more air becomes trapped inside chamber 300, the overall dielectric changes from a higher dielectric dialysate to a lower dielectric air due to the increasing amount of air between conductive plates 306 and 308. Capacitance plates 306 and 308 are disposed inside an insulative or dielectric housing 310 in an embodiment. The conductive plates 306 and 308 are located closer to an inner surface of housing 310 than an outer surface of the housing.

As housing 310 of chamber 300 fills with medical fluid or air, the overall capacitance changes, i.e., increases or decreases, respectively. The sensor generates a high impedance potential across the active and grounded capacitor plates 306 and 308, respectively. The high impedance potential is indicative of an amount of fluid, such as dialysate or air, in housing 310. Housing 310 is made from an inert, medically safe electrically insulative material, such as polytetrafluorathelene ("PTFE"), Teflon, nylon, polyethylene, polypropylene, polystyrene, polyvihydrochloride ("PVC"), polyvinylidene, a polyimide and any combination of these.

A capacitance sensing circuit (not illustrated) amplifies the high impedance signal to produce a low impedance potential. The low impedance potential is also fed back to a guard plate 312, which protects the sensitive signal from being effected by outside electrical influences. The amplified potential is converted to a digital signal and fed to a system processor (not illustrated), where it is filtered, converted and/or summed. A video monitor 176 (FIG. 12) provides visually a volume and/or a flowrate indication to a patient or operator in an embodiment. Additionally, the processor controls one or more pumps and/or valves of the system, for example, to terminate dialysate flow upon reaching a predetermined overall volume or to shut off flow if a particular amount of air is sensed.

In the illustrated embodiment, the housing 310 of chamber 300 forms a clamshell with first and second portions corresponding to conductive plates 306 and 308. Spherical, cubical, rectangular or other shapes are possible for housing 310. The portions of housing 310 form a rigid, fixed volume, clamshell shape. The portions can be formed integrally together or fixedly or removably sealed together.

Housing 310 defines inlet and outlet ports 314 and 316, respectively. Inlet port 314 enables medical fluid 302, for example, dialysate, to enter the chamber 300, while outlet port 316 enables medical fluid 302 to exit chamber 300. In the embodiment illustrated, outlet port 316 resides at the bottom of housing 310 of chamber 300 to allow the heavier medical fluid 302 to separate from any air 304 entrained therein. The air 304 as illustrated tends to collect towards the top of housing 310. In alternative embodiments, inlet port 314 and outlet port 316 can be located at different areas of housing 310 and have various orientations with respect to one another.

Inlet ports 314 and 316 can have any configuration known to those of skill in the art for connecting sealingly to inlet tube 318 and outlet tube 320, respectively. Ports 314 and 316 can be a straight tube (as illustrated), angular tube, hose barb, compression fitting, threaded or other configuration. Inlet and outlet ports can be of the same size or sized differently and be sized for a standard size inner tube diameter of tubes 318 and 320. Tubes 318 and 320 run to various places in accordance with the particular therapy.

A baffle 322 is provided inside housing 310 and near inlet 314 to deflect incoming fluid 302 upward or away from outlet port 316. Baffle 322 facilitates and enhances the separation of air 304 from fluid 302. Baffle 322 reduces the likelihood that air will exit through outlet port 316. Baffle 322 tends to direct air or gas bubbles upward so that the bubbles have to change direction to exit outlet port 316. Baffle 322 can be formed integrally with housing 310 or be attached via a medically safe adhesive, via an attachment mechanism, heat sealed, sonically sealed or attached via methods otherwise known to those in the art. Baffle 322 can have any desired shape and be configured to fit the shape of housing 310. In an alternative embodiment, multiple baffles 322 are provided. A second one or more baffle 334 can be suitable placed near vent port 324 to help stop fluid from exiting housing 310.

Housing 310 defines air venting port 324 in an embodiment. Alternatively, any of the ports 314, 316 and 324 are separate pieces that attach in a suitable manner to housing 310. Air vent port 324 can be of a same or different size as inlet and outlet ports 314 and 316 and can have any of the configurations described above in connection with ports 314 and 316 for sealing to air vent tube 326. Air 304 or other gases, such as gases formed within the peritoneal cavity or gases used to pressurize the system, escape housing 310 and chamber 300 via venting port 324.

Vent tube 326 connects in an embodiment to various flow control and fluid control devices. One or more valves 328 are connected fluidly with vent tube 326. In an embodiment, one or more of the valves 328 are solenoid or electrically operated valves, which are opened or closed by the system processor based on a signal produced via capacitance plates 306 and 308. One or more of valves 328 can alternatively be operated manually. A sump or fluid trap 330 is provided additionally in an embodiment upstream, between or downstream of valves 328 to collect any fluid that escapes through vent port 324. An additional solenoid or manual valve 328 is provided downstream of sump 330 in an embodiment to allow the sump or fluid trap to drain.

A venting membrane 332 is placed at the end of vent tube 326. Venting membrane 332 can be of any type known to those of skill in the art. In an embodiment, venting membrane 332 is a hydrophobic membrane that enables air 304 but not fluid 302 to escape from venting tube 326. Alternatively, valves 328 and sump 330 may keep moisture from contacting membrane 332 sufficiently that membrane 332 is designed for contact with gas only. In one embodiment, air or gas 304 can escape from chamber 300 through membrane 332 but cannot enter chamber 300 through membrane 332. Membrane 332 can be made of any of the materials described above for the filter 290 of FIG. 31.

In operation, the capacitance sensor generates a signal or voltage proportional to or indicative of the amount of fluid 302 or air 304 within the housing 310 of chamber 300. When a predetermined amount of air or gas 304 is detected, the processor opens one or more valves 328 to allow the gas or air 304 to discharge or be purged from the housing 310 of chamber 300. After a certain amount of time or after a particular dielectric or voltage is sensed, the processor closes the one or more valves 328. This cycle is repeated throughout the medical delivery, e.g., dialysis therapy. In an embodiment, if a particular amount of gas is sensed, the system enters an alarm condition, wherein fluid pumping stops until a safe fluid level is reached.

In an alternative embodiment, multiple capacitance sensors, i.e., multiple sets of plates 306, 308 and 312 are used. The sensors produce collectively an output indicative of an amount of fluid 302 or air 304, which is used to open or close valves 328. The valves 328 are controlled via the collective signal as described above.

In a further alternative embodiment, an air separation device 400 is provided. Device 400 includes two valves 328 operating in series with a fluid trap 330 placed between valves 328. Device 400 does not require the remainder of chamber 300. The controller (not illustrated) commands valves 328 at certain points in time to open sequentially, out of phase, so that any fluid that escapes with the volume of gas flowing between the valves can flow to trap 330. The pressure of fluid 302 pressurizes air or gas 304 trapped between valves 328. Outer valve 328, adjacent to membrane 332, is opened to relieve pressure between the valves 328 and allow the excess gas to escape. Membrane 332 is optional. Valve 328 downstream of fluid trap 330 is provided to allow fluid to drain automatically. Device 400, like chamber 300, can operate while the fluid pumps are in operation and does not require the pumps to be shut down intermittently. Device 400 can be cassette-based in an embodiment and placed upstream and/or downstream of the fluid heater.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A peritoneal dialysis method comprising:
   enabling the mating of a disposable pumping cassette with a peritoneal dialysis machine;
   moving first and second piston heads towards the disposable pumping cassette to contact and move first and second respective portions of a flexible membrane of the pumping cassette into a rigid portion of the pumping cassette to push (i) fresh dialysate out of the pumping cassette through a patient line towards a patient or (ii) spent dialysate to a drain line towards a drain; and applying from a pneumatic pressure source (a) a first vacuum to mate the first portion of the flexible membrane to the first piston head and (b) a second vacuum to mate the second portion of the flexible membrane to the second piston head to cause the first and second portions of the flexible membrane to respectively follow the first and second piston heads as either piston head is moved away from the pumping cassette to pull (i) fresh dialysate from a fresh dialysate supply line or (ii) spent dialysate from the patient line to fill a respective first or second pump chamber of the pumping cassette.

2. The peritoneal dialysis method of claim 1, which includes moving the first piston head towards the pumping cassette to push fresh dialysate through the patient line or spent dialysate through the drain line while moving the second piston head away from the pumping cassette to pull fresh dialysate from the dialysate supply line or spent dialysate from the patient line, respectively.

3. The peritoneal dialysis method of claim 2, which in a second stroke includes moving the first piston head away from the pumping cassette to pull fresh dialysate from the dialysate supply line or spent dialysate from the patient line, while moving the second piston head towards the pumping cassette to push fresh dialysate through the patient line or spent dialysate through the drain line, respectively.

4. The peritoneal dialysis method of claim 1, which includes prompting a fluid connection of the patient line to an indwelling patient catheter after mating the pumping cassette to the peritoneal dialysis machine.

5. The peritoneal dialysis method of claim 4, which includes moving the first and second piston heads and applying the first and second vacuums to prime the pumping cassette with fresh dialysate prior to the prompting of the fluid connection.

* * * * *